(12) United States Patent
Hariton et al.

(10) Patent No.: US 10,779,939 B2
(45) Date of Patent: Sep. 22, 2020

(54) PROSTHETIC VALVE WITH LEAFLET CONNECTORS

(71) Applicant: CARDIOVALVE LTD., Or Yehuda (IL)

(72) Inventors: Ilia Hariton, Zichron Yaakov (IL); Meni Iamberger, Kfar Saba (IL); Aviram Baum, Tel Aviv (IL)

(73) Assignee: CARDIOVALVE LTD., Or Yehuda (IL)

( * ) Notice: Subject to any disclaimer, the term of this patent is extended or adjusted under 35 U.S.C. 154(b) by 0 days.

(21) Appl. No.: 16/637,166

(22) PCT Filed: Aug. 7, 2018

(86) PCT No.: PCT/IL2018/050869
§ 371 (c)(1),
(2) Date: Feb. 6, 2020

(87) PCT Pub. No.: WO2019/030753
PCT Pub. Date: Feb. 14, 2019

(65) Prior Publication Data
US 2020/0163760 A1    May 28, 2020

Related U.S. Application Data

(63) Continuation-in-part of application No. 15/995,597, filed on Jun. 1, 2018, now Pat. No. 10,098,732, which
(Continued)

(51) Int. Cl.
*A61F 2/24*   (2006.01)
*B23P 15/00*  (2006.01)

(52) U.S. Cl.
CPC .......... *A61F 2/2418* (2013.01); *A61F 2/2412* (2013.01); *A61F 2/2415* (2013.01);
(Continued)

(58) Field of Classification Search
CPC ........ A61F 2/24; A61F 2/2415; A61F 2/2418; A61F 2/2412; A61F 2220/0075; B23P 15/001

See application file for complete search history.

(56) References Cited

U.S. PATENT DOCUMENTS 5,314,473 A    5/1994   Godin
5,954,766 A    9/1999   Zadno-Azizi et al.
(Continued)

FOREIGN PATENT DOCUMENTS

WO    2012/036740    3/2012
WO    2013/021375    2/2013
(Continued)

OTHER PUBLICATIONS

An Invitation to pay additional fees dated Jan. 2, 2018, which issued during the prosecution of Applicant's PCT/IL2017/050849.
(Continued)

*Primary Examiner* — Jason-Dennis N Stewart
(74) *Attorney, Agent, or Firm* — Dilworth IP, LLC

(57) ABSTRACT

A unitary flexible sheet is folded to defines a panel, and first and second tabs. Each of the tabs has an inner layer and an outer layer. Commissural portions of prosthetic leaflets are sandwiched between inner layers of the first and second tabs. The tabs protrude from a first side of the panel, and are shaped such that progressively downstream parts of each tab protrude progressively further away from the panel portion. Other embodiments are also described.

19 Claims, 28 Drawing Sheets

Related U.S. Application Data is a continuation of application No. 15/878,206, filed on Jan. 23, 2018, now Pat. No. 9,987,132, which is a continuation-in-part of application No. PCT/IL2017/050873, filed on Aug. 8, 2017.

(60) Provisional application No. 62/372,861, filed on Aug. 10, 2016.

(52) U.S. Cl.
CPC ........... *B23P 15/001* (2013.01); *A61F 2/2436* (2013.01); *A61F 2210/0014* (2013.01); *A61F 2220/0025* (2013.01); *A61F 2220/0075* (2013.01); *A61F 2230/0069* (2013.01); *A61F 2230/0093* (2013.01); *A61F 2240/001* (2013.01); *A61F 2250/0039* (2013.01); *A61F 2250/0063* (2013.01)

(56) References Cited

U.S. PATENT DOCUMENTS

| | | | |
|---|---|---|---|
| 6,264,700 B1 | 7/2001 | Kilcoyne et al. | |
| 6,458,153 B1 | 10/2002 | Bailey et al. | |
| 6,669,724 B2 | 12/2003 | Park et al. | |
| 6,764,518 B2 | 7/2004 | Godin | |
| 6,767,362 B2 | 7/2004 | Schreck | |
| 7,316,716 B2 | 1/2008 | Egan | |
| 7,442,204 B2 | 10/2008 | Schwammenthal | |
| 7,837,645 B2 | 11/2010 | Bessler et al. | |
| 8,029,557 B2 | 10/2011 | Sobrino-Serrano et al. | |
| 8,038,720 B2 | 10/2011 | Wallace et al. | |
| 8,361,144 B2 | 1/2013 | Fish et al. | |
| 8,474,460 B2 | 7/2013 | Barrett et al. | |
| 8,500,821 B2 | 8/2013 | Sobrino-Serrano et al. | |
| 8,568,475 B2 * | 10/2013 | Nguyen ................ A61F 2/2418 623/2.12 | |
| 8,579,964 B2 | 11/2013 | Lane et al. | |
| 8,591,460 B2 | 11/2013 | Wilson et al. | |
| 8,673,020 B2 | 3/2014 | Sobrino-Serrano et al. | |
| 8,795,357 B2 | 8/2014 | Yohanan et al. | |
| 8,852,272 B2 | 10/2014 | Gross et al. | |
| 8,876,800 B2 | 11/2014 | Behan | |
| 8,906,083 B2 | 12/2014 | Obermiller et al. | |
| 8,998,982 B2 | 4/2015 | Richter et al. | |
| 9,023,100 B2 | 5/2015 | Quadri et al. | |
| 9,050,188 B2 | 6/2015 | Schweich et al. | |
| 9,132,006 B2 | 9/2015 | Spenser et al. | |
| 9,241,791 B2 | 1/2016 | Braido et al. | |
| 9,241,792 B2 | 1/2016 | Benichou et al. | |
| 9,248,014 B2 | 2/2016 | Lane et al. | |
| 9,387,078 B2 | 7/2016 | Gross et al. | |
| 9,427,303 B2 | 8/2016 | Liddy et al. | |
| 9,474,638 B2 | 10/2016 | Robinson et al. | |
| 9,498,314 B2 | 11/2016 | Behan | |
| 9,566,152 B2 | 2/2017 | Schweich et al. | |
| 9,662,203 B2 | 5/2017 | Sheahan et al. | |
| 9,681,952 B2 | 6/2017 | Hacohen et al. | |
| 9,717,591 B2 | 8/2017 | Chau et al. | |
| 9,743,932 B2 | 8/2017 | Amplatz et al. | |
| D800,908 S | 10/2017 | Hariton et al. | |
| 9,987,132 B1 | 6/2018 | Hariton et al. | |
| 10,010,414 B2 | 7/2018 | Cooper et al. | |
| 10,098,732 B1 | 10/2018 | Hariton et al. | |
| 10,226,341 B2 | 3/2019 | Gross et al. | |
| 10,258,471 B2 | 4/2019 | Lutter et al. | |
| 10,321,995 B1 | 6/2019 | Christianson et al. | |
| 10,327,895 B2 | 6/2019 | Lozonschi et al. | |
| 10,531,872 B2 | 1/2020 | Hacohen et al. | |
| 10,548,731 B2 | 2/2020 | Lashinski et al. | |
| 2002/0177894 A1 | 11/2002 | Acosta et al. | |
| 2003/0060875 A1 | 3/2003 | Wittens | |
| 2003/0069635 A1 | 4/2003 | Cartledge et al. | |
| 2004/0133267 A1 | 7/2004 | Lane | |
| 2004/0210304 A1 | 10/2004 | Seguin et al. | |
| 2005/0137690 A1 | 6/2005 | Salahieh et al. | |
| 2005/0240200 A1 | 10/2005 | Bergheim | |
| 2006/0004439 A1 | 1/2006 | Spenser et al. | |
| 2006/0020327 A1 | 1/2006 | Lashinski et al. | |
| 2006/0041189 A1 | 2/2006 | Vancaillie | |
| 2006/0111773 A1 | 5/2006 | Rittgers et al. | |
| 2006/0259137 A1 | 11/2006 | Artof et al. | |
| 2007/0027528 A1 | 2/2007 | Agnew | |
| 2007/0027549 A1 | 2/2007 | Godin | |
| 2007/0219630 A1 | 9/2007 | Chu | |
| 2008/0091261 A1 | 4/2008 | Long et al. | |
| 2008/0200980 A1 | 8/2008 | Robin et al. | |
| 2008/0269879 A1 | 10/2008 | Sathe et al. | |
| 2009/0005863 A1 | 1/2009 | Goetz et al. | |
| 2009/0088836 A1 | 4/2009 | Bishop et al. | |
| 2009/0157175 A1 * | 6/2009 | Benichou ............... A61F 2/2412 623/2.18 | |
| 2009/0240320 A1 | 9/2009 | Tuval et al. | |
| 2009/0259306 A1 | 10/2009 | Rowe | |
| 2009/0276040 A1 | 11/2009 | Rowe et al. | |
| 2010/0023120 A1 * | 1/2010 | Holecek ................ A61F 2/2412 623/2.19 | |
| 2010/0049313 A1 | 2/2010 | Alon et al. | |
| 2010/0161036 A1 | 6/2010 | Pintor et al. | |
| 2011/0004299 A1 | 1/2011 | Navia et al. | |
| 2011/0021985 A1 | 1/2011 | Spargias | |
| 2011/0137397 A1 | 6/2011 | Chau et al. | |
| 2011/0224785 A1 | 9/2011 | Hacohen | |
| 2011/0245911 A1 | 10/2011 | Quill et al. | |
| 2011/0282439 A1 | 11/2011 | Thill et al. | |
| 2011/0313515 A1 | 12/2011 | Quadri et al. | |
| 2011/0319989 A1 | 12/2011 | Lane et al. | |
| 2012/0016468 A1 | 1/2012 | Robin et al. | |
| 2012/0022629 A1 | 1/2012 | Perera et al. | |
| 2012/0053676 A1 | 3/2012 | Ku et al. | |
| 2012/0078353 A1 | 3/2012 | Quadri et al. | |
| 2012/0089223 A1 * | 4/2012 | Nguyen ................. A61F 2/2418 623/2.14 | |
| 2012/0101571 A1 | 4/2012 | Thambar et al. | |
| 2012/0310328 A1 | 12/2012 | Olson et al. | |
| 2013/0018458 A1 | 1/2013 | Yohanan et al. | |
| 2013/0289711 A1 | 10/2013 | Liddy et al. | |
| 2013/0304200 A1 | 11/2013 | McLean et al. | |
| 2014/0000112 A1 | 1/2014 | Braido et al. | |
| 2014/0018915 A1 | 1/2014 | Biadillah et al. | |
| 2014/0207231 A1 | 7/2014 | Hacohen et al. | |
| 2014/0222136 A1 | 8/2014 | Geist et al. | |
| 2014/0222142 A1 | 8/2014 | Kovalsky et al. | |
| 2014/0236287 A1 | 8/2014 | Clague et al. | |
| 2014/0236289 A1 | 8/2014 | Alkhatib | |
| 2014/0257461 A1 | 9/2014 | Robinson et al. | |
| 2014/0257467 A1 | 9/2014 | Lane et al. | |
| 2014/0277409 A1 | 9/2014 | Börtlein et al. | |
| 2014/0277411 A1 | 9/2014 | Börtlein et al. | |
| 2014/0277418 A1 * | 9/2014 | Miller ................... A61F 2/2403 623/2.17 | |
| 2015/0119970 A1 | 4/2015 | Nakayama et al. | |
| 2015/0157458 A1 | 6/2015 | Thambar et al. | |
| 2015/0173896 A1 | 6/2015 | Richter et al. | |
| 2015/0272730 A1 | 10/2015 | Melnick et al. | |
| 2015/0320556 A1 | 11/2015 | Levi et al. | |
| 2015/0327994 A1 | 11/2015 | Morriss et al. | |
| 2015/0328000 A1 | 11/2015 | Ratz et al. | |
| 2015/0351904 A1 | 12/2015 | Cooper et al. | |
| 2015/0359629 A1 | 12/2015 | Ganesan et al. | |
| 2016/0030171 A1 | 2/2016 | Quijano et al. | |
| 2016/0113766 A1 | 4/2016 | Ganesan et al. | |
| 2016/0113768 A1 | 4/2016 | Ganesan et al. | |
| 2016/0270911 A1 | 9/2016 | Ganesan et al. | |
| 2016/0317305 A1 | 11/2016 | Pelled et al. | |
| 2016/0331526 A1 | 11/2016 | Schweich et al. | |
| 2016/0374802 A1 | 12/2016 | Levi et al. | |
| 2017/0042678 A1 | 2/2017 | Ganesan et al. | |
| 2017/0135816 A1 | 5/2017 | Lashinski et al. | |
| 2017/0189174 A1 | 7/2017 | Braido et al. | |
| 2017/0196688 A1 | 7/2017 | Christianson et al. | |
| 2017/0196692 A1 | 7/2017 | Kirk et al. | |
| 2017/0216026 A1 | 8/2017 | Quill et al. | |
| 2017/0231760 A1 | 8/2017 | Lane et al. | |

(56) References Cited

U.S. PATENT DOCUMENTS

| | | |
|---|---|---|
| 2017/0333187 A1 | 11/2017 | Hariton et al. |
| 2017/0367823 A1 | 12/2017 | Hariton et al. |
| 2018/0014930 A1 | 1/2018 | Hariton et al. |
| 2018/0021129 A1 | 1/2018 | Peterson et al. |
| 2018/0153687 A1 | 6/2018 | Hariton et al. |
| 2018/0206983 A1 | 7/2018 | Noe et al. |
| 2018/0250126 A1 | 9/2018 | O'connor et al. |
| 2018/0280136 A1 | 10/2018 | Hariton et al. |
| 2018/0296336 A1 | 10/2018 | Cooper et al. |
| 2018/0353294 A1 | 12/2018 | Calomeni et al. |
| 2019/0053896 A1 | 2/2019 | Adamek-bowers et al. |
| 2019/0060060 A1 | 2/2019 | Chau et al. |
| 2019/0060068 A1 | 2/2019 | Cope et al. |
| 2019/0060070 A1 | 2/2019 | Groothuis et al. |
| 2019/0069997 A1 | 3/2019 | Ratz et al. |
| 2019/0105153 A1 | 4/2019 | Barash et al. |
| 2019/0117391 A1 | 4/2019 | Humair |
| 2019/0175339 A1 | 6/2019 | Vidlund |
| 2019/0183639 A1 | 6/2019 | Moore |
| 2019/0216602 A1 | 7/2019 | Lozonschi |
| 2019/0350701 A1 | 11/2019 | Adamek-bowers et al. |
| 2019/0365530 A1 | 12/2019 | Hoang et al. |
| 2019/0388218 A1 | 12/2019 | Vidlund et al. |
| 2019/0388220 A1 | 12/2019 | Vidlund et al. |
| 2020/0000579 A1 | 1/2020 | Manash et al. |
| 2020/0015964 A1 | 1/2020 | Noe et al. |
| 2020/0060818 A1 | 2/2020 | Geist et al. |

FOREIGN PATENT DOCUMENTS

| | | |
|---|---|---|
| WO | 2013/072496 | 5/2013 |
| WO | 2014/115149 | 7/2014 |
| WO | 2016/016899 | 2/2016 |
| WO | 2016/125160 | 8/2016 |
| WO | 2018/029680 | 2/2018 |
| WO | 2019/030753 | 2/2019 |
| WO | 2019/195860 | 10/2019 |

OTHER PUBLICATIONS

An Office Action dated Dec. 7, 2017, which issued during the prosecution of U.S. Appl. No. 15/213,791.
An Office Action dated Feb. 2, 2018, which issued during the prosecution U.S. Appl. No. 15/329,920.
An Office Action dated Jan. 5, 2018, which issued during the prosecution of U.S. Appl. No. 15/541,783.
An Office Action dated Jan. 17, 2018, which issued during the prosecution of U.S. Appl. No. 14/763,004.
An Office Action dated Oct. 23, 2017, which issued during the prosecution of U.S. Appl. No. 14/763,004.
An Office Action dated Feb. 7, 2018, which issued during the prosecution of U.S. Appl. No. 15/197,069.
An Office Action dated Feb. 8, 2018, which issued during the prosecution of U.S. Appl. No. 15/213,791.
Notice of Allowance dated Apr. 20, 2018, which issued during the prosecution of U.S. Appl. No. 15/878,206.
An Invitation to pay additional fees dated Sep. 29, 2017, which issued during the prosecution of Applicant's PCT/IL2017/050873.
An International Search Report and a Written Opinion both dated Nov. 24, 2017, which issued during the prosecution of Applicant's PCT/IL2017/050873.
An International Preliminary Report on Patentability dated Feb. 12, 2019, which issued during the prosecution of Applicant's PCT/IL2017/050873.
Notice of Allowance dated Aug. 13, 2018, which issued during the prosecution of U.S. Appl. No. 15/995,597.
U.S. Appl. No. 62/372,861, filed Aug. 10, 2016.
An Office Action dated Jan. 6, 2020, which issued during the prosecution of U.S. Appl. No. 16/660,231.
An Office Action dated Dec. 31, 2019, which issued during the prosecution of U.S. Appl. No. 16/183,140.
An Office Action dated Jan. 14, 2020, which issued during the prosecution of U.S. Appl. No. 16/284,331.
Notice of Allowance dated Jan. 13, 2020, which issued during the prosecution of U.S. Appl. No. 15/956,956.
An Office Action dated Jan. 9, 2020, which issued during the prosecution of U.S. Appl. No. 15/600,190.
European Search Report dated Mar. 5, 2020 which issued during the prosecution of Applicant's European App No. 17752184.6.
European Search Report dated Mar. 4, 2020 which issued during the prosecution of Applicant's European App No. 16706913.7.
Notice of Allowance dated Mar. 12, 2020, which issued during the prosecution of U.S. Appl. No. 16/460,313.
An Office Action dated Jan. 3, 2020, which issued during the prosecution of U.S. Appl. No. 16/678,355.
An Office Action dated Feb. 6, 2020, which issued during the prosecution of U.S. Appl. No. 15/668,659.

* cited by examiner

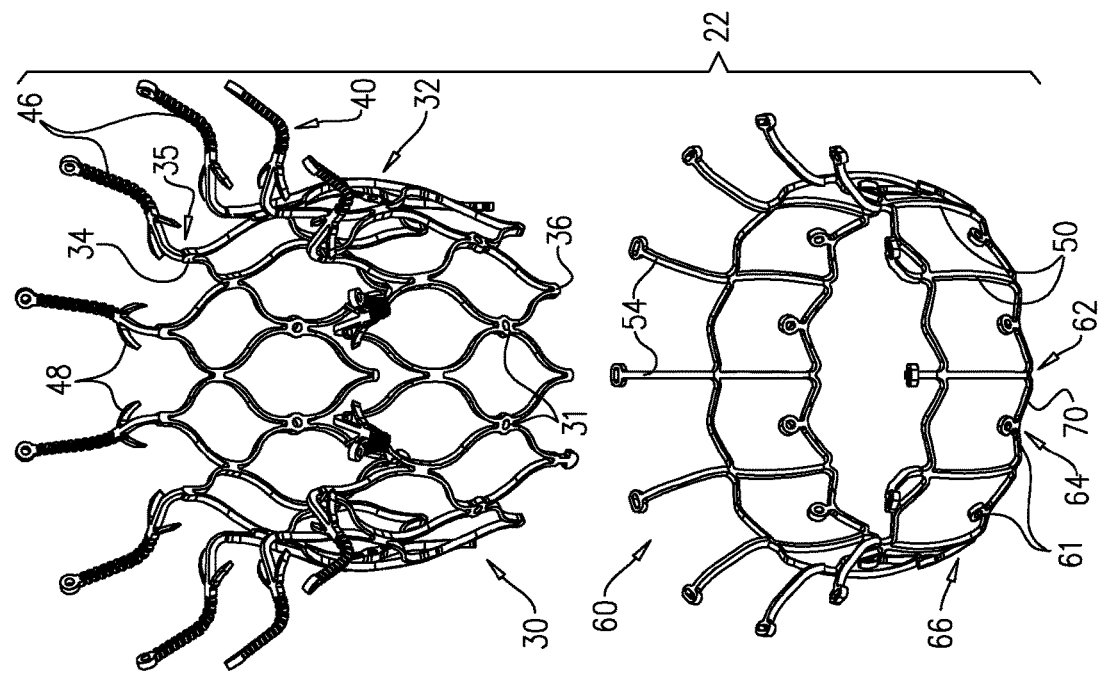
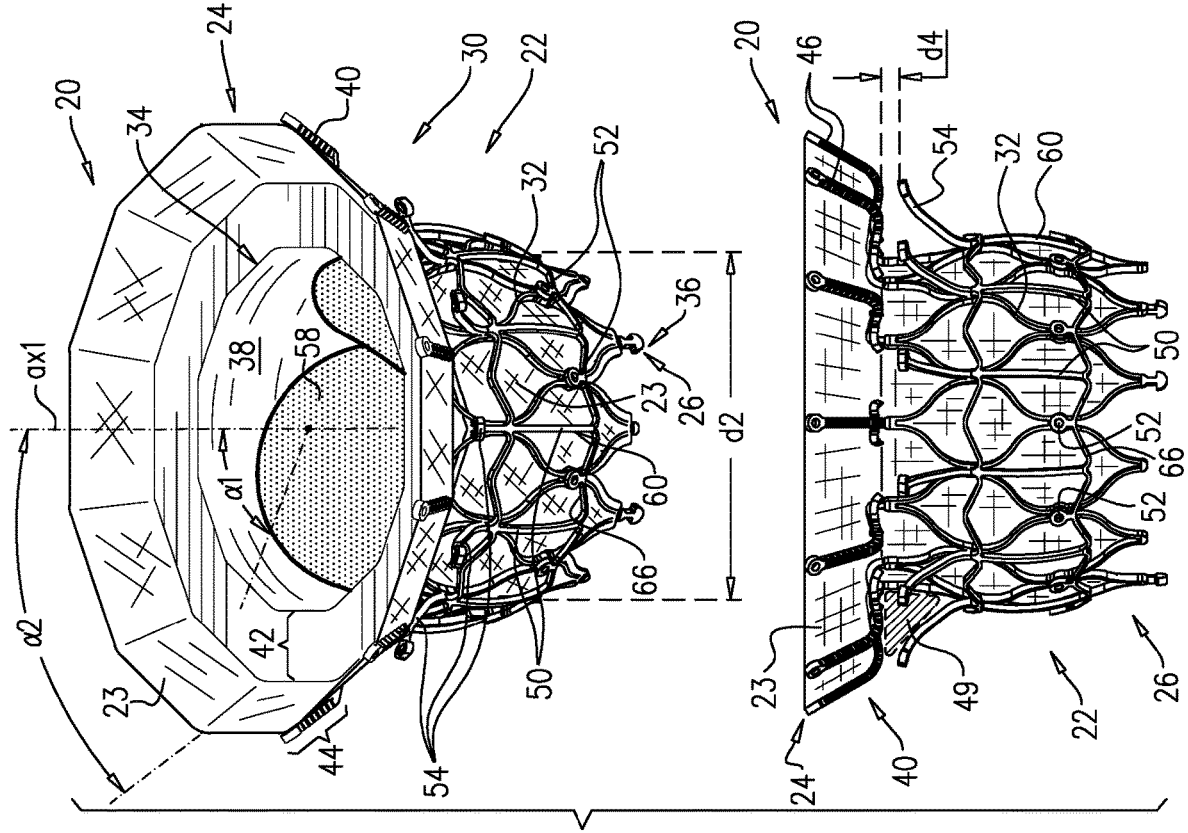
FIG. 1A
FIG. 1B

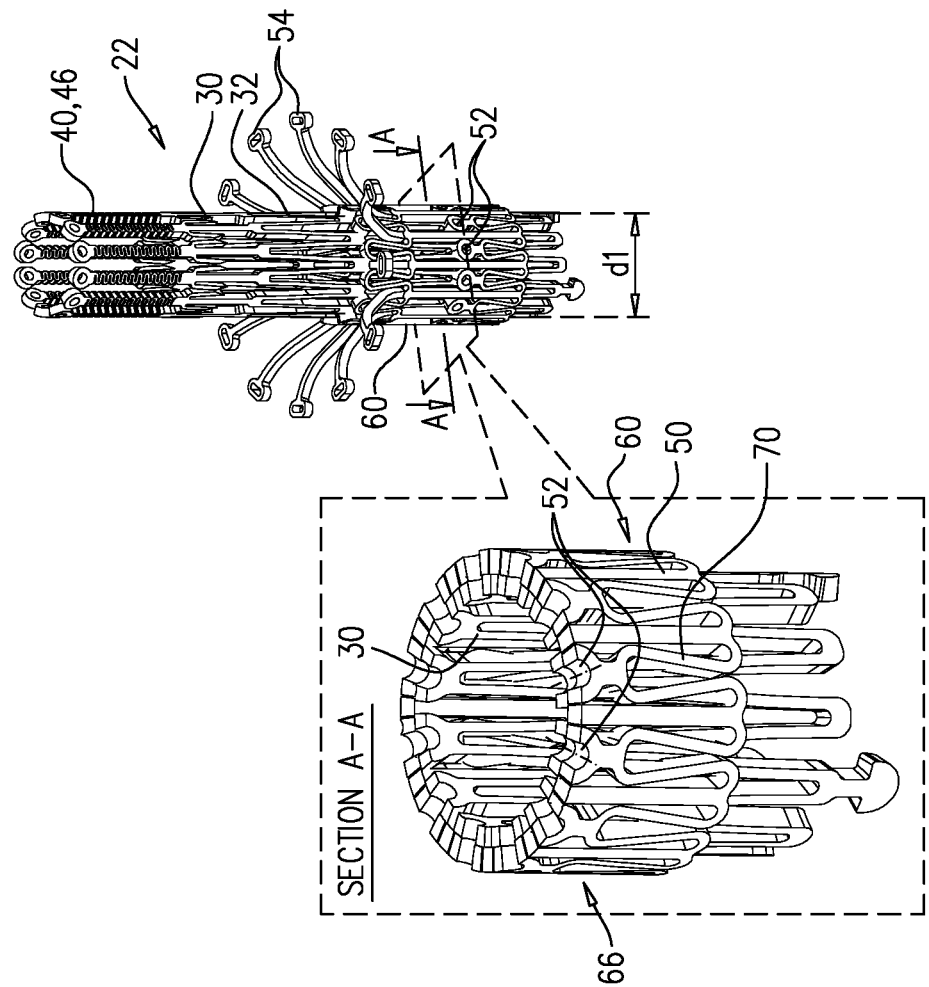
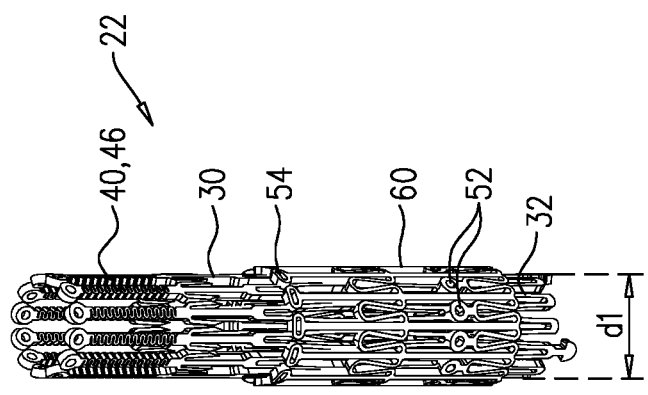

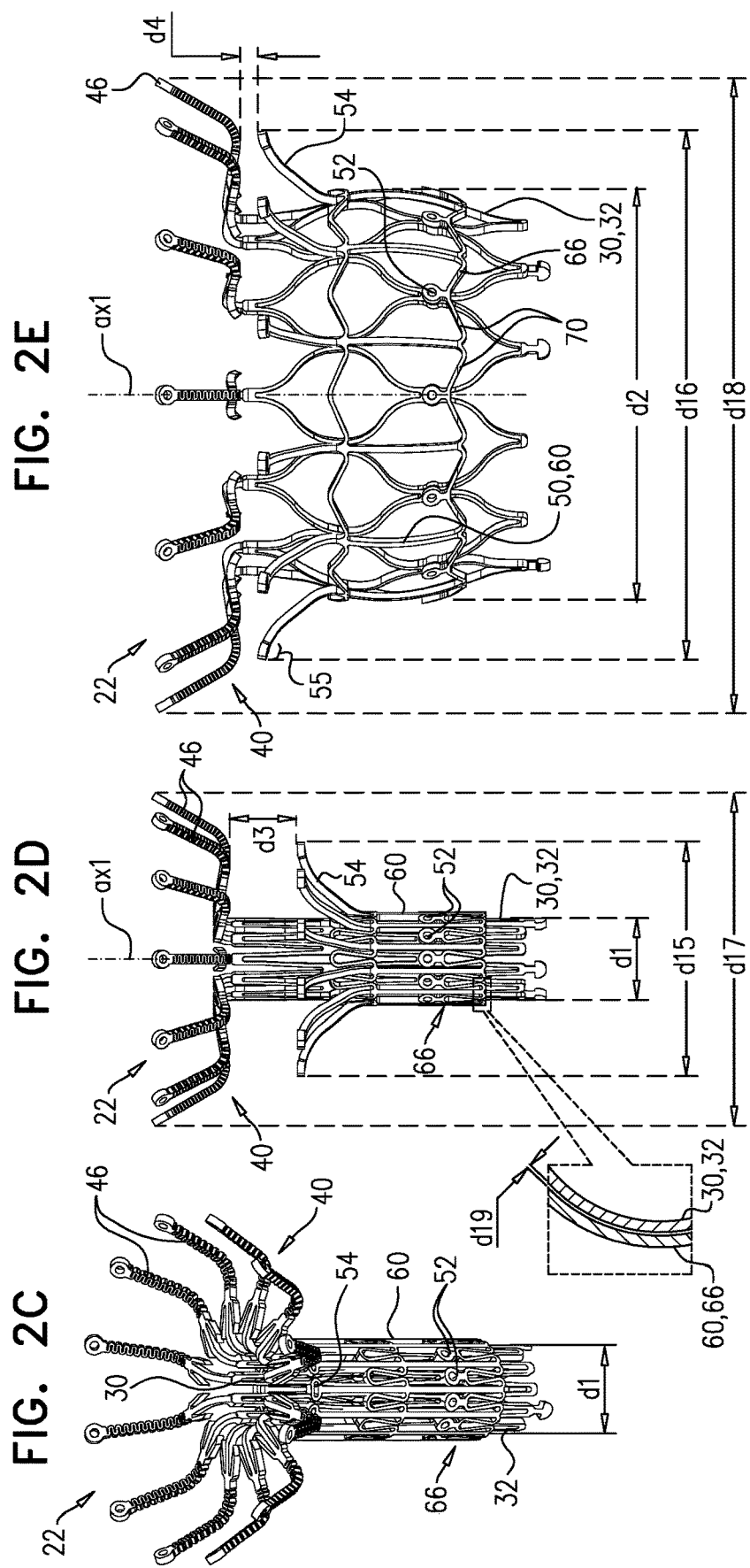

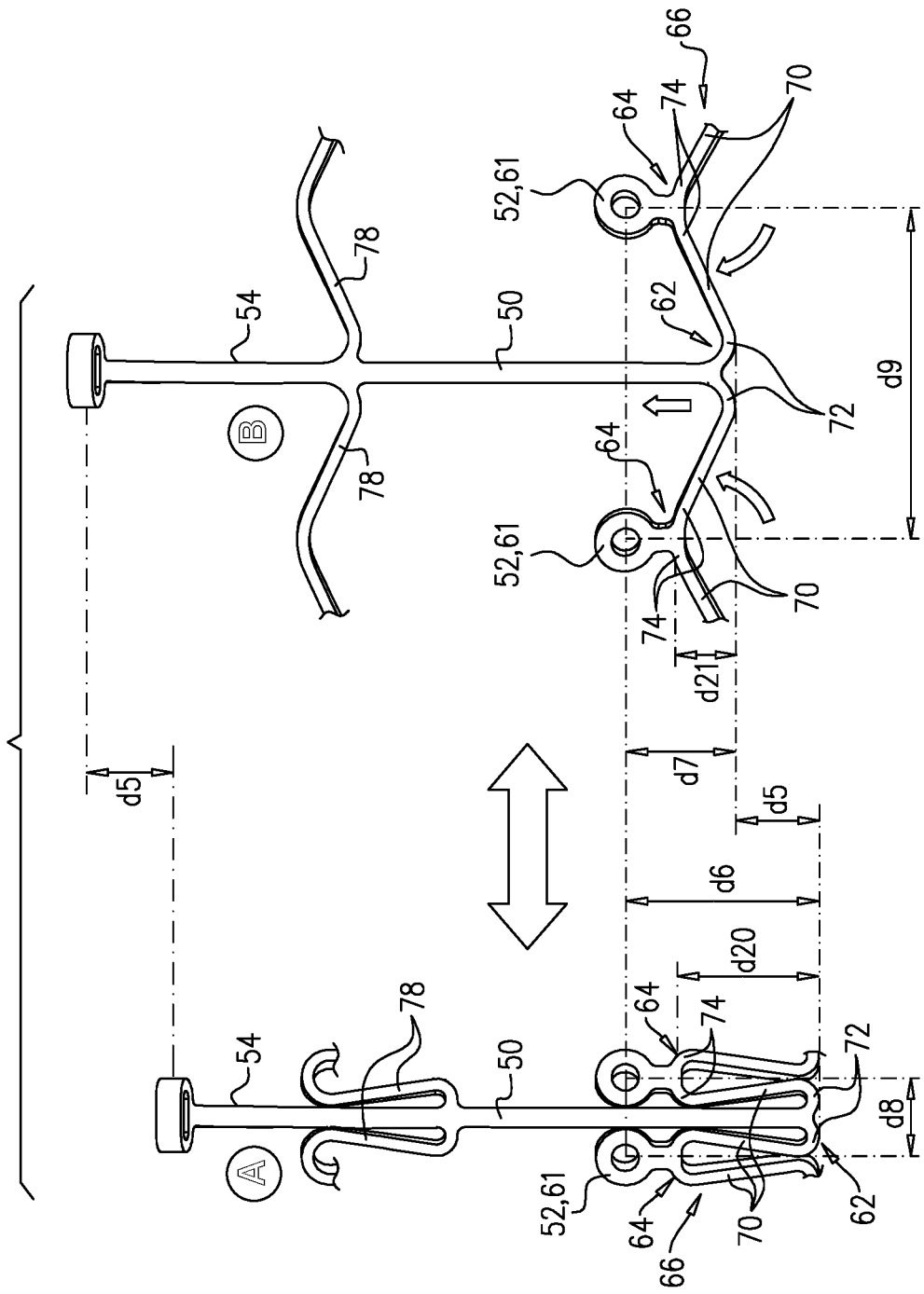

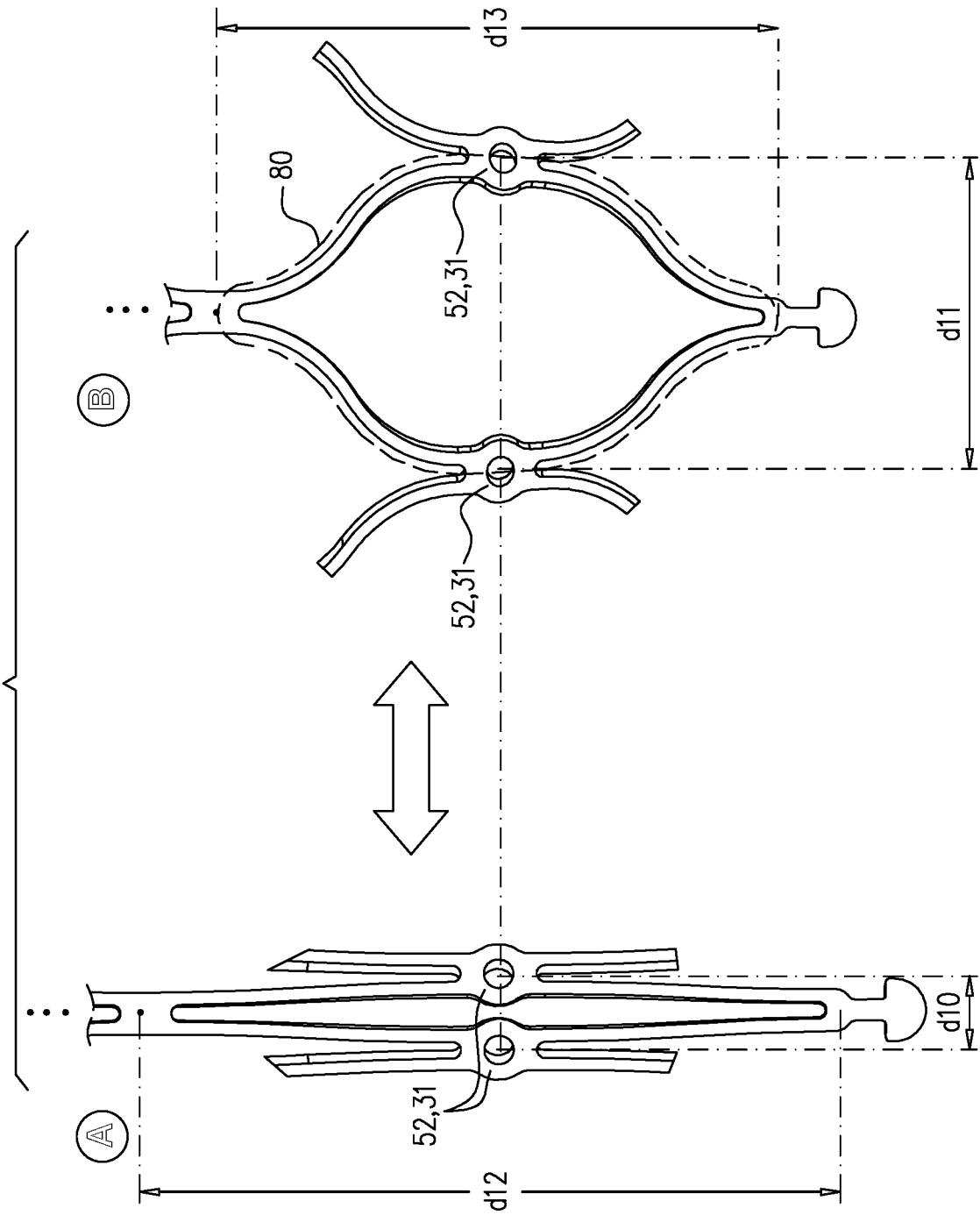

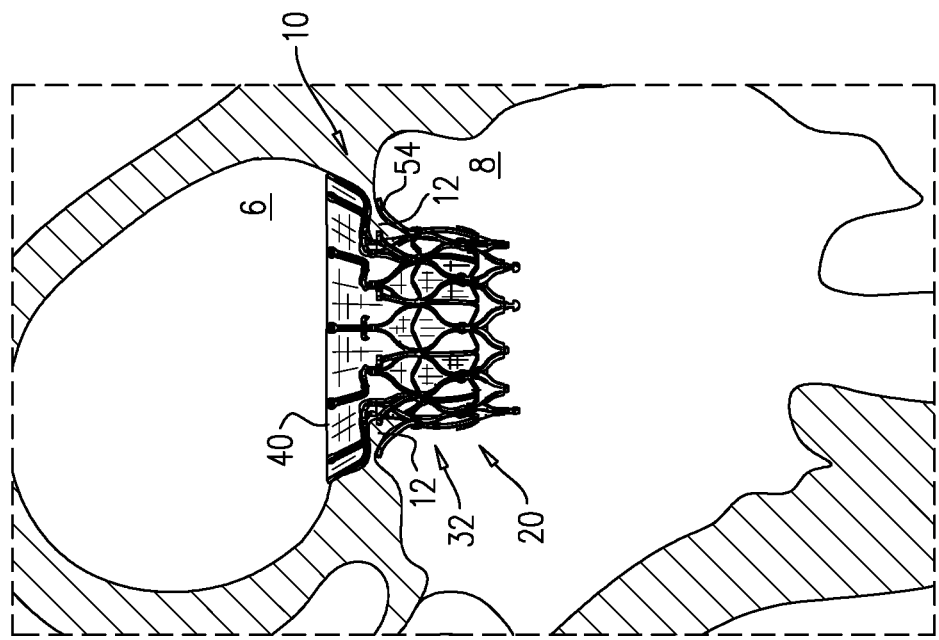
FIG. 4F
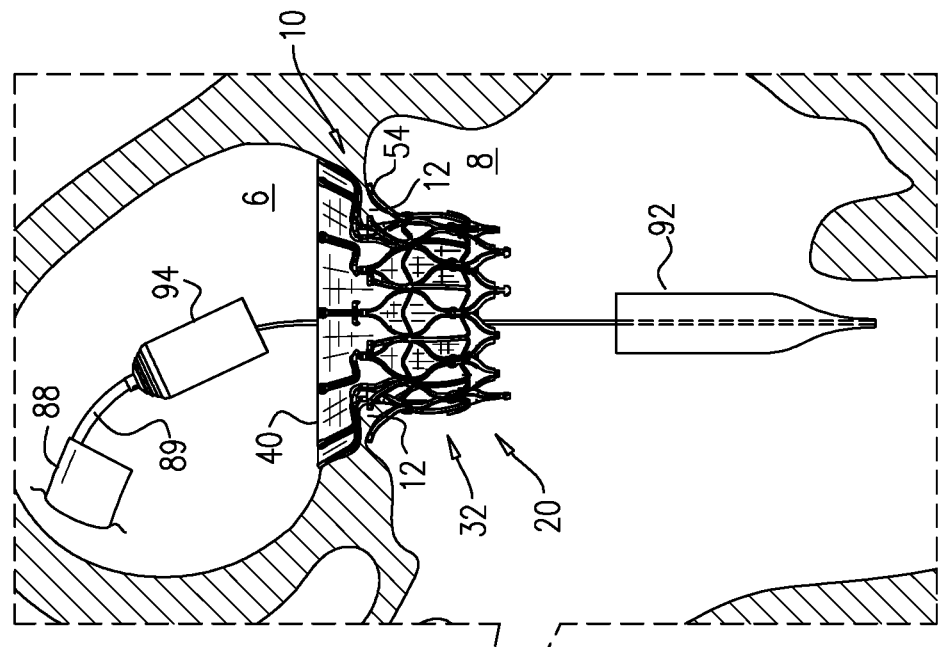
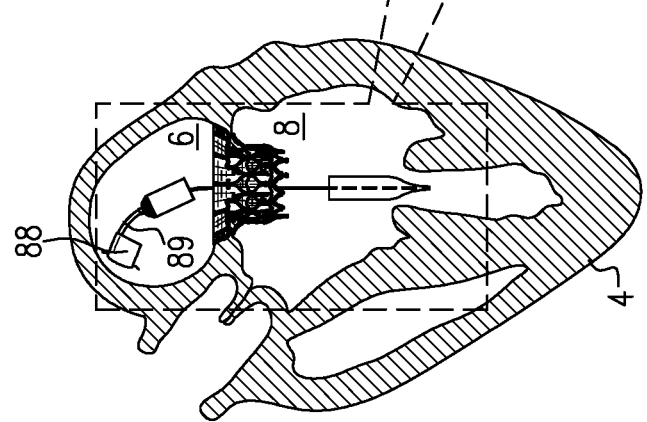
FIG. 4E

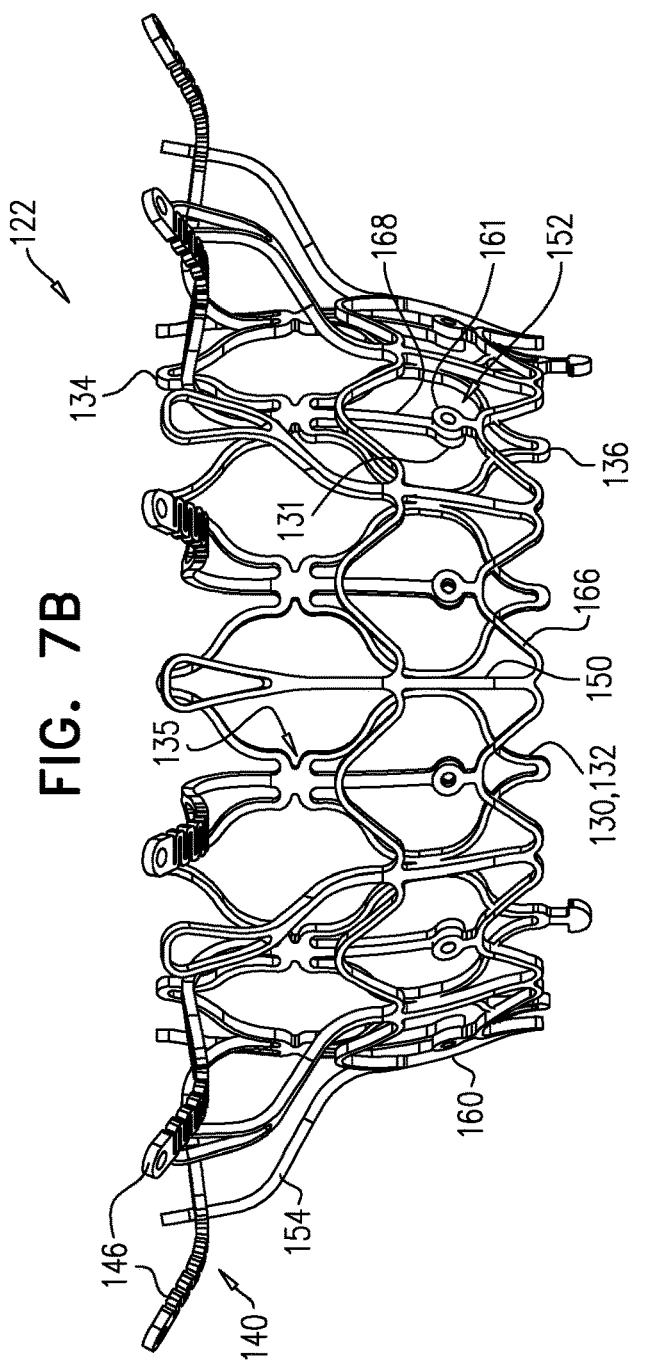
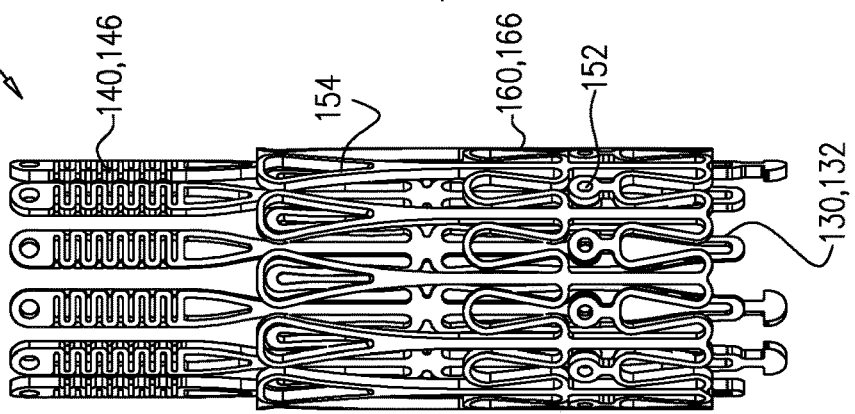
FIG. 7A
FIG. 7B

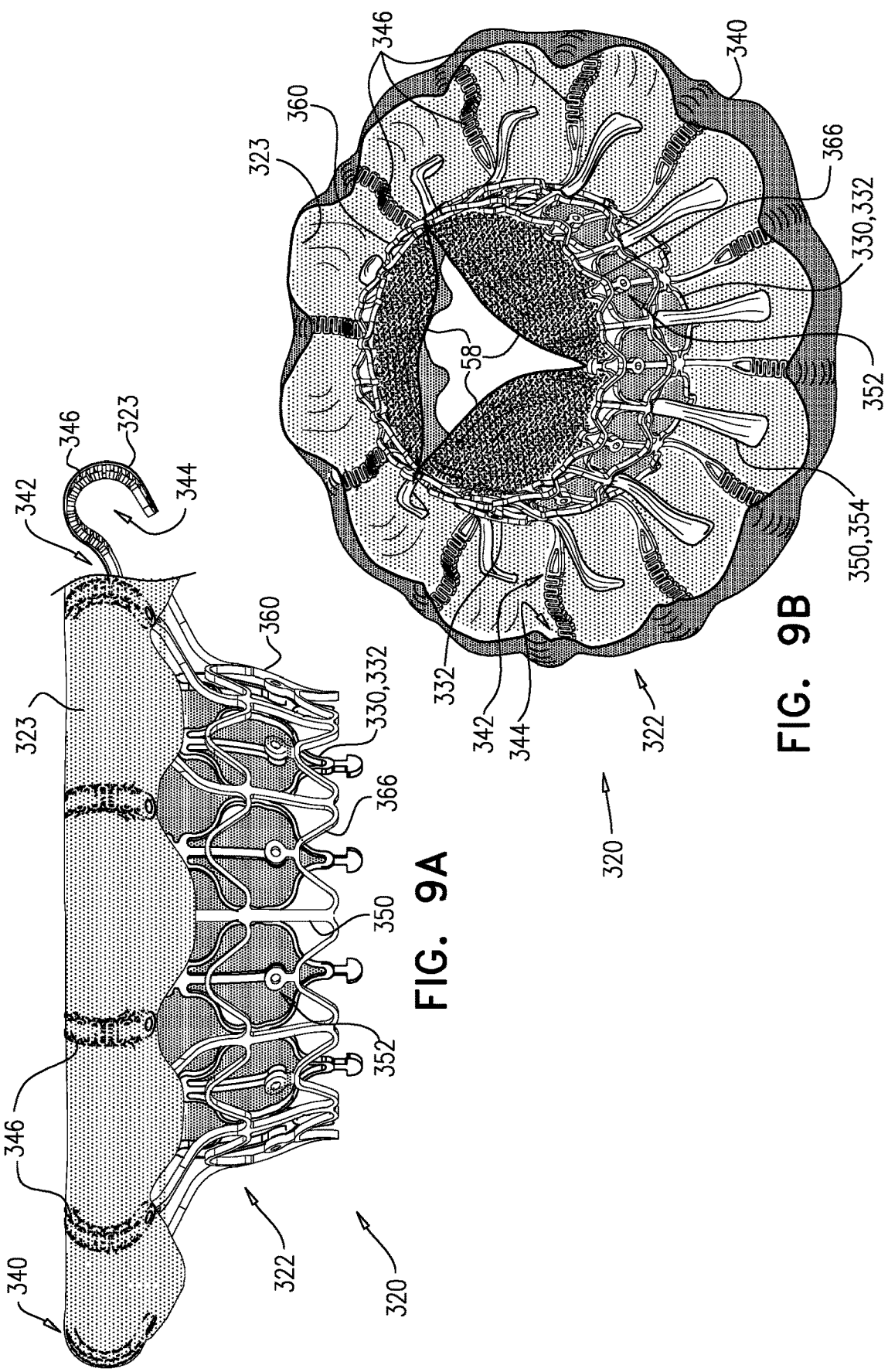

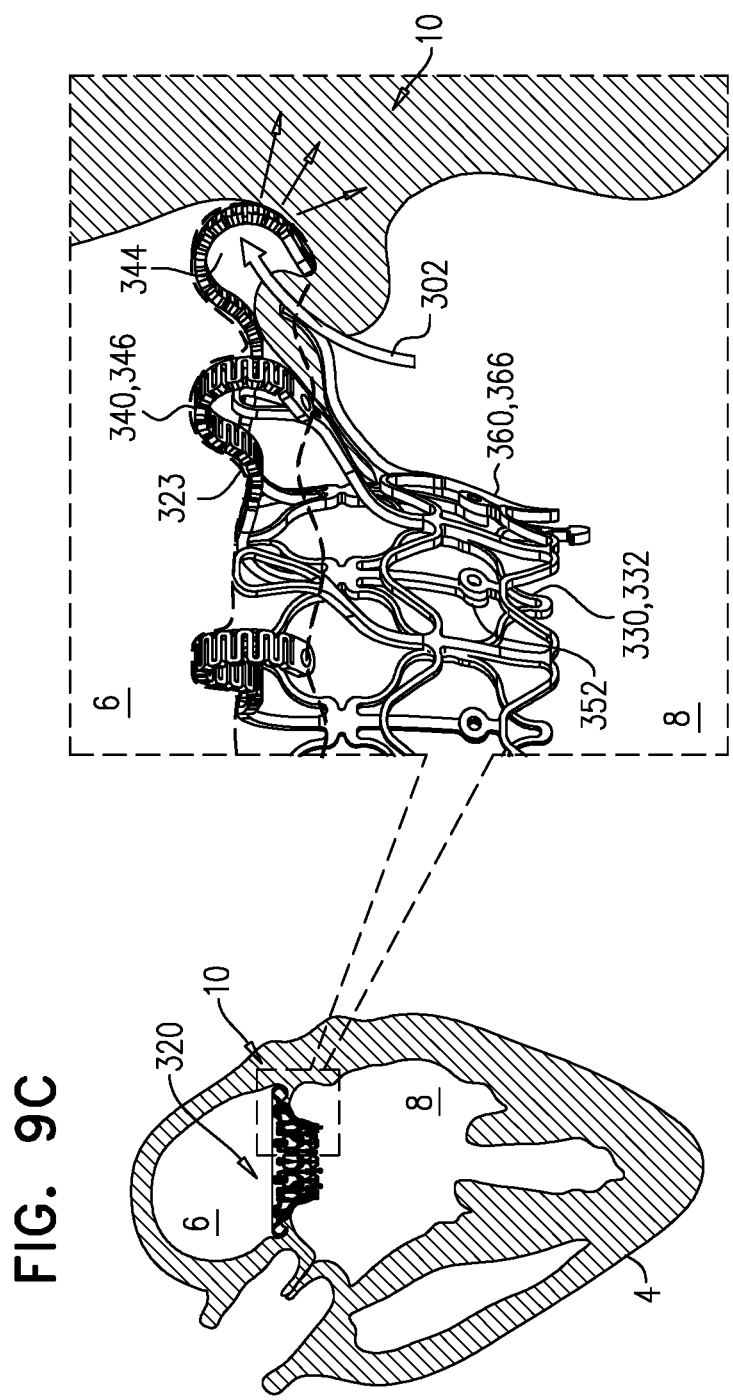

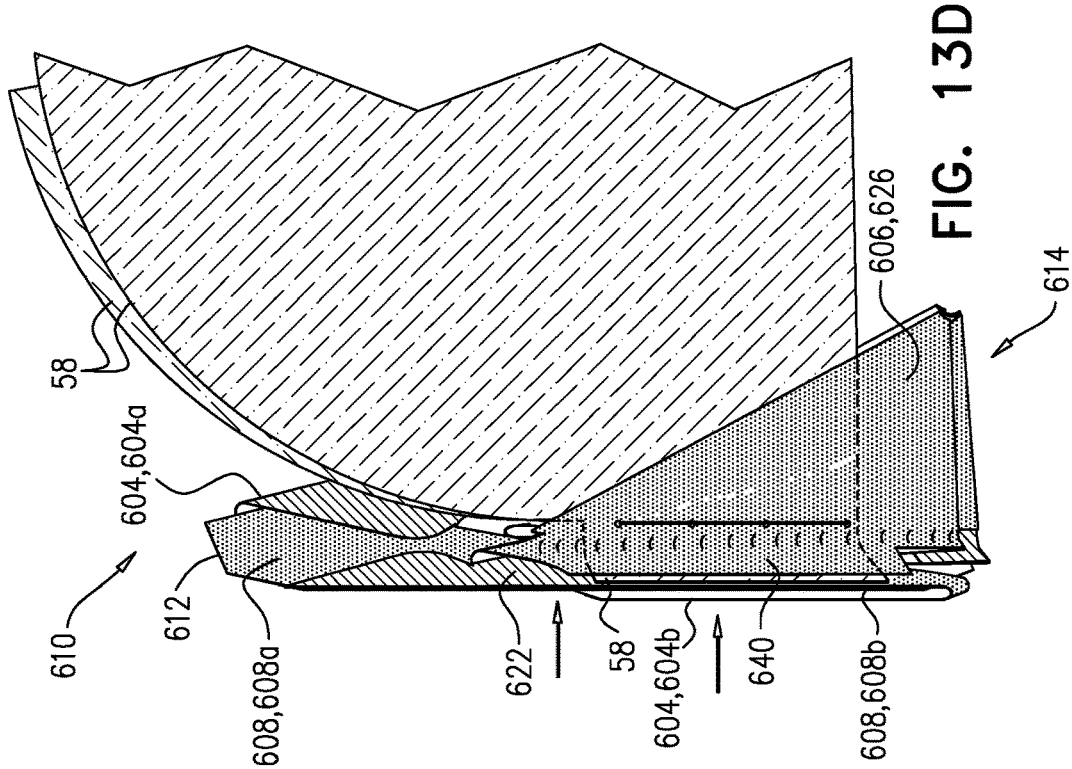
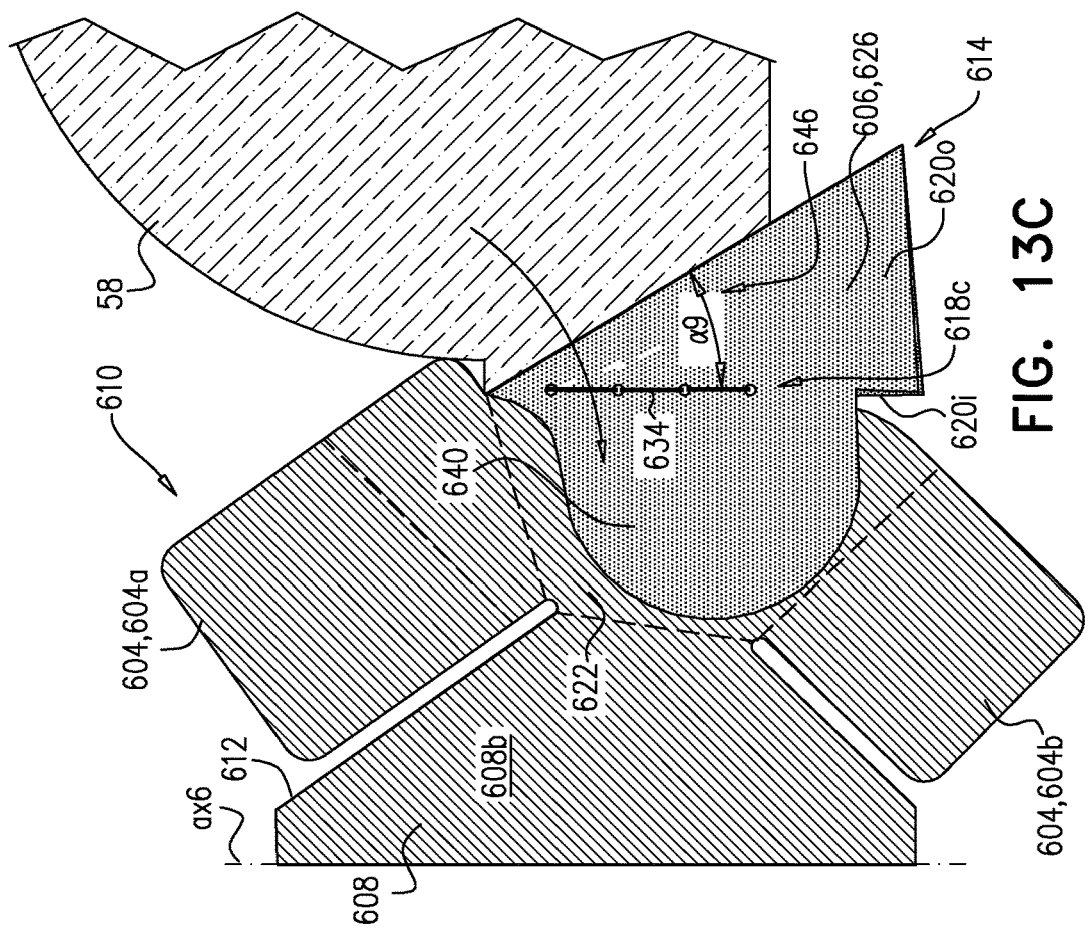

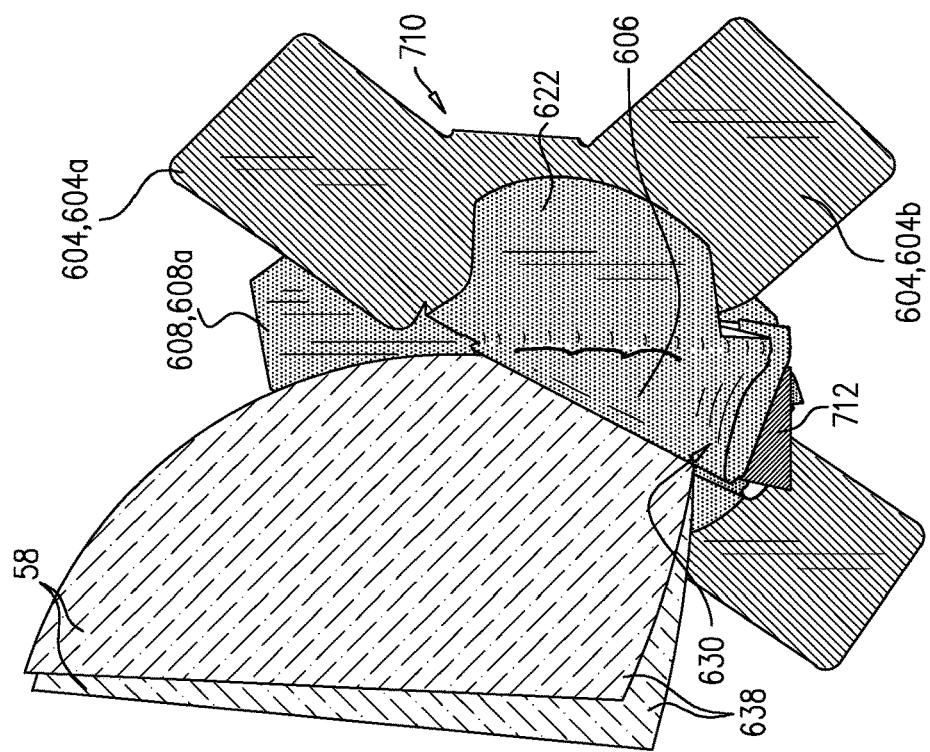
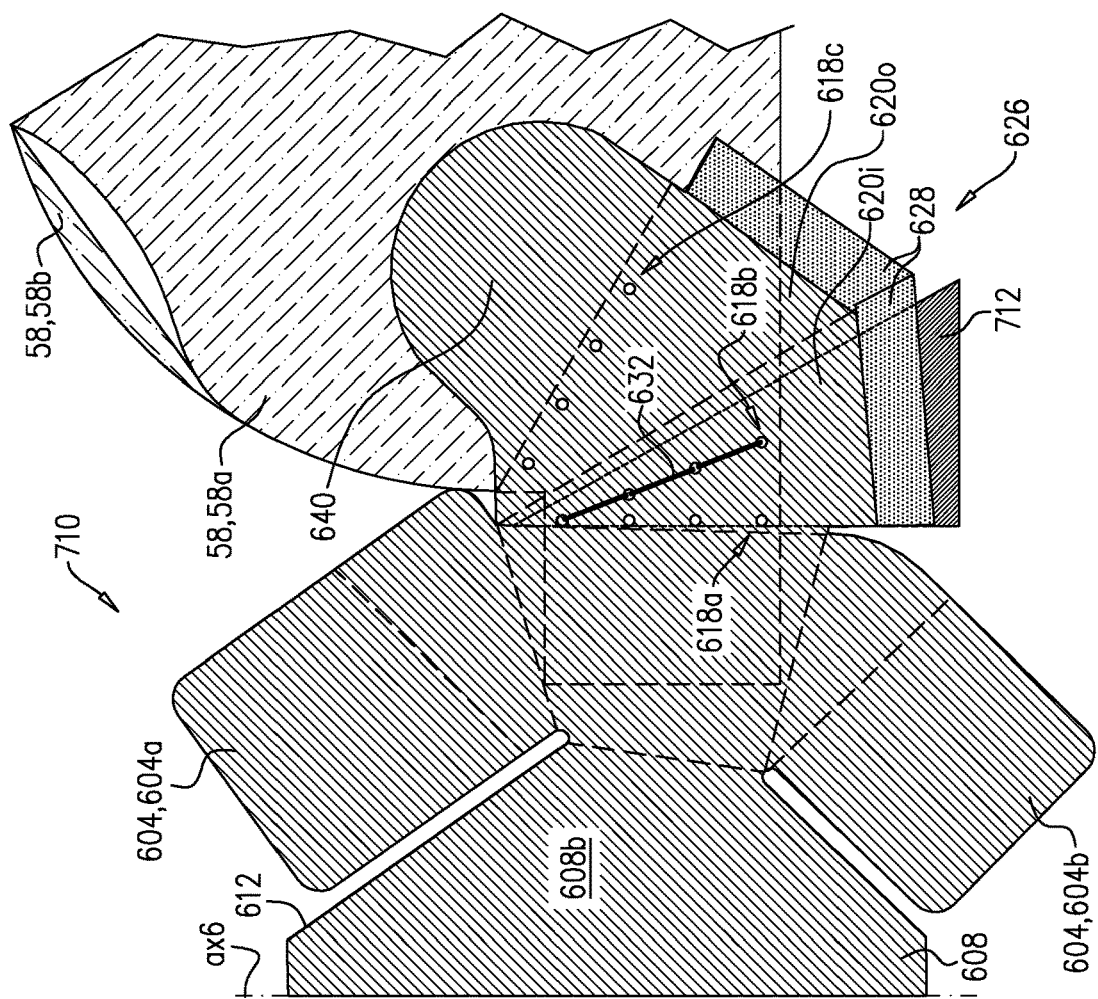
FIG. 14A
FIG. 14B

PROSTHETIC VALVE WITH LEAFLET CONNECTORS

CROSS-REFERENCES TO RELATED APPLICATIONS

The present application is the US National Phase of International Patent Application PCT/IL2018/050869 to Hariton et al., which published as WO 2019/030753, and which:
(1) claims priority to:
  PCT application IL2017/050873 to Hariton et al., filed Aug. 8, 2017, and entitled "Prosthetic valve with concentric frames," which published as WO 2018/029680,
  U.S. patent application Ser. No. 15/878,206 to Hariton et al., filed Jan. 23, 2018, and entitled "Prosthetic valve with leaflet connectors" (now U.S. Pat. No. 9,987,132), and
  U.S. patent application Ser. No. 15/995,597 to Hariton et al., filed Jun. 1, 2018, and entitled "Prosthetic valve with leaflet connectors now U.S. Pat. No. 10,098,732);" and
(2) is a Continuation-in-Part of U.S. patent application Ser. No. 15/995,597 to Hariton et al., filed Jun. 1, 2018, and entitled "Prosthetic valve with leaflet connectors," (now U.S. Pat. No. 10,098,732), which is a Continuation of U.S. patent application Ser. No. 15/878,206 to Hariton et al., filed Jan. 23, 2018, and entitled "Prosthetic valve with leaflet connectors" (now U.S. Pat. No. 9,987,132), which is a Continuation-In-Part of PCT application IL2017/050873 to Hariton et al., filed Aug. 8, 2017, and entitled "Prosthetic valve with concentric frames," which published as WO 2018/029680, and which claims benefit of U.S. provisional patent application 62/372,861 to Hariton et al., filed Aug. 10, 2016, and entitled "Prosthetic valve with concentric frames."

The present application is related to:
  U.S. patent application Ser. No. 15/541,783 (now U.S. Pat. No. 9,974,651), which is the US National Phase of PCT application IL2016/050125 to Hariton et al., filed Feb. 3, 2016, and entitled "Prosthetic valve with axially-sliding frames," which published as WO 2016/125160;
  U.S. patent application Ser. No. 15/668,659 to Hariton et al., filed Aug. 3, 2017, and entitled "Techniques for deployment of a prosthetic valve," which published as US 2017/0333187; and
  U.S. patent application Ser. No. 15/682,789 to Hariton et al., filed Aug. 22, 2017, and entitled "Prosthetic heart valve with compressible frames," which published as US 2017/0367823 (now U.S. Pat. No. 10,449,047).

All of the above applications are incorporated herein by reference.

FIELD OF THE INVENTION

Some applications of the present invention relate in general to valve replacement. More specifically, some applications of the present invention relate to prosthetic valves for replacement of a cardiac valve.

BACKGROUND

Ischemic heart disease causes regurgitation of a heart valve by the combination of ischemic dysfunction of the papillary muscles, and the dilatation of the ventricle that is present in ischemic heart disease, with the subsequent displacement of the papillary muscles and the dilatation of the valve annulus.

Dilation of the annulus of the valve prevents the valve leaflets from fully coapting when the valve is closed. Regurgitation of blood from the ventricle into the atrium results in increased total stroke volume and decreased cardiac output, and ultimate weakening of the ventricle secondary to a volume overload and a pressure overload of the atrium.

SUMMARY OF THE INVENTION

For some applications, an implant is provided having a tubular portion, an upstream support portion and one or more flanges. The implant is assembled from two concentric frames. An inner frame defines the tubular portion and the upstream support portion, and an outer frame defines the flanges. The implant is percutaneously deliverable to a native heart valve in a compressed state, and is expandable at the native valve. The implant is secured at a native heart valve by sandwiching tissue of the native valve between the upstream support portion and the flanges.

For some applications, the outer frame is radially thicker than the inner frame. For some applications, the outer frame is undersized with respect to the inner frame, such that it constrains the inner frame even in a relaxed expanded state of the implant, and such that even in the relaxed expanded state residual stress is present in one or both of the frames. For some applications, a toroidal space is defined by the tubular portion, the upstream support portion, and the flanges. For some such applications, the implant is configured such that the toroidal space is dimensioned proportionally to dimensions of the tubular portion.

For some applications, prosthetic leaflets are secured within a prosthetic valve via connectors, each connector comprising a unitary flexible sheet folded to define a panel, and leaflet-engaging tabs between which commissural portions of the prosthetic leaflets are secured. Typically, the unitary flexible sheet is folded to also define other features, such as flaps that facilitate coupling of the connector to the frame of the prosthetic valve.

There is therefore provided, in accordance with an application of the present invention, a method for use with a flexible sheet that, in an unfolded state of the sheet, defines a panel at a medial region of the sheet, a first tab portion disposed peripherally to the panel, and a second tab portion disposed peripherally to the panel opposite the first tab portion, the method including:
  sandwiching, between the first tab portion and the second tab portion, (i) a first commissural portion of a first prosthetic leaflet, and (ii) a second commissural portion of a second prosthetic leaflet;
  attaching the first tab portion and the second tab portion to the flexible sheet by stitching a first stitching through the first tab-portion, the first commissural portion, the second commissural portion, and the second tab-portion;
  subsequently, covering the first stitching by:
    folding the first tab portion back against itself to form the first tab portion into a first tab having first-tab outer layer and a first-tab inner layer, such that the first-tab inner layer is sandwiched between the first-tab outer layer and the first commissural portion, and
    folding the second tab portion back against itself to form the second tab portion into a second tab having a second-tab outer layer and a second-tab inner layer, such that the second-tab inner layer is sandwiched between the second-tab outer layer and the second commissural portion; and subsequently, stitching a second stitching through the first-tab outer layer, the first-tab inner layer, the first commissural portion, the second commissural portion, the second-tab inner layer, and the second-tab outer layer.

In an application, the step of sandwiching includes sandwiching a separate flexible sheet between the first commissural portion and the second commissural portion.

In an application, stitching the first stitching includes stitching the first stitching through (i) the first tab-portion, (ii) the first commissural portion, (iii) a separate flexible sheet disposed between the first commissural portion and the second commissural portion, (iv) the second commissural portion, and (v) the second tab-portion.

In an application, the step of sandwiching includes sandwiching a fabric divider between the first tab portion and the second tab portion.

In an application, the step of sandwiching includes sandwiching a separate flexible sheet between the first commissural portion and the second commissural portion, and stitching the first stitching includes stitching the first stitching through the separate flexible sheet.

In an application, stitching the second stitching includes stitching the second stitching through the separate flexible sheet.

In an application, the flexible sheet is a first flexible sheet, and the steps of sandwiching, attaching, covering, and stitching the second stitching, are steps in assembling the first flexible sheet into a first commissure at which the first prosthetic leaflet and the second prosthetic leaflet meet, and the method further includes:

assembling a valvular assembly that includes the first commissure, a second commissure, a third commissure, the first prosthetic leaflet, the second prosthetic leaflet, and a third prosthetic leaflet, by:

assembling a second flexible sheet into a second commissure at which the second prosthetic leaflet and a third prosthetic leaflet meet; and assembling a third flexible sheet into a third commissure at which the third prosthetic leaflet and the first prosthetic leaflet meet; and subsequently to assembling the valvular assembly, securing the valvular assembly within a lumen defined by a tubular frame, such that:

the first, second, and third prosthetic leaflets are arranged within the lumen to facilitate upstream-to-downstream fluid flow through the lumen by the first, second, and third prosthetic leaflets opening, and to inhibit downstream-to-upstream fluid flow through the lumen by the first, second, and third prosthetic leaflets closing, and for each of the commissures:
the panel is disposed against an inner surface of the tubular frame, and
the first tab and the second tab extend away from the panel into the lumen.

In an application, for each of the commissures, assembling the flexible sheet into the commissure includes assembling the flexible sheet into the commissure such that the first tab and the second tab each define a loose region, radially inward from the first stitching and the second stitching, that is loose with respect to the prosthetic leaflets that meet at the commissure.

In an application, securing the valvular assembly within the lumen includes securing the valvular assembly within the lumen such that, for each of the commissures, in response to the first, second, and third prosthetic leaflets opening, at least part of the first tab and at least part of the second tab move away from each other, and in response to the first, second, and third prosthetic leaflets closing, at least part of the first tab and at least part of the second tab move toward each other.

In an application, the method further includes, subsequently to stitching the second stitching, securing the panel against an inner surface of a tubular frame, such that (i) the first tab, the second tab, the first prosthetic leaflet, and the second prosthetic leaflet extend away from the panel into a lumen defined by the tubular frame, and (ii) the first and second leaflets are arranged to facilitate upstream-to-downstream fluid flow through the lumen, and to inhibit downstream-to-upstream fluid flow through the lumen.

In an application, the sheet, in its unfolded state, further defines a plurality of flaps disposed peripherally to the panel, and securing the panel against the inner surface of the tubular frame includes folding each flap of the plurality of flaps around a respective component of the tubular frame.

In an application, securing the panel against the inner surface of the tubular frame further includes stitching each flap of the plurality of flaps to the respective component of the tubular frame.

In an application, the method further includes (i) forming a first cushion by folding a first-tab fold in a downstream edge of the first tab portion, and (ii) forming a second cushion by folding a second-tab fold in a downstream edge of the second tab portion.

In an application, forming the first cushion and forming the second cushion include forming the first cushion and forming the second cushion such that, after the panel has been secured against the inner surface of the inner frame, the first cushion and the second cushion are disposed downstream of the first prosthetic leaflet and the second prosthetic leaflet.

In an application, forming the first cushion and forming the second cushion include forming the first cushion and forming the second cushion such that, after the panel has been secured against the inner surface of the inner frame, neither the first cushion nor the second cushion is in contact with the first prosthetic leaflet or the second prosthetic leaflet.

In an application, forming the first cushion includes forming the first cushion such that, after the panel has been secured against the inner surface of the inner frame, the first tab defines a downstream opening between the first-tab inner layer and the first-tab outer layer, and forming the second cushion includes forming the second cushion such that, after the panel has been secured against the inner surface of the inner frame, the second tab portion defines a downstream opening between the second-tab inner layer and the second-tab outer layer.

In an application:
forming the first cushion includes folding the first-tab fold such that, after the panel has been secured against the inner surface of the inner frame, the first-tab fold is disposed between the first-tab inner layer and the first-tab outer layer, and forming the second cushion includes folding the second-tab fold such that, after the panel has been secured against the inner surface of the inner frame, the second-tab fold is disposed between the second-tab inner layer and the second-tab outer layer.

In an application:
the first-tab fold is a first-tab outer fold,
the second-tab fold is a second-tab outer fold, forming the first cushion further includes folding a first-tab inner fold in the downstream edge of the first tab portion, such that after the panel has been secured against the inner surface of the inner frame:

the first-tab outer fold is continuous with the first-tab outer layer, and is disposed between the first-tab outer layer and the first-tab inner fold, and the first-tab inner fold is continuous with the first-tab inner layer, and is disposed between the first-tab inner layer and the first-tab outer fold, and forming the second cushion further includes folding a second-tab inner fold in the downstream edge of the second tab portion, such that after the panel has been secured against the inner surface of the inner frame:

the second-tab outer fold is continuous with the second-tab outer layer, and is disposed between the second-tab outer layer and the second-tab inner fold, and the second-tab inner fold is continuous with the second-tab inner layer, and is disposed between the second-tab inner layer and the second-tab outer fold.

In an application, forming the first-tab cushion includes forming the first-tab cushion prior to folding the first tab-portion back against itself, and forming the second-tab cushion includes forming the second-tab cushion prior to folding the second tab-portion back against itself.

In an application, forming the first-tab cushion and forming the second-tab cushion includes forming the first-tab cushion and forming the second-tab cushion subsequently to stitching the first stitching.

In an application:

the first tab portion defines a plurality of first-tab portion suture holes arranged in:

a first row, a second row, and a third row, and the second tab portion defines a plurality of second-tab portion suture holes arranged in:

a fourth row, a fifth row, and a sixth row, and stitching the first stitching through the first tab-portion, the first commissural portion, the second commissural portion, and the second tab-portion includes stitching the first stitching through the second row, the first commissural portion, the second commissural portion, and the fifth row.

In an application, in the unfolded state of the sheet, the first row and the third row diverge at a diverging angle, and folding the first tab portion back against itself includes folding the first tab portion along a fold line such that an angle between the fold line and the first row is substantially equal to an angle between the fold line and the third row.

In an application, folding the first tab portion back against itself includes folding the first tab portion such that an angle between the fold line and the second row is smaller than both (i) the angle between the fold line and the first row, and (ii) the angle between the fold line and the third row.

In an application:

folding the first tab portion back against itself includes folding the first tab portion back against itself such that the first-tab outer layer covers the second row, and the third row is aligned with the first row, and folding the second tab portion back against itself includes folding the second tab portion back against itself such that the second-tab outer layer covers the fifth row, and the sixth row is aligned with the fourth row.

In an application, stitching the second stitching through the first-tab outer layer, the first-tab inner layer, the first commissural portion, the second commissural portion, the second-tab inner layer, and the second-tab outer layer includes stitching the second stitching through the third row, the first row, the first commissural portion, the second commissural portion, the fourth row, and the sixth row.

In an application, the method further includes, subsequently to stitching the second stitching, bringing the panel closer to the first prosthetic leaflet and the second prosthetic leaflet.

In an application, bringing the panel closer includes moving an unstitched part of the first commissural portion away from an unstitched part of the second commissural portion.

In an application, bringing the panel closer includes sandwiching unstitched parts of the first commissural portion and unstitched parts of the second commissural portion between the panel and another region of the sheet.

In an application, bringing the panel closer to the first prosthetic leaflet and the second prosthetic leaflet includes flattening the panel.

In an application, the step of sandwiching includes bending the panel.

There is further provided, in accordance with an application of the present invention, apparatus, including:

a unitary flexible sheet, folded to define:

a panel, defining a plane, and having a first side facing in a first direction away from the plane, and a second side that is opposite the first side;

a first tab, disposed on the first side of the panel, and protruding in the first direction away from the panel; and a second tab, disposed on the first side of the panel, and protruding in the first direction away from the panel;

a first prosthetic leaflet having a first-leaflet commissural portion disposed between the first tab and the second tab;

a second prosthetic leaflet having a second-leaflet commissural portion disposed between the first tab and the second tab;

and:

at the first tab, the sheet is folded to define a first cushion at a downstream edge of the first tab, the first cushion being configured and positioned to inhibit deflection of a downstream portion of the first prosthetic leaflet away from the second prosthetic leaflet and toward the plane, and at the second tab, the sheet is folded to define a second cushion at a downstream edge of the second tab, the second cushion being configured and positioned to inhibit deflection of a downstream portion of the second prosthetic leaflet away from the first prosthetic leaflet and toward the plane.

In an application, the apparatus further includes a separate flexible sheet, sandwiched between the first-leaflet commissural portion and the second-leaflet commissural portion.

In an application, the first cushion and the second cushion are disposed downstream of the first prosthetic leaflet and the second prosthetic leaflet.

In an application:

the sheet is folded such that the first tab has a first-tab outer layer and a first-tab inner layer, and the second tab has a second-tab outer layer and a second-tab inner layer, the first-leaflet commissural portion is disposed between the first-tab inner layer and the second-tab inner layer, and the second-leaflet commissural portion is disposed between the first-tab inner layer and the second-tab inner layer.

In an application, the first tab defines a downstream opening between the first-tab inner layer and the first-tab outer layer, and the second tab portion defines a downstream opening between the second-tab inner layer and the second-tab outer layer.

In an application:
the sheet defines a first-tab fold and a second-tab fold,
the first cushion includes the first-tab fold, folded between the first-tab inner layer and the first-tab outer layer, and
the second cushion includes the second-tab fold, folded between the second-tab inner layer and the second-tab outer layer.

In an application, the first-tab fold is secured by stitching, and the second-tab fold is secured by stitching.

In an application:
the first-tab fold is a first-tab outer fold, continuous with the first-tab outer layer,
the second-tab fold is a second-tab outer fold, continuous with the second-tab outer layer,
the sheet further defines:
a first-tab inner fold, continuous with the first-tab inner layer, and
a second-tab inner fold, continuous with the second-tab inner layer, the first cushion includes:
the first-tab outer fold, folded between the first-tab outer layer and the first-tab inner fold, and
the first-tab inner fold, folded between the first-tab inner layer and the first-tab outer fold, and
the second cushion includes:
the second-tab outer fold, folded between the second-tab outer layer and the second-tab inner fold, and
the second-tab inner fold, folded between the second-tab inner layer and the second-tab outer fold.

There is further provided, in accordance with an application of the present invention, apparatus, including:
a unitary flexible sheet, folded to define:
a panel, having a first side facing in a first direction, and a second side that is opposite the first side;
a first tab, disposed on the first side of the panel, having a first-tab outer layer and a first-tab inner layer, and protruding in the first direction away from the panel; and
a second tab, disposed on the first side of the panel, having a second-tab outer layer and a second-tab inner layer, and protruding in the first direction away from the panel;
a first prosthetic leaflet having a first-leaflet commissural portion disposed between the first-tab inner layer and the second-tab inner layer;
a second prosthetic leaflet having a second-leaflet commissural portion disposed between the first-tab inner layer and the second-tab inner layer;
a first stitching, stitched through the first-tab inner layer, the first-leaflet commissural portion, the second-leaflet commissural portion, and the second-tab inner layer; and
a second stitching, stitched through the first-tab outer layer, the first-tab inner layer, the first-leaflet commissural portion, the second-leaflet commissural portion, the second-tab inner layer, and the second-tab outer layer,
and the first-tab outer layer and the second-tab outer layer cover the first stitching.

In an application, the apparatus further includes an adhesive disposed on at least one stitching selected from the group consisting of: the first stitching, and the second stitching.

In an application:
the sheet is folded along a first-tab fold line to define the first-tab outer layer and the first-tab inner layer, and the first-tab fold line is closer to the first stitching than to the second stitching, and
the sheet is folded along a second-tab fold line to define the second-tab outer layer and the second-tab inner layer, and the second-tab fold line is closer to the first stitching than to the second stitching.

In an application:
the sheet is folded along a first-tab fold line to define the first-tab outer layer and the first-tab inner layer, and an angle between the first-tab fold line and the first stitching is smaller than an angle between the first-tab fold line and the second stitching, and
the sheet is folded along a second-tab fold line to define the second-tab outer layer and the second-tab inner layer, and an angle between the second-tab fold line and the first stitching is smaller than an angle between the second-tab fold line and the second stitching.

In an application, the apparatus further includes a separate flexible sheet, sandwiched between the first-leaflet commissural portion and the second-leaflet commissural portion.

In an application, the apparatus further includes a tubular frame that defines a lumen, and:
the panel is disposed against an inner surface of the tubular frame, and
the first prosthetic leaflet and the second prosthetic leaflet are secured within the lumen by the flexible sheet being connected to the tubular frame.

In an application, the apparatus further includes a separate flexible sheet, disposed between the first-leaflet commissural portion and the second-leaflet commissural portion, the first stitching being stitched through the separate flexible sheet.

In an application, the second stitching is stitched through the separate flexible sheet.

In an application:
the flexible sheet is a first flexible sheet, the first-leaflet commissural portion is a first first-leaflet commissural portion, and the second-leaflet commissural portion is a first second-leaflet commissural portion,
the first flexible sheet, the first first-leaflet commissural portion, and the first second-leaflet commissural portion are arranged to collectively define a first commissure,
the first leaflet has a second first-leaflet commissural portion,
the second leaflet has a second second-leaflet commissural portion,
the apparatus further includes:
a tubular frame that defines a lumen,
a second flexible sheet,
a third flexible sheet, and
a third prosthetic leaflet, having a first third-leaflet commissural portion and a second third-leaflet commissural portion,
the second second-leaflet commissural portion, the first third-leaflet commissural portion, and the second flexible sheet are arranged to collectively define a second commissure,
the second first-leaflet commissural portion, the second third-leaflet commissural portion, and the third flexible sheet are arranged to collectively define a third commissure,
the first commissure, the second commissure, the third commissure, the first leaflet, the second leaflet, and the third leaflet, are arranged to define a valvular assembly that is secured within the lumen by the first flexible sheet, the second flexible sheet, and the third flexible sheet being connected to the tubular frame, and the valvular assembly is configured to facilitate upstream-to-downstream fluid flow through the lumen by the first, second, and third prosthetic leaflets opening, and to inhibit downstream-to-upstream fluid flow through the lumen by the first, second, and third prosthetic leaflets closing.

In an application, for each of the commissures, the first tab and the second tab each defines a loose region, radially inward from the first stitching and the second stitching, that is loose with respect to the prosthetic leaflets that meet at the commissure.

In an application, the valvular assembly is configured such that, for each of the commissures, in response to the first, second, and third prosthetic leaflets opening, at least part of the first tab and at least part of the second tab move away from each other, and in response to the first, second, and third prosthetic leaflets closing, at least part of the first tab and at least part of the second tab move toward each other.

In an application, the apparatus further includes a tubular frame that is shaped to define a lumen, and the panel is secured against an inner surface of a tubular frame, such that (i) the first tab, the second tab, the first prosthetic leaflet, and the second prosthetic leaflet extend away from the panel into the lumen, and (ii) the first and second leaflets are arranged to facilitate upstream-to-downstream fluid flow through the lumen, and to inhibit downstream-to-upstream fluid flow through the lumen.

In an application, the sheet defines a plurality of flaps extending from the panel, and the panel is secured against the inner surface of the tubular frame by each flap of the plurality of flaps being folded around a respective component of the tubular frame.

In an application, each flap of the plurality of flaps is stitched to the respective component of the tubular frame.

In an application, the sheet is folded to define a first cushion at a downstream edge of the first tab, and a second cushion at a downstream edge of the second tab.

In an application, the first cushion and the second cushion are disposed downstream of the first prosthetic leaflet and the second prosthetic leaflet.

In an application, neither the first cushion nor the second cushion is in contact with the first prosthetic leaflet or the second prosthetic leaflet.

In an application, the first tab defines a downstream opening between the first-tab inner layer and the first-tab outer layer, and the second tab portion defines a downstream opening between the second-tab inner layer and the second-tab outer layer.

In an application:
the sheet defines a first-tab fold and a second-tab fold,
the first cushion includes the first-tab fold, folded between the first-tab inner layer and the first-tab outer layer, and
the second cushion includes the second-tab fold, folded between the second-tab inner layer and the second-tab outer layer.

In an application:
the first-tab fold is a first-tab outer fold, continuous with the first-tab outer layer,
the second-tab fold is a second-tab outer fold, continuous with the second-tab outer layer,
the sheet further defines:
a first-tab inner fold, continuous with the first-tab inner layer, and
a second-tab inner fold, continuous with the second-tab inner layer, the first cushion includes:

the first-tab outer fold, folded between the first-tab outer layer and the first-tab inner fold, and
the first-tab inner fold, folded between the first-tab inner layer and the first-tab outer fold, and
the second cushion includes:
the second-tab outer fold, folded between the second-tab outer layer and the second-tab inner fold, and
the second-tab inner fold, folded between the second-tab inner layer and the second-tab outer fold.

In an application:
the first stitching is stitched along a first stitch line,
the second stitching is stitched along a second stitch line, and
the first stitch line and the second stitch line diverge from each other at 10-45 degrees.

In an application, the first stitch line and the second stitch line diverge from each other at 10-30 degrees.

In an application, the first stitch line and the second stitch line diverge from each other at 15-25 degrees.

In an application, the first stitch line and the second stitch line diverge from each other at 20 degrees.

There is further provided, in accordance with an application of the present invention, apparatus for use with a prosthetic valve, the apparatus including a connector, the connector including a flexible sheet that is folded to define:
a panel, having a first side facing in a first direction, and a second side that is opposite the first side;
a leaflet receptacle, disposed on the first side of the panel, and protruding in the first direction away from the panel; and
a plurality of flaps, each flap folded about a respective fold axis such that at least part of each flap is disposed on the second side of the panel.

In an application, the panel has an edge between the first side and the second side, and each flap is foldable over the edge, so as to be disposed on the second side of the panel.

In an application, the plurality of flaps is arranged in a circuit such that each flap has two adjacent flaps around the circuit, and the fold axis of each flap is oriented at 60-120 degrees from the fold axis of each of its adjacent flaps.

In an application, the flexible sheet is a single unitary flexible sheet, and the unitary flexible sheet is folded to define the panel, the leaflet receptacle, and the plurality of flaps.

In an application, the plurality of flaps includes exactly four flaps.

In an application:
the leaflet receptacle includes:
a first leaflet-engaging tab, extending from the first side of the panel, and defining a first row of first-tab stitching holes and a second row of first-tab stitching holes, and
a second leaflet-engaging tab, extending from the first side of the panel, and defining a first row of second-tab stitching holes and a second row of second-tab stitching holes;
the receptacle is configured to sandwich one or more prosthetic valve leaflets between the leaflet-engaging tabs such that, on opposite sides of the sandwiched leaflets:
the first row of first-tab stitching holes and the first row of second-tab stitching holes are aligned with each other, and
the second row of first-tab stitching holes and the second row of second-tab stitching holes are aligned with each other.

In an application, the first row of first-tab stitching holes and the second row of first-tab stitching holes diverge at 10-45 degrees from each other, and the first row of second-tab stitching holes and the second row of second-tab stitching holes diverge at 10-45 degrees from each other.

In an application, the first row of first-tab stitching holes and the second row of first-tab stitching holes diverge at 10-30 degrees from each other, and the first row of second-tab stitching holes and the second row of second-tab stitching holes diverge at 10-30 degrees from each other.

In an application, the first row of first-tab stitching holes and the second row of first-tab stitching holes diverge at 15-25 degrees from each other, and the first row of second-tab stitching holes and the second row of second-tab stitching holes diverge at 15-25 degrees from each other.

In an application, the flexible sheet is folded such that each of the first leaflet-engaging tab and the second leaflet-engaging tab includes (i) an outer layer, and (ii) an inner layer that is positioned to be sandwiched between the outer layer and the one or more leaflets, and:
the first and second rows of first-tab stitching holes are defined in the inner layer of the first leaflet-engaging tab, and
the first and second rows of second-tab stitching holes are defined in the inner layer of the second leaflet-engaging tab.

In an application:
the first leaflet-engaging tab further defines a third row of first-tab stitching holes, defined in the outer layer of the first leaflet-engaging tab, and aligned with the first row of first-tab stitching holes,
the second leaflet-engaging tab further defines a third row of second-tab stitching holes, defined in the outer layer of the second leaflet-engaging tab, and aligned with the first row of second-tab stitching holes.

In an application, the apparatus further includes:
a tubular frame that defines a lumen therethrough; and
a first prosthetic leaflet and a second prosthetic leaflet, the first and second prosthetic leaflets disposed within the lumen,
and the apparatus defines a commissure at which the first and second leaflets meet each other and are coupled to the frame via the connector.

In an application, the leaflets define an upstream end and a downstream end of the lumen by being arranged and coupled to the frame so as to facilitate one-way fluid flow through the lumen.

In an application:
the leaflet receptacle includes:
a first leaflet-engaging tab, extending from the first side of the panel, and
a second leaflet-engaging tab, extending from the first side of the panel; and
the first and second leaflets are sandwiched together between the first and second leaflet-engaging tabs, and are stitched to the first and second leaflet-engaging tabs such that, on opposite sides of the sandwiched leaflets:
the first row of first-tab stitching holes and the first row of second-tab stitching holes are aligned with each other, and
the second row of first-tab stitching holes and the second row of second-tab stitching holes are aligned with each other.

In an application, the first leaflet has a first-leaflet downstream edge, and the second leaflet has a second-leaflet downstream edge, and each of the first and second leaflet-engaging tabs extends in a downstream direction beyond the first-leaflet downstream edge and the second-leaflet downstream edge.

In an application:
the first leaflet has a first-leaflet downstream edge, and the second leaflet has a second-leaflet downstream edge, the first and second leaflets are configured:
to inhibit fluid flow in an upstream direction by the first and second leaflets moving toward each other in response to the fluid flow in an upstream direction, such that the first-leaflet downstream edge and the second-leaflet downstream edge move away from the frame, and
to facilitate fluid flow in a downstream direction by the first and second leaflets moving away from each other in response to the fluid flow in a downstream direction, such that the first-leaflet downstream edge and the second-leaflet downstream edge move toward the frame,
the first leaflet-engaging tab defines a first cushion that inhibits movement of a commissural portion of the first leaflet toward the frame, and
the second leaflet-engaging tab defines a second cushion that inhibits movement of a commissural portion of the second leaflet toward the frame.

In an application, the first cushion and the second cushion are disposed further downstream than the first-leaflet downstream edge and the second-leaflet downstream edge.

In an application, the first and second cushions are each defined by folds in the flexible sheet.

In an application:
the leaflet receptacle includes:
a first leaflet-engaging tab, extending from the first side of the panel, and defining a first row of first-tab stitching holes and a second row of first-tab stitching holes, and
a second leaflet-engaging tab, extending from the first side of the panel, and defining a first row of second-tab stitching holes and a second row of second-tab stitching holes; and
the first and second leaflets are sandwiched together between the first and second leaflet-engaging tabs, and are stitched to the first and second leaflet-engaging tabs such that, on opposite sides of the sandwiched leaflets:
the first row of first-tab stitching holes and the first row of second-tab stitching holes are aligned with each other, and
the second row of first-tab stitching holes and the second row of second-tab stitching holes are aligned with each other.

In an application, the first and second rows of first-tab stitching holes diverge from each other such that progressively downstream parts of the first and second rows of first-tab stitching holes are progressively further from each other, and the first and second rows of second-tab stitching holes diverge from each other such that progressively downstream parts of the first and second rows of second-tab stitching holes are progressively further from each other.

In an application, the first and second rows of first-tab stitching holes diverge at 10-45 degrees from each other, and the first and second rows of second-tab stitching holes diverge at 10-45 degrees from each other.

In an application:
the connector is a first connector,
the commissure is a first commissure,
the apparatus further includes a second connector, a third connector, and a third leaflet, and
the apparatus defines:
a second commissure at which the second and third leaflets meet each other and are coupled to the frame via the second connector, and
a third commissure at which the third and first leaflets meet each other and are coupled to the frame via the third connector.

In an application, the fold axis of each flap is oriented at 70-110 degrees from the fold axis of each of its adjacent flaps.

In an application, the fold axis of each flap is oriented at 80-100 degrees from the fold axis of each of its adjacent flaps.

In an application, the connector has a folded state in which the sheet is folded to define the panel, the leaflet receptacle, and the plurality of flaps, and the sheet further has an unfolded state in which the sheet defines a plane, and further defines, in the plane:
- the panel, at a medial region of the sheet,
- the flaps, disposed peripherally to the panel,
- a first tab portion and a second tab portion, each of the tab portions disposed peripherally from the panel, and in the folded state, each of the tab portions defines a respective leaflet-engaging tab, and the leaflet receptacle includes the leaflet-engaging tab of each of the tab portions.

In an application, in the folded state, a first flap part of each of the flaps is disposed on the first side of the panel, and each of the flaps is folded around the panel such that a second flap part of each of the flaps is disposed on the second side of the panel.

In an application, the sheet further defines a first bridging element via which the first tab portion is connected to the panel, and a second bridging element via which the second tab portion is connected to the panel.

In an application, in the folded state, the first and second bridging elements extend from respective edges of the panel and toward each other across the first side of the panel, and each of the first and second tab portions protrudes from the respective bridging element in the first direction away from the first side of the panel.

In an application, the flaps are connected to the panel independently of the bridging elements.

In an application, the flaps are connected to the panel via the bridging elements.

In an application, in the unfolded state:
- the panel, the first and second bridging elements, and the first and second tab portions are arranged in a row that defines a lateral axis in the plane, the lateral axis passing through the panel, the first and second bridging elements, and the first and second tab portions, and
- for each of the bridging elements, a first flap of the plurality of flaps and a second flap of the plurality of flaps are connected to the bridging element, the lateral axis passing between the first and second flaps.

In an application, in the folded state, the bridging elements are disposed on the first side of the panel, and each flap extends from one of the bridging elements and around the panel such that a flap part of each flap is disposed on the second side of the panel.

In an application, in the unfolded state, the first tab portion and the second tab portion flank the panel by being disposed, in the plane, on opposing lateral sides of the panel.

In an application, in the unfolded state, the first and second tab portions, the first and second bridging elements, and the panel are arranged in a row that defines a lateral axis in the plane, and the fold axis of each of the flaps is at 30-60 degrees from the lateral axis.

There is further provided, in accordance with an application of the present invention, apparatus for use with a prosthetic valve, the apparatus including a connector, the connector comping:
- a panel, having a first side that faces in a first direction, and a second side that faces in a second, opposite direction;
- a leaflet-engaging tab, protruding from the first side in the first direction; and
- a plurality of flaps, each flap extending from the panel, and configured to fold, over a respective fold axis, toward the second direction, the plurality of flaps arranged in a circuit such that each flap has two adjacent flaps around the circuit, and:
- the fold axis of each flap is oriented at 60-120 degrees from the fold axis of each of its adjacent flaps.

In an application, the panel substantially defines a plane, and each flap is configured to fold, over its respective fold axis, out of the plane.

In an application, each flap is configured to fold over a respective portion of the second side of the panel.

In an application, the connector consists of a single unitary sheet of a material that is folded to define the panel, the leaflet-engaging tab, and the plurality of flaps.

In an application, the plurality of flaps includes exactly four flaps.

In an application, the fold axis of each flap is oriented at 70-110 degrees from the fold axes of its adjacent flaps.

In an application, the fold axis of each flap is oriented at 80-100 degrees from the fold axes of its adjacent flaps.

In an application, the fold axis of each flap is oriented at approximately 90 degrees from the fold axes of its adjacent flaps.

There is further provided, in accordance with an application of the present invention, a method, including:
- folding a flexible sheet to define a connector having:
  - a panel, having a first side facing in a first direction, and a second side that is opposite the first side;
  - a leaflet receptacle, disposed on the first side of the panel, and protruding in the first direction away from the panel; and
  - a plurality of flaps, each flap folded about a respective fold axis such that at least part of each flap is disposed on the second side of the panel;
- attaching one or more leaflets to the connector by stitching the one or more leaflets to the leaflet receptacle; and
- attaching the connector to a frame assembly by folding each flap of the plurality of flaps around a respective component of the frame assembly, and securing them by stitching.

There is further provided, in accordance with an application of the present invention, apparatus for use at a heart valve of a subject, the apparatus including:
- a frame assembly, transluminally advanceable to the heart, and including:
  - an inner stent frame that defines a tubular portion; and
  - an outer stent frame that defines a ring that is coupled to the inner stent frame, and circumscribes the tubular portion; and
- a plurality of prosthetic valve leaflets, coupled to the frame assembly and disposed in the tubular portion, and the inner stent frame is cut from a first tube of nitinol that has a first-tube wall thickness, and the outer stent frame is cut from a second tube of nitinol that has a second-tube wall thickness that is greater than the first-tube wall thickness.

In an application, the first-tube wall thickness is 0.45-0.65 mm, and the second-tube wall thickness is 0.6-0.8 mm.

In an application, the second-tube wall thickness is at least 20 percent greater than the first-tube wall thickness.

In an application, the second-tube wall thickness is at least 30 percent greater than the first-tube wall thickness.

In an application:

the inner frame further defines an annular upstream support portion, extending from the tubular portion, and dimensioned to be placed against an upstream surface of the heart valve, and the outer frame further defines a plurality of flanges that extend from the tubular portion, and are dimensioned to be placed against a downstream surface of the heart valve.

There is further provided, in accordance with an application of the present invention, apparatus for use with a heart of a subject, the apparatus including:

an inner stent frame that:
defines a tubular portion and a plurality of inner-frame coupling elements, and
has a relaxed expanded state in which the tubular portion defines an inner-stent-frame relaxed expanded diameter; and
an outer stent frame, that:
defines a ring and a plurality of outer-frame coupling elements, and
has a relaxed expanded state in which the ring defines an outer-stent-frame relaxed expanded diameter that is smaller than the inner-stent-frame expanded diameter,
and:
together, the inner stent frame and the outer stent frame define at least part of a frame assembly in which the outer-frame coupling elements are fixed to the inner-frame coupling elements and the ring circumscribes the tubular portion, and
the frame assembly:
further includes a plurality of prosthetic leaflets secured to, and disposed within, the tubular portion,
has a compressed state in which the frame assembly is transluminally advanceable to the heart, and
is expandable into an expanded state in which the tubular portion defines an inner-stent-frame constrained expanded diameter that is smaller than the inner-stent-frame relaxed expanded diameter.

In an application, the outer frame is coupled to the inner frame such that:

in the compressed state of the frame assembly, the outer frame is in circumferential contact with the tubular portion, and throughout expansion of the frame assembly into its expanded state, circumferential contact is maintained between the outer frame and the tubular portion.

In an application, the outer-frame coupling elements are welded to the inner-frame coupling elements.

In an application:

the apparatus defines a plurality of commissures at which the leaflets are secured to the frame assembly, and the outer frame is secured to the inner frame by both (i) the fixation of the outer-frame coupling elements to the inner-frame coupling elements, and (ii) stitching of the outer frame to the inner frame at the commissures.

In an application:

the apparatus defines a plurality of commissures, at each of the commissures, the apparatus includes a plurality of stitches, and commissural portions of the two prosthetic leaflets are secured to the inner stent frame and to the outer stent frame via the plurality of stitches.

In an application, at each commissure the apparatus includes a fabric connector to which the commissural portions of the two leaflets are secured, and the plurality of stitches secures the commissural portions of the two leaflets to the inner stent frame and the outer stent frame by being attached to the fabric connector.

In an application, the fabric connector is shaped to define (i) a panel having a first side and a second side, (ii) one or more leaflet-engaging tabs to which the commissural portions of the two leaflets are stitched, the tabs protruding from the first side of the panel, and (iii) a plurality of flaps, wrapped around elements of the inner stent frame and elements of the outer stent frame, and secured thus by stitching.

There is further provided, in accordance with an application of the present invention, apparatus for use in a heart of a subject, the apparatus including:

a frame assembly defining:
a tubular portion that defines a longitudinal lumen therethrough,
an upstream support portion, coupled to the tubular portion, and
a plurality of flanges, coupled to the tubular portion; and
a plurality of prosthetic valve leaflets, coupled to the tubular portion, and disposed within the lumen,
and:
the frame assembly:
has a compressed state for transluminal delivery to the heart, and
has an expanded state, in which:
the upstream support portion extends radially outward from the tubular portion,
the flanges extend radially outward from the tubular portion and toward the upstream support portion,
the tubular portion has a transverse cross-sectional area, and
the frame assembly defines a toroidal space between the flanges, the upstream support portion, and the tubular portion, the toroidal space circumscribing the tubular portion and having a cross-sectional area that is 5-10 percent of the transverse cross-sectional area of the tubular portion.

In an application:

the frame assembly is a first frame assembly, the plurality of leaflets is a first plurality of leaflets, and the apparatus includes a first implant that includes the first frame assembly and the first plurality of leaflets, and the apparatus further includes a second implant that includes:

a second frame assembly defining:
a second tubular portion that defines a second longitudinal lumen therethrough,
a second upstream support portion, coupled to the second tubular portion, and
a second plurality of flanges, coupled to the second tubular portion; and
a second plurality of prosthetic valve leaflets, coupled to the second tubular portion, and disposed within the second lumen,
and:
the second frame assembly:
has a compressed state for transluminal delivery to the heart, and has an expanded state, in which:
the second upstream support portion extends radially outward from the second tubular portion; and
the flanges of the second plurality of flanges extend radially outward from the second tubular portion and toward the second upstream support portion,
the second tubular portion has a transverse cross-sectional area that is at least 30 percent greater than the transverse cross-sectional area of the first tubular portion of the first implant, and the second frame assembly defines a second toroidal space between the flanges of the second plurality of flanges, the second upstream support portion, and the second tubular portion, the second toroidal space circumscribing the second tubular portion and having a cross-sectional area that is 5-10 percent of the transverse cross-sectional area of the second tubular portion.

In an application, the frame assembly is dimensioned such that the cross-sectional area of the toroidal space is 5-8 percent of the transverse cross-sectional area of the tubular portion.

In an application, the frame assembly is dimensioned such that the cross-sectional area of the toroidal space is 6-7 percent of the transverse cross-sectional area of the tubular portion.

In an application, the frame assembly is dimensioned such that the cross-sectional area of the toroidal space is 6.5-7.5 percent of the transverse cross-sectional area of the tubular portion.

In an application, the upstream support portion includes a plurality of arms that, in the expanded state of the frame assembly, protrude radially outward from the tubular portion.

In an application:
the tubular portion has an upstream end and a downstream end,
the prosthetic leaflets are configured to provide one-way blood flow through the lumen from the upstream end to the downstream end,
each arm of the plurality of arms is attached to the tubular portion at a site that is downstream of the upstream end,
progressively lateral portions of each arm define, respectively:
an ascending portion that extends in an upstream direction past the upstream end of the tubular portion,
an arch portion that curves in a downstream direction to form an arch, and
a lateral portion that curves in an upstream direction.

In an application, the frame assembly defines the toroidal space between the flanges, the tubular portion, and the arch portions of the arms of the upstream support portion.

In an application, each flange extends radially outward from the tubular portion and toward a tip of the flange, and the arch portion of the arms curves in a downstream direction past the tips of the flanges.

There is further provided, in accordance with an application of the present invention, apparatus for use at a heart valve of a subject, the apparatus including:
a first implant and a second implant, each implant being transluminally advanceable to the heart, and including:
a frame assembly that includes:
an inner stent frame that defines a tubular portion that defines a lumen; and
an outer stent frame that defines a ring that is coupled to the inner stent frame, and circumscribes the tubular portion; and
a plurality of prosthetic valve leaflets, coupled to the frame assembly and disposed in the tubular portion; and
a delivery tool, including a delivery capsule that has a capsule diameter,
and:
the first implant has:
an expanded state in which its lumen has a lumen diameter, and a compressed state in which the first implant has a compressed diameter, and is dimensioned to be housed within the delivery capsule, and
the second implant has:
an expanded state in which its lumen has a lumen diameter that is at least 15 percent greater than the lumen diameter of the first implant, and
a compressed state in which the second implant has a compressed diameter that is no more than 2 percent greater than the compressed diameter of the first implant, and is dimensioned to be housed within the delivery capsule.

There is further provided, in accordance with an application of the present invention, apparatus, including:
a unitary flexible sheet that, in an unfolded state of the sheet, defines:
a panel portion at a medial region of the sheet,
a first tab portion disposed peripherally to the panel, and having (i) a first part, and (ii) a second part that is disposed peripherally to the first part of the first tab portion, and
a second tab portion disposed peripherally to the panel opposite the first tab portion, and having (i) a first part, and (ii) a second part that is disposed peripherally to the first part of the second tab portion,
the sheet being folded into a folded state in which the sheet defines:
a panel, defined by the panel portion, having a first side facing in a first direction, and a second side that is opposite the first side;
a first tab, defined by the first tab portion, the first tab being disposed on the first side of the panel, and having:
a first-tab inner layer defined by the first part of the first tab portion extending away from the panel in the first direction, and
a second-tab outer layer defined by the second part of the first tab portion being folded back over the first part of the first tab portion, and extending back toward the panel;
a second tab, defined by the second tab portion, the second tab being disposed on the first side of the panel, and having:
a second-tab inner layer defined by the first part of the second tab portion extending away from the panel in the first direction, and
a second-tab outer layer defined by the second part of the second tab portion being folded back over the first part of the second tab portion, and extending back toward the panel;
a first prosthetic leaflet having a first-leaflet commissural portion sandwiched between the first-tab inner layer and the second-tab inner layer;
a second prosthetic leaflet having a second-leaflet commissural portion sandwiched between the first-tab inner layer and the second-tab inner layer.

In an application, the apparatus further includes a stitching, stitched through the first-tab inner layer, the first-leaflet commissural portion, the second-leaflet commissural portion, and the second-tab inner layer.

In an application, the first-tab outer layer and the second-tab outer layer cover the stitching.

In an application, the stitching is a first stitching, and the apparatus further includes a second stitching, stitched through the first-tab outer layer, the first-tab inner layer, the first-leaflet commissural portion, the second-leaflet commissural portion, the second-tab inner layer, and the second-tab outer layer.

The present invention will be more fully understood from the following detailed description of applications thereof, taken together with the drawings, in which:

BRIEF DESCRIPTION OF THE DRAWINGS

FIGS. 1A-B and 2A-E are schematic illustrations of an implant for use with a native valve of a heart of a subject, in accordance with some applications of the invention;

FIGS. 3A-C are schematic illustrations that show structural changes in a frame assembly during transitioning of the assembly between its compressed and expanded states, in accordance with some applications of the invention;

FIGS. 4A-F are schematic illustrations of implantation of the implant at the native valve, in accordance with some applications of the invention;

FIGS. 7A-B and 8A-B are schematic illustrations of frame assemblies of respective implants, in accordance with some applications of the invention;

FIGS. 9A-C are schematic illustrations of an implant comprising a frame assembly, in accordance with some applications of the invention;

FIGS. 12A-B and 13A-G are schematic illustrations of a connector for connecting prosthetic leaflets to a frame of a prosthetic valve implant, in accordance with some applications of the invention; and FIGS. 14A-B are schematic illustrations of a connector for connecting prosthetic leaflets to a frame of a prosthetic valve implant, in accordance with some applications of the invention.

DETAILED DESCRIPTION OF EMBODIMENTS

Figure 3C:
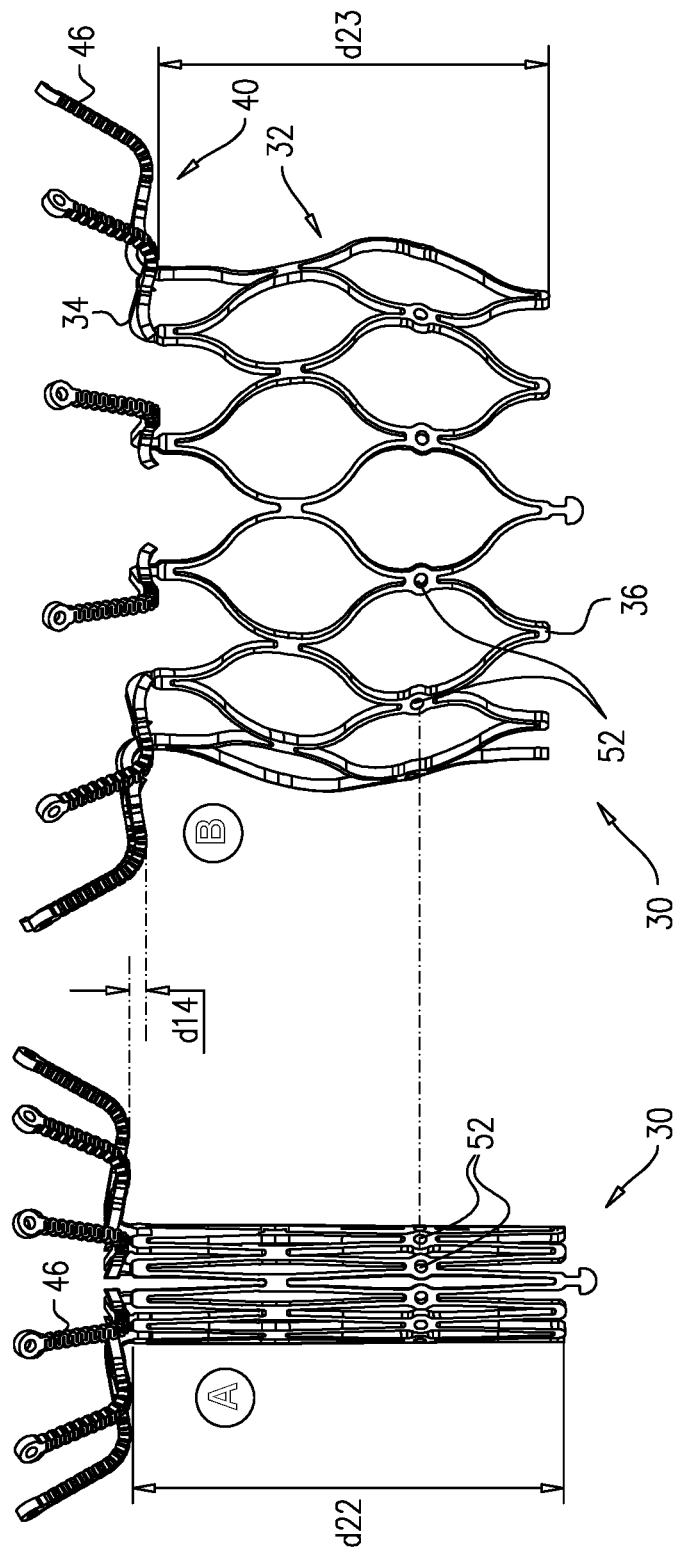

Reference is made to FIGS. 1A-B and 2A-E, which are schematic illustrations of an implant 20 for use with a native valve of a heart of a subject, in accordance with some applications of the invention. Implant 20 comprises a frame assembly 22 that has an upstream end 24, a downstream end 26, and a central longitudinal axis ax1 therebetween. Frame assembly 22 comprises a valve frame 30 that comprises a tubular portion 32 that has an upstream end 34 and a downstream end 36, and is shaped to define a lumen 38 through the tubular portion from the upstream end to the downstream end. Tubular portion 32 circumscribes axis ax1, and thereby defines lumen 38 along the axis. Valve frame 30 further comprises an upstream support portion 40, extending from upstream end 34 of tubular portion 32. Frame assembly 22 further comprises at least one leg 50, coupled to valve frame 30 at (e.g., via) a coupling point 52, and having a tissue-engaging flange 54.

Typically, and as described hereinbelow, leg 50 is part of an outer frame (or "leg frame") 60, and frames 30 and 60 define respective coupling elements 31 and 61, which are fixed with respect to each other at coupling points 52. Typically, frames 30 and 60 are coupled to each other only at coupling points 52 (e.g., only via the fixation of coupling elements 31 and 61 with respect to each other).

Implant 20 further comprises a valve member 58 (e.g., one or more prosthetic leaflets) disposed within lumen 38, and configured to facilitate one-way liquid flow through the lumen from upstream end 34 to downstream end 36 (e.g., thereby defining the orientation of the upstream and downstream ends of tubular portion 32). FIG. 1A shows implant 20 in a fully-expanded state, in which frame assembly 22 is in a fully-expanded state. FIG. 1B shows an exploded view of frame assembly 22 in its fully-expanded state. FIGS. 2A-E show respective states of implant 20, which will be discussed in more detail hereinbelow with respect to the implantation of the implant and the anatomy in which the implant is implanted. FIG. 2A shows implant 20 in a compressed state (in which frame assembly 22 is in a compressed state), for percutaneous delivery of the implant to the heart of the subject. Typically, in the compressed state, leg 50 (including flange 54 thereof) is in a constrained-flange state in which the flange is generally parallel with axis ax1. Further typically, in the compressed state, upstream support portion 40 is generally tubular, collinear with tubular portion 32 (e.g., extending collinearly from the tubular portion), and disposed around axis ax1.

FIG. 2B shows a state of implant 20 in which tissue-engaging flange 54 of each leg 50 extends radially away from axis ax1 (e.g., radially away from tubular portion 32). FIG. 2C shows a state of implant 20 in which upstream-support portion 40 extends radially away from axis ax1 (and thereby radially away from tubular portion 32). FIG. 2D shows a state of implant 20 in which both flange 54 and portion 40 extend away from axis ax1. In the fully-expanded state (FIGS. 1A-B) both upstream support portion 40 and flange 54 extend radially away from axis ax1. Typically, frame assembly 22 is biased (e.g., shape-set) to assume its fully-expanded state, which is shown in FIG. 2E. Transitioning of implant 20 between the respective states is typically controlled by delivery apparatus, such as by constraining the implant in a compressed state within a delivery tube and/or against a control rod, and selectively releasing portions of the implant to allow them to expand.

In the compressed state of frame assembly 22, tubular portion 32 has a diameter d1, and in the expanded state, the tubular portion has a diameter d2 that is greater that diameter d1. For some applications, diameter d1 is 4-15 mm, (e.g., 5-11 mm) and diameter d2 is 20-50 mm, (e.g., 23-33 mm). For some applications, and as shown, in its expanded state tubular portion 32 bulges slightly in its middle (e.g., is slightly barrel-shaped). For such applications, values of diameter d2 are the average diameter along the tubular portion. Similarly, values for the cross-sectional area of the tubular portion are the average cross-sectional area along the tubular portion. This also applies to other implants described herein, mutatis mutandis.

Frame assembly 22 is configured such that increasing the diameter of tubular portion 32 (e.g., from d1 to d2) causes longitudinal movement of flange 54 away from coupling point 52. In the same way, reducing the diameter of tubular portion 32 (e.g., from d2 to d1) causes longitudinal movement of flange 54 toward coupling point 52. It is to be noted that the term "longitudinal movement" (including the specification and the claims) means movement parallel with central longitudinal axis ax1. Therefore, longitudinal movement of flange 54 away from coupling point 52 means increasing a distance, measured parallel with longitudinal axis ax1, between flange 54 and coupling point 52. An example of such a configuration is described in more detail with respect to FIG. 3A.

Similarly reference to an element being "upstream of" (or "above") or "downstream of" (or "below") another element refers to its relative position along the central longitudinal axis of the implant ("upstream" and "downstream" being defined by the direction in which the implant facilitates blood flow).

Thus, expansion of tubular portion 32 from its compressed state toward its expanded state (i) increases a circumferential distance between each of coupling points 52 and its adjacent coupling points (e.g., between each of outer-frame coupling elements 61 and its adjacent outer-frame coupling elements) (e.g., from d8 to d9), and (ii) moves legs 50 in a longitudinally upstream direction with respect to the tubular portion.

Typically, frame assembly 22 is configured such that increasing the diameter of tubular portion 32 also causes longitudinal movement of upstream support portion 40 toward coupling point 52, e.g., as described in more detail with respect to FIGS. 3B-C. Typically, frame assembly 22 is configured such that increasing the diameter of tubular portion 32 also causes longitudinal movement of upstream end 34 of tubular portion 32 toward coupling point 52. In the same way, reducing the diameter of tubular portion 32 causes longitudinal movement of upstream end 34 away from coupling point 52.

For some applications, upstream support portion 40 comprises a plurality of arms 46 that each extends radially outward from tubular portion 32 (e.g., from upstream end 34 of the tubular portion). Arms 46 are typically flexible. For some such applications, arms 46 are coupled to tubular portion 32 such that each arm may deflect independently of adjacent arms during implantation (e.g., due to anatomical topography).

For some applications, upstream support portion 40 comprises a plurality of barbs 48 that extend out of a downstream surface of the upstream support portion. For example, each arm 46 may comprise one or more of barbs 48. Barbs 48 press into tissue upstream of the native valve (e.g., into the valve annulus), thereby inhibiting downstream movement of implant 20 (in addition to inhibition of downstream movement provided by the geometry of upstream support portion 40).

One or more surfaces of frame assembly 22 are covered with a covering 23, which typically comprises a flexible sheet, such as a fabric, e.g., comprising polyester. Typically, covering 23 covers at least part of tubular portion 32, typically lining an inner surface of the tubular portion, and thereby defining lumen 38.

Further typically, upstream support portion 40 is covered with covering 23, e.g., extending between arms 46 to form an annular shape. It is hypothesized that this reduces a likelihood of paravalvular leakage. For such applications, excess covering 23 may be provided between arms 46 of upstream support portion 40, so as to facilitate their independent movement. Although FIG. 1A shows covering 23 covering an upstream side of upstream support portion 40, the covering typically additionally (or alternatively) covers the downstream side of the upstream support portion. For example, covering 23 may extend over the tips of arms 46 and down the outside of the arms, or a separate piece of covering may be provided on the downstream side of the upstream support portion.

Alternatively, each arm 46 may be individually covered in a sleeve of covering 23, thereby facilitating independent movement of the arms.

For some applications, at least part of legs 50 (e.g., flanges thereof) is covered with covering 23.

Typically, frame assembly 22 comprises a plurality of legs 50 (e.g., two or more legs, e.g., 2-16 legs, such as 4-12 legs, such as 6-12 legs), arranged circumferentially around valve frame 30 (e.g., around the outside of tubular portion 32). Typically, frame assembly 22 comprises a plurality of coupling points 52 at which the legs are coupled to valve frame 30.

As described in more detail hereinbelow (e.g., with reference to FIG. 3A), each leg 50 is typically coupled to a coupling point 52 via a strut 70. For some applications, each leg 50 is coupled to a plurality of (e.g., two) coupling points 52 via a respective plurality of (e.g., two) struts 70. For some such applications, frame assembly 22 is arranged such that, in the expanded state of the frame assembly, leg 50 is disposed, circumferentially with respect to tubular portion 32, between two struts, and each of the two struts are disposed, circumferentially with respect to the tubular portion, between the leg and a respective coupling point 52.

For some applications, a plurality of (e.g., two) legs are coupled to each coupling point 52 via a respective plurality of (e.g., two) struts 70. For some such applications, frame assembly 22 is arranged such that, in the expanded state of the frame assembly, coupling point 52 is disposed, circumferentially with respect to tubular portion 32, between two struts 70, and each of the two struts are disposed, circumferentially with respect to the tubular portion, between the coupling point and a respective leg 50.

For some applications, frame assembly 22 comprises an outer frame (e.g., a leg frame) 60 that circumscribes tubular portion 32, comprises (or defines) the plurality of legs 50 and the plurality of struts 70, and is coupled to valve frame 30 at the plurality of coupling points 52, such that the plurality of legs are distributed circumferentially around the tubular portion. For such applications, outer frame 60 comprises a ring 66 that is defined by a pattern of alternating peaks 64 and troughs 62, and that typically circumscribes tubular portion 32. For example, the ring may comprise struts 70, extending between the peaks and troughs. Peaks 64 are longitudinally closer to upstream end 34 of tubular portion 32 than to downstream end 36, and troughs 62 are longitudinally closer to the downstream end than to the upstream end. (It is to be noted that throughout this patent application, including the specification and the claims, the term "longitudinally" means with respect to longitudinal axis ax1. For example, "longitudinally closer" means closer along axis ax1 (whether positioned on axis ax1 or lateral to axis ax1), and "longitudinal movement" means a change in position along axis ax1 (which may be in additional to movement toward or away from axis ax1).) Therefore, peaks 64 are closer than troughs 62 to upstream end 34, and troughs 62 are closer than peaks 64 to downstream end 36. For applications in which frame 60 comprises ring 66, each leg 50 is coupled to the ring (or defined by frame 60) at a respective trough 62.

In the embodiment shown, the peaks and troughs are defined by ring 66 having a generally zig-zag shape. However, the scope of the invention includes ring 66 having another shape that defines peaks and troughs, such as a serpentine or sinusoid shape.

For applications in which frame assembly 22 has a plurality of coupling points 52, the coupling points (and therefore coupling elements 31 and 61) are disposed circumferentially around the frame assembly (e.g., around axis ax1), typically on a transverse plane that is orthogonal to axis ax1. This transverse plane is illustrated by the position of section A-A in FIG. 2B. Alternatively, coupling points 52 may be disposed at different longitudinal heights of frame assembly 22, e.g., such that different flanges 54 are positioned and/or moved differently to others. Typically, coupling points 52 (and therefore coupling elements 31 and 61) are disposed longitudinally between upstream end 24 and downstream end 26 of frame assembly 22, but not at either of these ends. Further typically, coupling points 52 are disposed longitudinally between upstream end 34 and downstream end 36 of tubular portion 32, but not at either of these ends. For example, the coupling points may be more than 3 mm (e.g., 4-10 mm) both from end 34 and from end 36. It is hypothesized that this advantageously positions the coupling points at a part of tubular portion 32 that is more rigid than end 34 or end 36.

It is to be noted that leg 50 is typically expandable into its expanded state (e.g., a released-flange state) such that flange 54 extends away from axis ax1, independently of increasing the diameter of tubular portion 32 (e.g., as shown in FIGS. 2B & 2D). Similarly, upstream support portion 40 is typically expandable into its expanded state (e.g., a released-arm state) such that it (e.g., arms 46 thereof) extends away from axis ax1, independently of increasing the diameter of tubular portion 32 (e.g., as shown in FIGS. 2C & 2D). The state shown in FIG. 2D may be considered to be an intermediate state. Therefore, implant 20 is typically configured such that legs 50 (e.g., flanges 54 thereof) and upstream support portion 40 are expandable such that they both extend away from axis ax1, while retaining a distance d3 therebetween. This distance is subsequently reducible to a distance d4 by expanding tubular portion 32 (e.g., shown in FIG. 2E).

For some applications, while tubular portion 32 remains in its compressed state, flange 54 can extend away from axis ax1 over 40 percent (e.g., 40-80 percent, such as 40-70 percent) of the distance that it extends from the axis subsequent to the expansion of the tubular portion. For example, for applications in which implant 20 comprises a flange on opposing sides of the implant, a span d15 of the flanges while tubular portion 32 is in its compressed state may be at least 40 percent (e.g., 40-80 percent, such as 40-70 percent) as great as a span d16 of the flanges subsequent to the expansion of the tubular portion. For some applications, span d15 is greater than 15 mm and/or less than 50 mm (e.g., 20-30 mm). For some applications, span d16 is greater than 30 mm and/or less than 60 mm (e.g., 40-50 mm). It is to be noted that flange 54 is effectively fully expanded, with respect to other portions of leg 50 and/or with respect to tubular portion 32, before and after the expansion of the tubular portion.

Similarly, for some applications, while tubular portion 32 remains in its compressed state, upstream support portion 40 (e.g., arms 46) can extend away from axis ax1 over 30 percent (e.g., 30-70 percent) of the distance that it extends from the axis subsequent to the expansion of the tubular portion. That is, for some applications, a span d17 of the upstream support portion while tubular portion 32 is in its compressed state may be at least 30 percent (e.g., 30-70 percent) as great as a span d18 of the upstream support portion subsequent to the expansion of the tubular portion. For some applications, span d17 is greater than 16 mm (e.g., greater than 20 mm) and/or less than 50 mm (e.g., 30-40 mm). For some applications, span d18 is greater than 40 mm and/or less than 65 mm (e.g., 45-56 mm, such as 45-50 mm). It is to be noted that upstream support portion 40 is effectively fully expanded, with respect to tubular portion 32, before and after the expansion of the tubular portion.

It is to be noted that when tubular portion 32 is expanded, flanges 54 typically translate radially outward from span d15 to span d16 (e.g., without deflecting). Typically, upstream support portion 40 behaves similarly (e.g., arms 46 translated radially outward from span d17 to span d18, e.g., without deflecting). That is, an orientation of each flange 54 and/or each arm 46 with respect to tubular portion 32 and/or axis ax1 is typically the same in the state shown in FIG. 2D as it is in the state shown in FIG. 2E. Similarly, for some applications an orientation of each flange 54 with respect to upstream support portion 40 (e.g., with respect to one or more arms 46 thereof) is the same before and after expansion of tubular portion 32.

For some applications, increasing the diameter of tubular portion 32 from d1 to d2 causes greater than 1 mm and/or less than 20 mm (e.g., 1-20 mm, such as 1-10 mm or 5-20 mm) of longitudinal movement of flange 54 away from coupling point 52. For some applications, increasing the diameter of tubular portion 32 from d1 to d2 causes greater than 1 mm and/or less than 20 mm (e.g., 1-20 mm, such as 1-10 mm or 5-20 mm) of longitudinal movement of upstream support portion 40 toward coupling point 52. For some applications, distance d3 is 7-30 mm. For some applications, distance d4 is 0-15 mm (e.g., 2-15 mm). For some applications, increasing the diameter of tubular portion 32 from d1 to d2 reduces the distance between the upstream support portion and flanges 54 by more than 5 mm and/or less than 30 mm, such as 5-30 mm (e.g., 10-30 mm, such as 10-20 mm or 20-30 mm). For some applications, the difference between d3 and d4 is generally equal to the difference between d1 and d2. For some applications, the difference between d3 and d4 is more than 1.2 and/or less than 3 times (e.g., 1.5-2.5 times, such as about 2 times) greater than the difference between d1 and d2.

For some applications, flanges 54 curve such that a tip of each flange is disposed at a shallower angle with respect to inner region 42 of upstream support portion 40, than are portions of leg 50 that are closer to downstream end 26 of frame assembly 22. For some such applications, a tip of each flange may be generally parallel with inner region 42. For some such applications, while tubular portion 32 is in its expanded state, a tip portion 55 of each flange 54 that extends from the tip of the flange at least 2 mm along the flange, is disposed within 2 mm of upstream support portion 40. Thus, for some applications, while tubular portion 32 is in its expanded state, for at least 5 percent (e.g., 5-8 percent, or at least 8 percent) of span 18 of upstream support portion 40, the upstream support portion is disposed within 2 mm of a flange 54.

For some applications, in the absence of any obstruction (such as tissue of the valve or covering 23) between flange 54 and upstream support portion 40, increasing the diameter of tubular portion 32 from d1 to d2 causes the flange and the upstream support portion to move past each other (e.g., the flange may move between arms 46 of the upstream support portion), such that the flange is closer to the upstream end of implant 20 than is the upstream support portion, e.g., as shown hereinbelow for frame assemblies 122 and 222, mutatis mutandis. (For applications in which upstream support portion 40 is covered by covering 23, flanges 54 typically don't pass the covering. For example, in the absence of any obstruction, flanges 54 may pass between arms 46, and press directly against covering 23.) It is hypothesized that for some applications this configuration applies greater force to the valve tissue being sandwiched, and thereby further facilitates anchoring of the implant. That is, for some applications, distance d3 is smaller than the sum of distance d5 and a distance d14 (described with reference to FIG. 3C). For some applications, increasing the diameter of tubular portion 32 from d1 to d2 advantageously causes flanges 54 and upstream support portion 40 to move greater than 3 mm and/or less than 25 mm (e.g., greater than 5 mm and/or less than 15 mm, e.g., 5-10 mm, such as about 7 mm) with respect to each other (e.g., toward each other and then past each other).

For some applications, in the expanded state of frame assembly 22, upstream support portion 40 has an inner region (e.g., an inner ring) 42 that extends radially outward at a first angle with respect to axis ax1 (and typically with respect to tubular portion 32), and an outer region (e.g., an outer ring) 44 that extends, from the inner region, further radially outward from the tubular portion at a second angle with respect to the tubular portion, the second angle being smaller than the first angle. For example, for some applications inner region 42 extends radially outward at an angle alpha_1 of 60-120 degrees (e.g., 70-110 degrees) with respect to axis ax1, and outer region 44 extends radially outward at an angle alpha_2 of 5-70 degrees (e.g., 10-60 degrees) with respect to axis ax1.

It is to be noted that angles alpha_1 and alpha_2 are measured between the respective region support portion 40, and the portion of axis ax1 that extends in an upstream direction from the level of frame assembly 22 at which the respective region begins to extend radially outward.

For some applications in which implant 20 is configured to be placed at an atrioventricular valve (e.g., a mitral valve or a tricuspid valve) of the subject, region 42 is configured to be placed against the upstream surface of the annulus of the atrioventricular valve, and region 44 is configured to be placed against the walls of the atrium upstream of the valve.

For some applications, outer region 44 is more flexible than inner region 42. For example, and as shown, each arm 46 may have a different structure in region 44 than in region 42. It is hypothesized that the relative rigidity of region 42 provides resistance against ventricular migration of implant 20, while the relative flexibility of region 44 facilitates conformation of upstream support portion 40 to the atrial anatomy.

For some applications, two or more of arms 46 are connected by a connector (not shown), reducing the flexibility, and/or the independence of movement of the connected arms relative to each other. For some applications, arms 46 are connected in particular sectors of upstream support portion 40, thereby making these sectors more rigid than sectors in which the arms are not connected. For example, a relatively rigid sector may be provided to be placed against the posterior portion of the mitral annulus, and a relatively flexible sector may be provided to be placed against the anterior side of the mitral annulus, so as to reduce forces applied by upstream support portion 40 on the aortic sinus.

For some applications, and as shown, coupling points 52 are disposed closer to downstream end 26 of frame assembly 22 than are flanges 54, or is upstream support portion 40.

As described in more detail with respect to FIGS. 4A-F, the movement of flange 54 away from coupling point 52 (and the typical movement of upstream support portion 40 toward the coupling point) facilitates the sandwiching of tissue of the native valve (e.g., leaflet and/or annulus tissue) between the flange and the upstream support portion, thereby securing implant 20 at the native valve.

Typically, in the compressed state of tubular portion 32, a downstream end of each leg 50 is longitudinally closer than valve-frame coupling elements 31 to downstream end 36, and flange 54 of each leg is disposed longitudinally closer than the valve-frame coupling elements to upstream end 34. Typically, this is also the case in the expanded state of tubular portion 32.

FIGS. 3A-C show structural changes in frame assembly 22 during transitioning of the assembly between its compressed and expanded states, in accordance with some applications of the invention. FIGS. 3A-C each show a portion of the frame assembly, the structural changes thereof being representative of the structural changes that occur in other portions of the frame assembly. FIG. 3A shows a leg 50 and struts 70 (e.g., a portion of outer frame 60), and illustrates the structural changes that occur around outer frame 60. FIG. 3B shows a portion of valve frame 30, and illustrates the structural changes that occur around the valve frame. FIG. 3C shows valve frame 30 as a whole. In each of FIGS. 3A-C, state (A) illustrates the structure while frame assembly 22 (and in particular tubular portion 32) is in its compressed state, and state (B) illustrates the structure while the frame assembly (and in particular tubular portion 32) is in its expanded state.

FIG. 3A shows structural changes in the coupling of legs 50 to coupling point 52 (e.g., structural changes of outer frame 60) during the transitioning of frame assembly 22 (and in particular tubular portion 32) between its compressed and expanded states. Each leg 50 is coupled to valve frame 30 via at least one strut 70, which connects the leg to coupling point 52. Typically, each leg 50 is coupled to valve frame 30 via a plurality of struts 70. A first end 72 of each strut 70 is coupled to leg 50, and a second end 74 of each strut is coupled to a coupling point 52. As described hereinabove, for applications in which frame 60 comprises ring 66, each leg 50 is coupled to the ring at a respective trough 62. Ring 66 may comprise struts 70, extending between the peaks and troughs, with each first end 72 at (or close to) a trough 62, and each second end 74 at (or close to) a peak 64.

In the compressed state of frame assembly 22 (and in particular of tubular portion 32), each strut 70 is disposed at a first angle in which first end 72 is disposed closer than second end 74 to the downstream end of the frame assembly. Expansion of frame assembly 22 (and in particular of tubular portion 32) toward its expanded state causes strut 70 to deflect to a second angle. This deflection moves first end 72 away from the downstream end of frame assembly 22. That is, in the expanded state of frame assembly 22, first end 72 is further from the downstream end of the frame assembly than it is when the frame assembly is in its compressed state. This movement is shown as a distance d5 between the position of end 72 in state (A) and its position in state (B). This movement causes the above-described movement of flanges 54 away from coupling points 52. As shown, flanges 54 typically move the same distance d5 in response to expansion of frame assembly 22.

For applications in which outer frame 60 comprises ring 66, the pattern of alternating peaks and troughs may be described as having an amplitude longitudinally between the peaks and troughs, i.e., measured parallel with central longitudinal axis ax1 of frame assembly 22, and the transition between the compressed and expanded states may be described as follows: In the compressed state of frame assembly 22 (and in particular of tubular portion 32), the pattern of ring 66 has an amplitude d20. In the expanded state frame assembly 22 (and in particular of tubular portion 32), the pattern of ring 66 has an amplitude d21 that is lower than amplitude d20. Because (i) it is at peaks 64 that ring 66 is coupled to valve frame 30 at coupling points 52, and (ii) it is at troughs 62 that ring 66 is coupled to legs 50, this reduction in the amplitude of the pattern of ring 66 moves legs 50 (e.g., flanges 54 thereof) longitudinally further from the downstream end of the frame assembly. The magnitude of this longitudinal movement (e.g., the difference between magnitudes d20 and d21) is equal to d5.

Typically, distance d5 is the same distance as the distance that flange 54 moves away from coupling point 52 during expansion of the frame assembly. That is, a distance between flange 54 and the portion of leg 50 that is coupled to strut 70, typically remains constant during expansion of the frame assembly. For some applications, the longitudinal movement of flange 54 away from coupling point 52 is a translational movement (e.g., a movement that does not include rotation or deflection of the flange).

For some applications, a distance d6, measured parallel to axis ax1 of frame assembly 22, between coupling point 52 and first end 72 of strut 70 while assembly 22 is in its compressed state, is 3-15 mm. For some applications, a distance d7, measured parallel to axis ax1, between coupling point 52 and first end 72 of strut 70 while assembly 22 is in its expanded state, is 1-5 mm (e.g., 1-4 mm).

For some applications, amplitude d20 is 2-10 mm (e.g., 4-7 mm). For some applications, amplitude d21 is 4-9 mm (e.g., 5-7 mm).

For some applications, and as shown, in the expanded state, first end 72 of strut 70 is disposed closer to the downstream end of frame assembly 22 than is coupling point 52. For some applications, in the expanded state, first end 72 of strut 70 is disposed further from the downstream end of frame assembly 22 than is coupling point 52.

For applications in which frame assembly 22 comprises a plurality of legs 50 and a plurality of coupling points 52 (e.g., for applications in which the frame assembly comprises outer frame 60) expansion of the frame assembly increases a circumferential distance between adjacent coupling points 52, and an increase in a circumferential distance between adjacent legs 50. FIG. 3A shows such an increase in the circumferential distance between adjacent coupling points 52, from a circumferential distance d8 in the compressed state to a circumferential distance d9 in the expanded state. For some applications, distance d8 is 1-6 mm. For some applications, distance d9 is 3-15 mm.

For some applications, in addition to being coupled via ring 66 (e.g., struts 70 thereof) legs 50 are also connected to each other via connectors 78. Connectors 78 allow the described movement of legs 50 during expansion of frame assembly 22, but typically stabilize legs 50 relative to each other while the frame assembly is in its expanded state. For example, connectors 78 may bend and/or deflect during expansion of the frame assembly.

FIGS. 3B-C show structural changes in valve frame 30 during the transitioning of frame assembly 22 between its compressed and expanded states. Tubular portion 32 of valve frame 30 is defined by a plurality of cells 80, which are defined by the repeating pattern of the valve frame. When frame assembly 22 is expanded from its compressed state toward its expanded state, cells 80 (i) widen from a width d10 to a width d11 (measured orthogonal to axis ax1 of the frame assembly), and (ii) shorten from a height d12 to a height d13 (measured parallel to axis ax1 of the frame assembly). This shortening reduces the overall height (i.e., a longitudinal length between upstream end 34 and downstream end 36) of tubular portion 32 from a height d22 to a height d23, and thereby causes the above-described longitudinal movement of upstream support portion 40 toward coupling points 52 by a distance d14 (shown in FIG. 3C). For some applications, and as shown, coupling points 52 are disposed at the widest part of each cell.

Figure 4A:
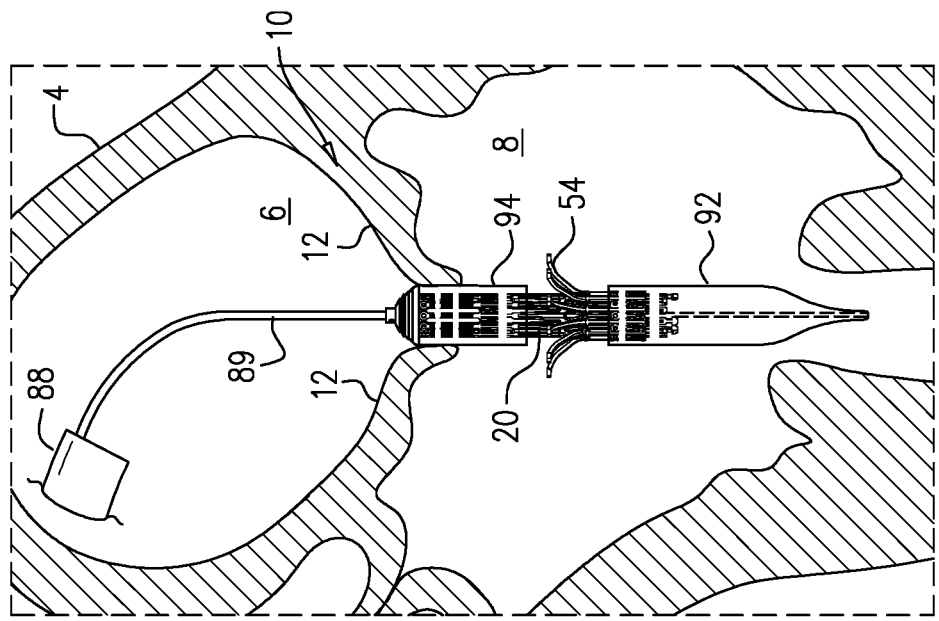
Figure 4B:
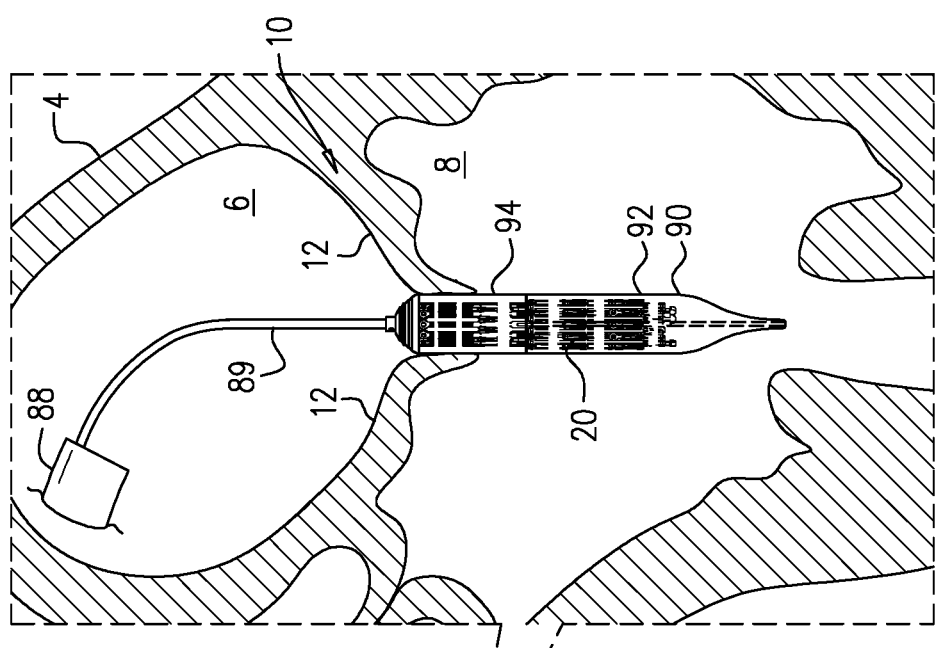
Figure 4D:
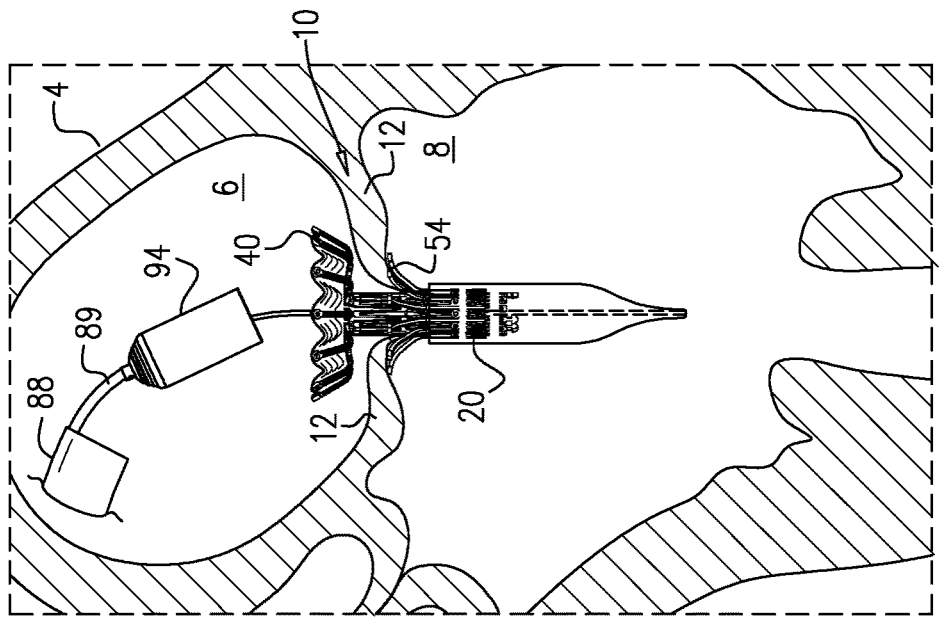
Figure 4C:
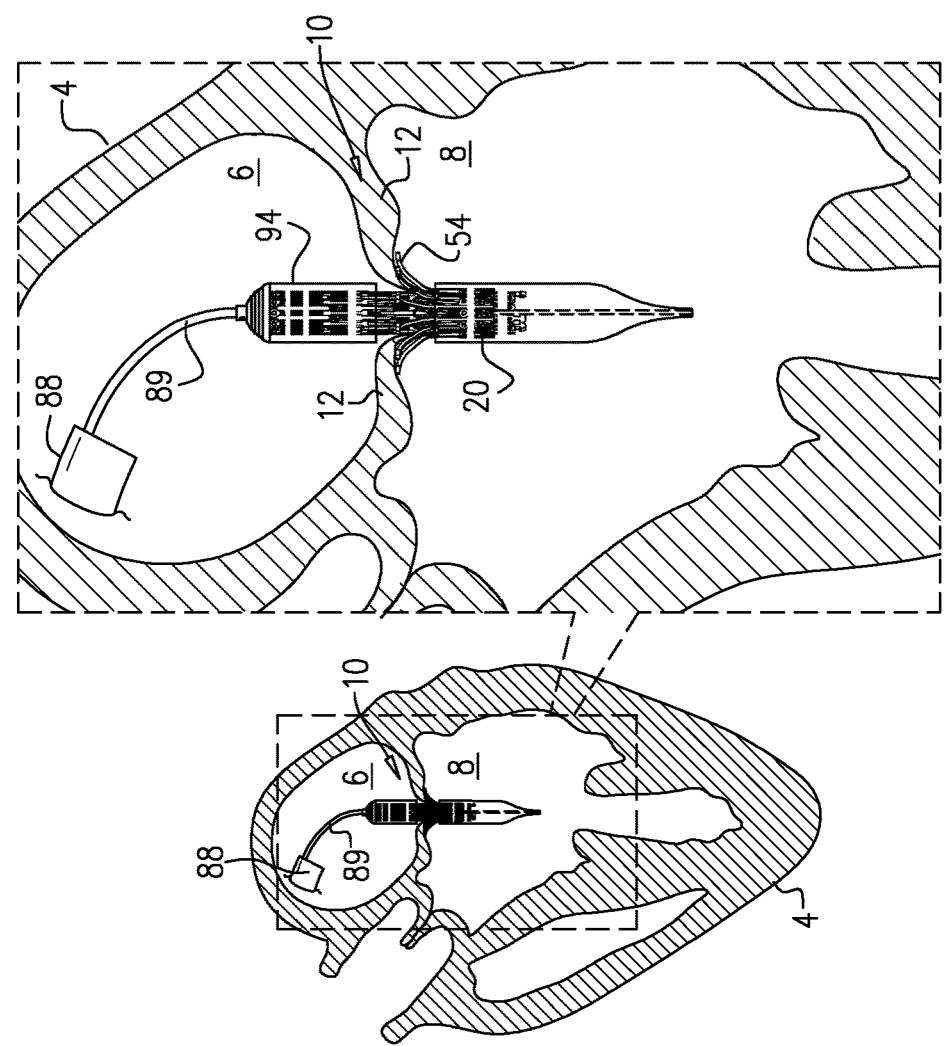

Due to the configurations described herein, the distance by which flanges 54 move with respect to (e.g., toward, or toward-and-beyond) upstream support portion 40 (e.g., arms 46 thereof), is typically greater than the reduction in the overall height of tubular portion 32 (e.g., more than 20 percent greater, such as more than 30 percent greater, such as more than 40 percent greater). That is, implant 20 comprises:

a valve frame (30) that comprises a tubular portion (32) that circumscribes a longitudinal axis (ax1) of the valve frame so as to define a lumen (38) along the axis, the tubular portion having an upstream end (34), a downstream end (36), a longitudinal length therebetween, and a diameter (e.g., d1 or d2) transverse to the longitudinal axis;

a valve member (58), coupled to the tubular portion, disposed within the lumen, and arranged to provide unidirectional upstream-to-downstream flow of blood through the lumen;

an upstream support portion (40), coupled to the tubular portion; and an outer frame (60), coupled to the tubular portion, and comprising a tissue-engaging flange (54), wherein:

the implant has a first state (e.g., as shown in FIG. 2D and FIG. 4D) and a second state (e.g., as shown in FIG. 2E and FIG. 4E), in both the first state and the second state, (i) the upstream support portion extends radially outward from the tubular portion, and (ii) the tissue-engaging flange extends radially outward from the tubular portion, and the tubular portion, the upstream support portion, and the outer frame are arranged such that transitioning of the implant from the first state toward the second state:

increases the diameter of the tubular portion by a diameter-increase amount (e.g., the difference between d1 and d2), decreases the length of the tubular portion by a length-decrease amount (e.g., the difference between d22 and d23), and moves the flange a longitudinal distance with respect to (e.g., toward or toward-and-beyond) the upstream support portion (e.g., the difference between d3 and d4), this distance being greater than the length-decrease amount.

As shown in the figures, valve frame 30 is typically coupled to outer frame 60 by coupling between (i) a valve-frame coupling element 31 defined by valve frame 30, and (ii) an outer-frame coupling element 61 defined by outer frame 60 (e.g., an outer-frame coupling element is coupled to end 74 of each strut). Typically, elements 31 and 61 are fixed with respect to each other. Each coupling point 52 is thereby typically defined as the point at which a valve-frame coupling element and a corresponding outer-frame coupling element 61 are coupled (e.g., are fixed with respect to each other). For some applications, and as shown, elements 31 and 61 are eyelets configured to be coupled together by a connector, such as a pin or a stitch (e.g., a suture). The fixing of elements 31 and 61 with respect to each other may be achieved by welding, soldering, crimping, stitching (e.g., suturing), gluing, or any other suitable technique.

Typically, and as shown, valve-frame coupling elements 31 are defined by tubular portion 32, and are disposed circumferentially around central longitudinal axis ax1. Outer-frame coupling elements 61 are coupled to ring 66 (or defined by frame 60, such as by ring 66) at respective peaks 64.

As shown (e.g., in FIGS. 2A-E), valve frame 30 (e.g., tubular portion 32 thereof) and outer frame 60 (e.g., ring 66 thereof) are arranged in a close-fitting coaxial arrangement, in both the expanded and compressed states of frame assembly 22. Ignoring spaces due to the cellular structure of the frames, a radial gap d19 between valve frame 30 (e.g., tubular portion 32 thereof) and outer frame 60 (e.g., ring 66 thereof) is typically less than 2 mm (e.g., less than 1 mm), in both the compressed and expanded states, and during the transition therebetween. This is facilitated by the coupling between frames 30 and 60, and the behavior, described hereinabove, of frame 60 in response to changes in the diameter of tubular portion 32 (e.g., rather than solely due to delivery techniques and/or tools). For some applications, more than 50 percent (e.g., more than 60 percent) of ring 66 is disposed within 2 mm of tubular portion 32 in both the compressed and expanded states, and during the transition therebetween. For some applications, more than 50 percent (e.g., more than 60 percent) of outer frame 60, except for flanges 54, is disposed within 2 mm of tubular portion 32 in both the compressed and expanded states, and during the transition therebetween.

The structural changes to frame assembly 22 (e.g., to outer frame 60 thereof) are described hereinabove as they occur during (e.g., as a result of) expansion of the frame assembly (in particular tubular portion 32 thereof). This is the natural way to describe these changes because, as described hereinbelow with respect to FIGS. 4A-6, assembly 22 is in its compressed state during percutaneous delivery to the implant site, and is subsequently expanded. However, the nature of implant 20 may be further understood by describing structural changes that occur during compression of the frame assembly (e.g., a transition from the expanded state in FIG. 2E to the intermediate state in FIG. 2D), in particular tubular portion 32 thereof (including if tubular portion 32 were compressed by application of compressive force to the tubular portion, and not to frame 60 except via the tubular portion pulling frame 60 radially inward). Such descriptions may also be relevant because implant 20 is typically compressed (i.e., "crimped") soon before its percutaneous delivery, and therefore these changes may occur while implant 20 is in the care of the operating physician.

For some applications, the fixation of peaks 64 to respective sites of tubular portion 32 is such that compression of the tubular portion from its expanded state toward its compressed state such that the respective sites of the tubular portion pull the peaks radially inward via radially-inward tension on coupling points 52: (i) reduces a circumferential distance between each of the coupling points and its adjacent coupling points (e.g., from d9 to d8), and (ii) increases the amplitude of the pattern of ring 66 (e.g., from d21 to d20).

For some applications, the fixation of outer-frame coupling elements 61 to valve-frame coupling elements 31 is such that compression of tubular portion 32 from its expanded state toward its compressed state such that the valve-frame coupling elements pull the outer-frame coupling elements radially inward: (i) reduces a circumferential distance between each of the outer-frame coupling elements and its adjacent outer-frame coupling elements (e.g., from d9 to d8), and (ii) increases the amplitude of the pattern of ring 66 (e.g., from d21 to d20).

For some applications, the fixation of peaks 64 to the respective sites of tubular portion 32 is such that compression of the tubular portion from its expanded state toward its compressed state (i) pulls the peaks radially inward via radially-inward pulling of the respective sites of the tubular portion on the peaks, (ii) reduces a circumferential distance between each of coupling points 52 and its adjacent coupling points (e.g., from d9 to d8), and (iii) increases the amplitude of the pattern of ring 66 (e.g., from d21 to d20), without increasing radial gap d19 between valve frame 30 (e.g., tubular portion 32 thereof) and the ring by more than 1.5 mm.

For some applications, the fixation of outer-frame coupling elements 61 with respect to valve-frame coupling elements 31 is such that compression of tubular portion 32 from its expanded state toward its compressed state (i) pulls outer-frame coupling elements 61 radially inward via radially-inward pulling of valve-frame coupling elements 31 on outer-frame coupling elements 61, (ii) reduces a circumferential distance between each of the outer-frame coupling elements and its adjacent outer-frame coupling elements (e.g., from d9 to d8), and (iii) increases the amplitude of the pattern of ring 66 (e.g., from d21 to d20), without increasing radial gap d19 between valve frame 30 (e.g., tubular portion 32 thereof) and the ring by more than 1.5 mm.

Reference is made to FIGS. 4A-F, which are schematic illustrations of implantation of implant 20 at a native valve 10 of a heart 4 of a subject, in accordance with some applications of the invention. Valve 10 is shown as a mitral valve of the subject, disposed between a left atrium 6 and a left ventricle 8 of the subject. However, implant 20 may be implanted at another heart valve of the subject, mutatis mutandis. Similarly, although FIGS. 4A-F show implant 20 being delivered transseptally via a sheath 88, the implant may alternatively be delivered by any other suitable route, such as transatrially, or transapically.

Implant 20 is delivered, in its compressed state, to native valve 10 using a delivery tool 89 that is operable from outside the subject (FIG. 4A). Typically, implant 20 is delivered within a delivery capsule 90 of tool 89, which retains the implant in its compressed state. A transseptal approach, such as a transfemoral approach, is shown. Typically, implant 20 is positioned such that at least flanges 54 are disposed downstream of the native valve (i.e., within ventricle 8). At this stage, frame assembly 22 of implant 20 is as shown in FIG. 2A.

Subsequently, flanges 54 are allowed to protrude radially outward, as described hereinabove, e.g., by releasing them from capsule 90 (FIG. 4B). For example, and as shown, capsule 90 may comprise a distal capsule-portion 92 and a proximal capsule-portion 94, and the distal capsule-portion may be moved distally with respect to implant 20, so as to expose flanges 54. At this stage, frame assembly 22 of implant 20 is as shown in FIG. 2B.

Subsequently, implant 20 is moved upstream, such that upstream support portion 40, in its compressed state, is disposed upstream of leaflets 12 (i.e., within atrium 6). For some applications, the upstream movement of implant 20 causes flanges 54 to engage leaflets 12. However, because of the relatively large distance d3 provided by implant 20 (described hereinabove), for some applications it is not necessary to move the implant so far upstream that flanges 54 tightly engage leaflets 12 and/or pull the leaflets upstream of the valve annulus. Upstream support portion 40 is then allowed to expand such that it protrudes radially outward, as described hereinabove, e.g., by releasing it from capsule 90 (FIG. 4D). For example, and as shown, proximal capsule-portion 94 may be moved proximally with respect to implant 20, so as to expose upstream support portion 40. At this stage, frame assembly 22 of implant 20 is as shown in FIG. 2D, in which: (i) distance d3 exists between upstream support portion 40 and flanges 54, (ii) the flanges have span d15, (iii) the upstream support portion has span d17, and (iv) tubular portion 32 has diameter d1.

Typically, expansion of frame assembly 22 is inhibited by distal capsule-portion 92 (e.g., by inhibiting expansion of tubular portion 32), and/or by another portion of delivery tool 89 (e.g., a portion of the delivery tool that is disposed within lumen 38).

Subsequently, implant 20 is allowed to expand toward its expanded state, such that tubular portion 32 widens to diameter d2, and the distance between upstream support portion 40 and flanges 54 reduces to distance d4 (FIG. 4E). This sandwiches tissue of valve 10 (typically including annular tissue and/or leaflets 12) between upstream support portion 40 and flanges 54, thereby securing implant 20 at the valve. FIG. 4F shows delivery capsule 90 having been removed from the body of the subject, leaving implant 20 in place at valve 10.

As described hereinabove, implant 20 is configured such that when tubular portion 32 is expanded, flanges 54 and upstream support portion 40 move a relatively large distance toward each other. This enables distance d3 to be relatively large, while distance d4 is sufficiently small to provide effective anchoring. As also described hereinabove, implant 20 is configured such that flanges 54 and upstream support portion 40 can extend radially outward a relatively large distance while tubular portion 32 remains compressed. It is hypothesized that for some applications, these configurations (independently and/or together) facilitate effective anchoring of implant 20, by facilitating placement of a relatively large proportion of valve tissue (e.g., leaflets 12) between the flanges and the upstream support portion prior to expanding tubular portion 32 and sandwiching the valve tissue.

It is further hypothesized that the relatively great radially-outward extension of flanges 54 and upstream support portion 40 prior to expansion of tubular portion 32, further facilitates the anchoring/sandwiching step by reducing radially-outward pushing of the valve tissue (e.g., leaflets 12) during the expansion of the tubular portion, and thereby increasing the amount of valve tissue that is sandwiched.

It is yet further hypothesized that this configuration of implant 20 facilitates identifying correct positioning of the implant (i.e., with upstream support portion 40 upstream of leaflets 12 and flanges 54 downstream of the leaflets) prior to expanding tubular portion 32 and sandwiching the valve tissue.

As shown in FIG. 1A, for some applications, in the expanded state of frame assembly 22, implant 20 defines a toroidal space 49 between flanges 54 and upstream support portion 40 (e.g., a space that is wider than distance d4). For example, space 49 may have a generally triangular cross-section. It is hypothesized that for some such applications, in addition to sandwiching tissue of the native valve between upstream support portion 40 and flanges 54 (e.g., the tips of the flanges), space 49 advantageously promotes tissue growth therewithin (e.g., between leaflet tissue and covering 23), which over time further secures implant 20 within the native valve.

Figure 5:
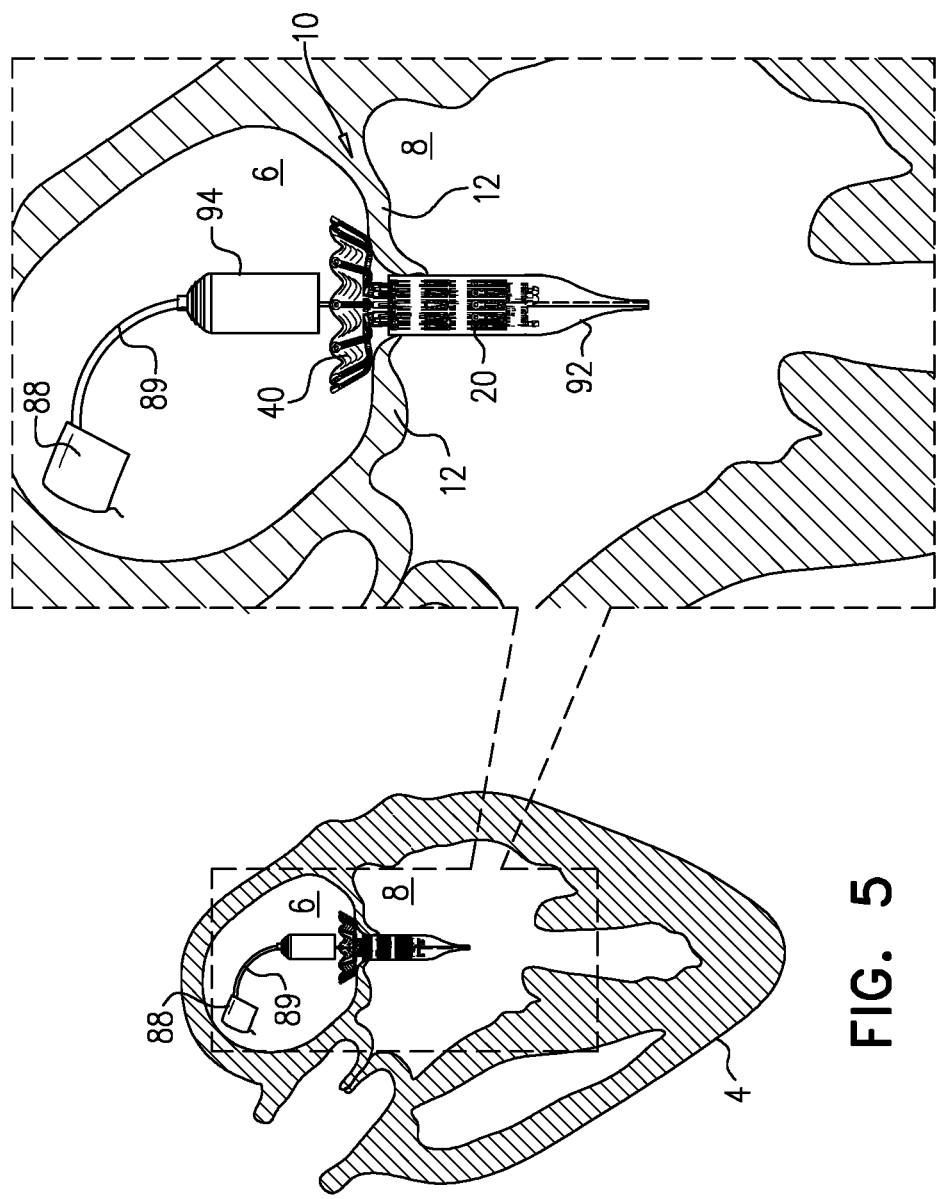
FIG. 5 is a schematic illustration of a step in the implantation of the implant, in accordance with some applications of the invention.

Reference is now made to FIG. 5, which is a schematic illustration of a step in the implantation of implant 20, in accordance with some applications of the invention. Whereas FIGS. 4A-F show an implantation technique in which flanges 54 are expanded prior to upstream support portion 40, for some applications the upstream support portion is expanded prior to the flanges. FIG. 5 shows a step in such an application.

Reference is again made to FIGS. 2A-5. As noted hereinabove, implant 20 may be implanted by causing flanges 54 to radially protrude before causing upstream support portion 40 to radially protrude, or may be implanted by causing the upstream support portion to protrude before causing the flanges to protrude. For some applications, implant 20 is thereby configured to be deliverable in a downstream direction (e.g., transseptally, as shown, or transapically) or in an upstream direction (e.g., transapically or via the aortic valve). Thus, for some applications, an operating physician may decide which delivery route is preferable for a given application (e.g., for a given subject, and/or based on available equipment and/or expertise), and implant 20 is responsively prepared for the chosen delivery route (e.g., by loading the implant into an appropriate delivery tool).

It is to be noted that for some applications, downstream delivery of implant 20 may be performed by expanding flanges 54 first (e.g., as shown in FIGS. 4A-F) or by expanding upstream support portion 40 first (e.g., as shown in FIG. 5). Similarly, for some applications upstream delivery of implant 20 may be performed by upstream support portion 40 first, or by expanding flanges 54 first.

Figure 6:
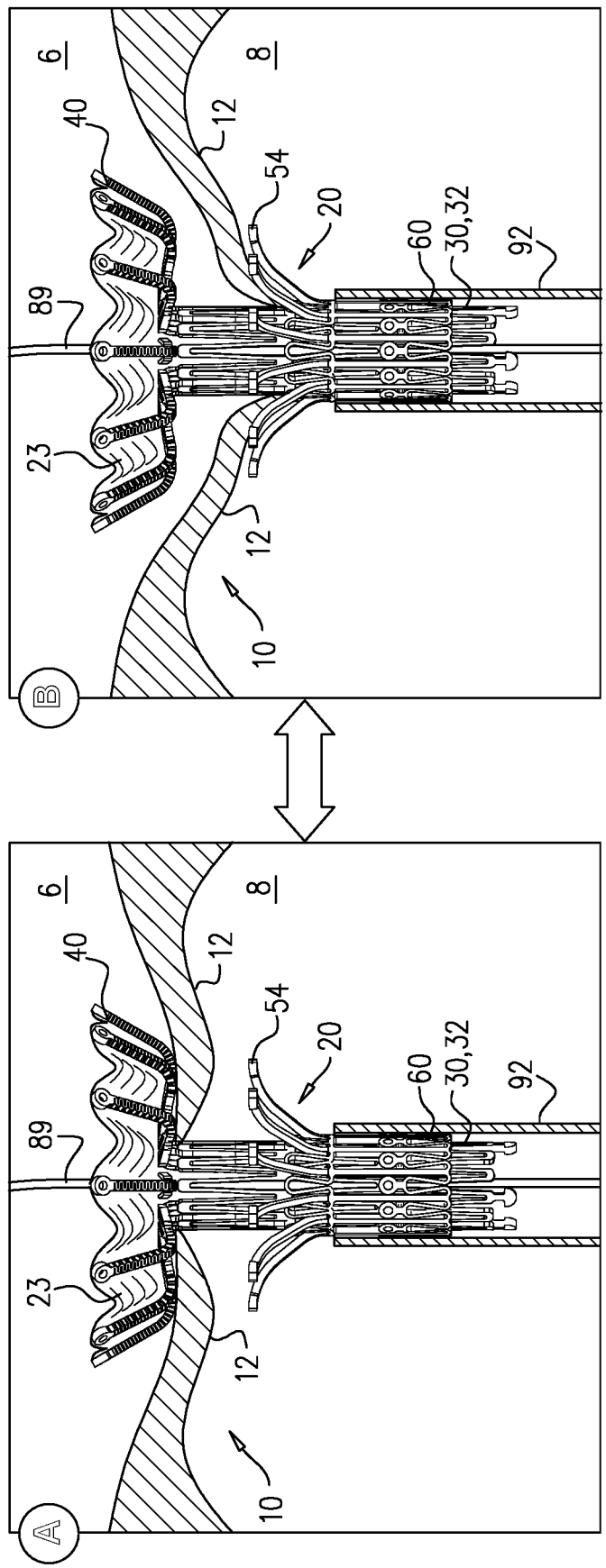
FIG. 6 is a schematic illustration of the implant, in accordance with some applications of the invention.
Figure 8B:
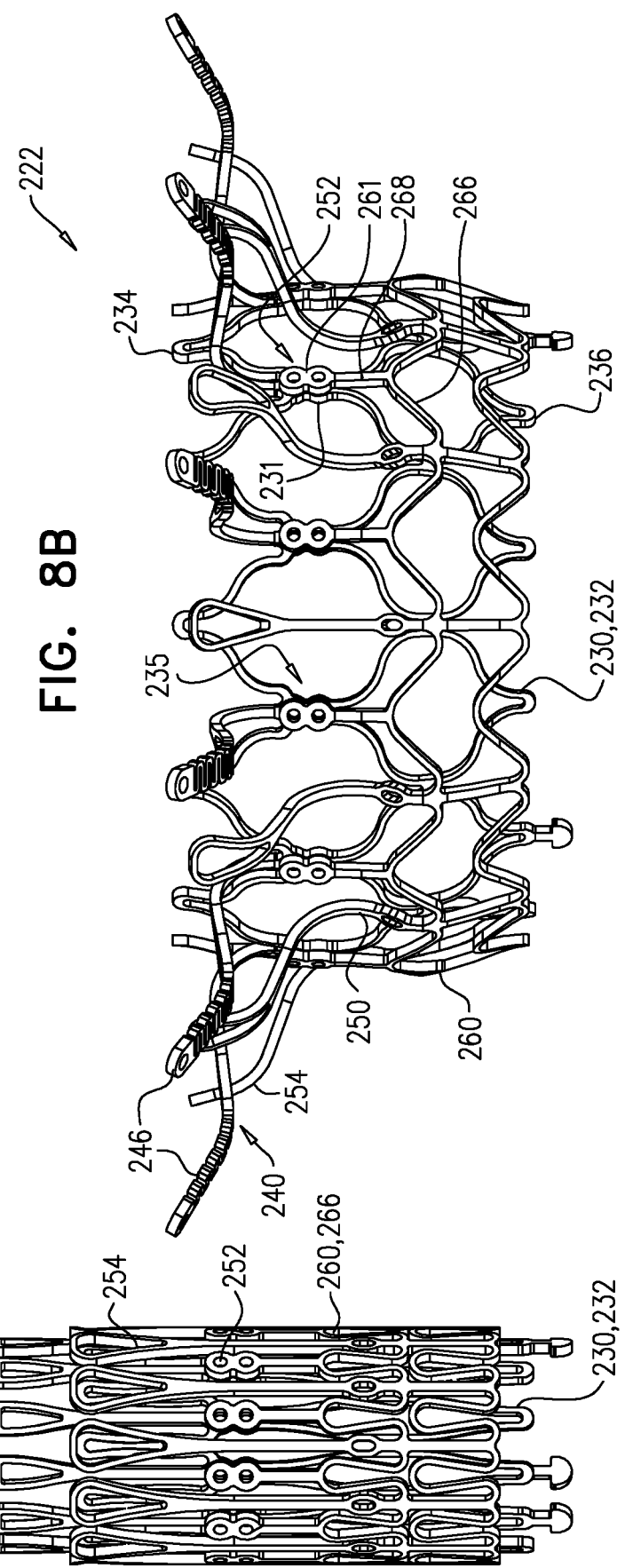
Figure 8A:
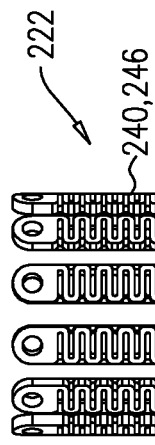

Reference is now made to FIG. 6, which is a schematic illustration of implant 20, in the state and position shown in FIG. 4D, in accordance with some applications of the invention. For some applications, while implant 20 is in the state and position shown in FIG. 4D, leaflets 12 of valve 10 are able to move, at least in part in response to beating of the heart. Frame (A) shows leaflets 12 during ventricular systole, and frame (B) shows the leaflets during ventricular diastole. For some such applications, blood is thereby able to flow from atrium 6 to ventricle 8, between leaflets 12 and implant 20. It is hypothesized that this advantageously facilitates a more relaxed implantation procedure, e.g., facilitating retaining of implant 20 in this state and position for a duration of greater than 8 minutes. During this time, imaging techniques may be used to verify the position of implant 20, and/or positioning of leaflets 12 between upstream support portion 40 and flanges 54.

Reference is made to FIGS. 7A-B and 8A-B, which are schematic illustrations of frame assemblies 122 and 222 of respective implants, in accordance with some applications of the invention. Except where noted otherwise, frame assemblies 122 and 222 are typically identical to frame assembly 22, mutatis mutandis. Elements of frame assemblies 122 and 222 share the name of corresponding elements of frame assembly 22. Additionally, except where noted otherwise, the implants to which frame assemblies 122 and 222 belong are similar to implant 20, mutatis mutandis.

Frame assembly 122 comprises (i) a valve frame 130 that comprises a tubular portion 132 and an upstream support portion 140 that typically comprises a plurality of arms 146, and (ii) an outer frame (e.g., a leg frame) 160 that circumscribes the valve frame, and comprises a plurality of legs 150 that each comprise a tissue-engaging flange 154. Typically, outer frame 160 comprises a ring 166 to which legs 150 are coupled. Ring 166 is defined by a pattern of alternating peaks and troughs, the peaks being fixed to frame 130 at respective coupling points 152, e.g., as described hereinabove for frame assembly 22, mutatis mutandis.

Frame assembly 222 comprises (i) a valve frame 230 that comprises a tubular portion 232 and an upstream support portion 240 that typically comprises a plurality of arms 246, and (ii) an outer frame (e.g., a leg frame) 260 that circumscribes the valve frame, and comprises a plurality of legs 250 that each comprise a tissue-engaging flange 254. Typically, outer frame 260 comprises a ring 266 to which legs 250 are coupled. Ring 266 is defined by a pattern of alternating peaks and troughs, the peaks being fixed to frame 230 at respective coupling points 252, e.g., as described hereinabove for frame assembly 22, mutatis mutandis.

Whereas arms 46 of frame assembly 22 are shown as extending from upstream end 34 of tubular portion 32, arms 146 and 246 of frame assemblies 122 and 222, respectively, extend from sites further downstream. (This difference may also be made to frame assembly 22, mutatis mutandis.) Tubular portions 32, 132 and 232 are each defined by a repeating pattern of cells that extends around the central longitudinal axis. Typically, and as shown, tubular portions 32, 132 and 232 are each defined by two stacked, tessellating rows of cells. In the expanded state of each tubular portion, these cells are typically narrower at their upstream and downstream extremities than midway between these extremities. For example, and as shown, the cells may be roughly diamond or astroid in shape. In frame assembly 22, each arm 46 is attached to and extends from a site 35 that is at the upstream extremity of cells of the upstream row. In contrast, in frame assemblies 122 and 222, each arm 146 or 246 is attached to and extends from a site 135 (assembly 122) or 235 (assembly 222) that is at the connection between two adjacent cells of the upstream row (alternatively described as being at the upstream extremity of cells of the downstream row).

It is hypothesized by the inventors that this lower position of the arms, while maintaining the length of the lumen of the tubular portion, advantageously reduces the distance that the tubular portion (i.e., the downstream end thereof) extends into the ventricle of the subject, and thereby reduces a likelihood of inhibiting blood flow out of the ventricle through the left ventricular outflow tract. It is further hypothesized that this position of the arms reduces radial compression of the tubular portion by movement of the heart, due to greater rigidity of the tubular portion at sites 135 and 235 (which is supported by two adjacent cells) than at site 35 (which is supported by only one cell).

As shown, in the expanded state of frame assemblies 22, 122 and 222, the legs (50, 150 and 250, respectively) are circumferentially staggered with the arms of the upstream support portion (46, 146 and 246, respectively). This allows the legs to move in an upstream direction between the arms during expansion of the tubular portion (32, 132 and 232, respectively), facilitating application of greater sandwiching force on tissue of the native valve. The lower position of the arms of assemblies 122 and 222 includes circumferentially shifting the position of the arms by the width of half a cell. In order to maintain the circumferential staggering of the arms and legs, rings 166 and 266 (and thereby legs 150 and 250) are circumferentially shifted correspondingly. As a result, whereas the peaks of ring 66 generally align with connections between adjacent cells of the downstream row of cells of tubular portion 32 (and are fixed to these sites), the peaks of rings 166 and 266 are generally aligned midway between these sites (i.e., at spaces of the cellular structure of the tubular portion). Appendages 168 (for assembly 122) or 268 (for assembly 222) facilitate fixing of the peak with respect to the tubular structure.

For assembly 122, appendages 168 are defined by valve frame 130 (e.g., by tubular portion 132 thereof) and extend (in a downstream direction) to the peaks of ring 166, to which they are fixed. For example, each appendage 168 may define a valve-frame coupling element 131 that is fixed to a respective outer-frame coupling element 161 defined by outer frame 260. Typically, appendages 168 extend from sites 135. Typically, appendages 168 are integral with tubular portion 132 and/or in-plane with the tubular portion (e.g., are part of its tubular shape).

For assembly 222, appendages 268 are defined by outer frame 260, and extend (e.g., in an upstream direction) from the peaks of ring 266. Typically, appendages 268 extend to sites 235, to which they are fixed. For example, each appendage 268 may define an outer-frame coupling element 261 that is fixed to a respective valve-frame coupling element 231 defined by valve frame 230 (e.g., by tubular portion 232 thereof). Typically, appendages 268 are integral with outer frame 260 and/or in-plane with adjacent portions of outer frame 260, such as ring 266.

Therefore, frame assembly 122 defines a hub at site 135, and frame assembly 222 defines a hub at site 235. For some applications, apparatus therefore comprises:
  a plurality of prosthetic valve leaflets; and
  a frame assembly, comprising:
    a tubular portion (132 or 232) defined by a repeating pattern of cells, the tubular portion extending circumferentially around longitudinal axis ax1 so as to define a longitudinal lumen, the prosthetic valve leaflets coupled to the inner frame and disposed within the lumen;
    an outer frame (160 or 260), comprising a plurality of legs (150 or 250), distributed circumferentially around the tubular portion, each leg having a tissue-engaging flange (154 or 254);
    an upstream support portion (140 or 240) that comprises a plurality of arms (146 or 246) that extend radially outward from the tubular portion; and a plurality of appendages (168 or 268), each having a first end that defines a coupling element (161 or 261) via which the tubular portion is coupled to the outer frame, and a second end;
  wherein the frame assembly defines a plurality of hubs (135 or 235), distributed circumferentially around the longitudinal axis on a plane that is transverse to longitudinal axis ax1, each hub defined by convergence and connection of, (i) two adjacent cells of the tubular portion, (ii) an arm of the plurality of arms, and (iii) an appendage of the plurality of appendages.

Reference is made to FIGS. 9A-C, which are schematic illustrations of an implant 320 comprising a frame assembly 322, in accordance with some applications of the invention. Except where noted otherwise, frame assembly 322 is identical to frame assembly 122, and implant 300 is identical to the implant to which frame assembly 122 belongs, mutatis mutandis. FIG. 9A is a side-view of implant 320, and FIG. 9B is an isometric bottom-view of the implant.

Frame assembly 122 comprises (i) a valve frame 330 that comprises a tubular portion 332 and an upstream support portion 340 that typically comprises a plurality of arms 346, and (ii) an outer frame (e.g., a leg frame) 360 that circumscribes the valve frame, and comprises a plurality of legs 350 that each comprise a tissue-engaging flange 354. Typically, outer frame 360 comprises a ring 366 to which legs 350 are coupled. Ring 366 is defined by a pattern of alternating peaks and troughs, the peaks being fixed to frame 330 at respective coupling points 352, e.g., as described hereinabove for frame assembly 22 and/or frame assembly 122, mutatis mutandis.

Frame assembly 322 comprises an annular upstream support portion 340 that has an inner portion 342 that extends radially outward from the upstream portion (e.g., the upstream end) of tubular portion 332. Upstream support portion 340 further comprises one or more fabric pockets 344 disposed circumferentially around inner portion 342, each pocket of the one or more pockets having an opening that faces a downstream direction (i.e., generally toward the downstream end of implant 320). In the figures, upstream support portion 340 has a single toroidal pocket 344 that extends circumferentially around inner portion 342.

Typically, a covering 323 (e.g., similar to covering 23, described hereinabove, mutatis mutandis) is disposed over arms 346, thereby forming pocket 344. Further typically, arms 346 are shaped to form pocket 344 from covering 323. For example, and as shown, arms 346 may curve to form a hook-shape.

For some applications, portion 340 has a plurality of separate pockets 344, e.g., separated at arms 346. For some such applications, covering 323 is loosely-fitted (e.g., baggy) between radially-outward parts of arms 346, e.g., compared to inner portion 342, in which the covering is more closely-fitted between radially-inward parts of the arms.

FIG. 9C shows implant 320 implanted at native valve 10. Pocket 344 is typically shaped and arranged to billow in response to perivalvular flow 302 of blood in an upstream direction. If ventricular systole forces blood in ventricle 8 between implant 320 and native valve 10, that blood inflates pocket 344 and presses it (e.g., covering 323 and/or the radially-outward part of arm 346) against tissue of atrium 6 (e.g., against the atrial wall), thereby increasing sealing responsively. It is hypothesized by the inventors that the shape and orientation of pocket 344 (e.g., the hook-shape of arms 346) facilitates this pressing radially-outward in response to the pocket's receipt of upstream-flowing blood.

Pocket(s) 344 may be used in combination with any of the implants described herein, mutatis mutandis.

Figure 10:
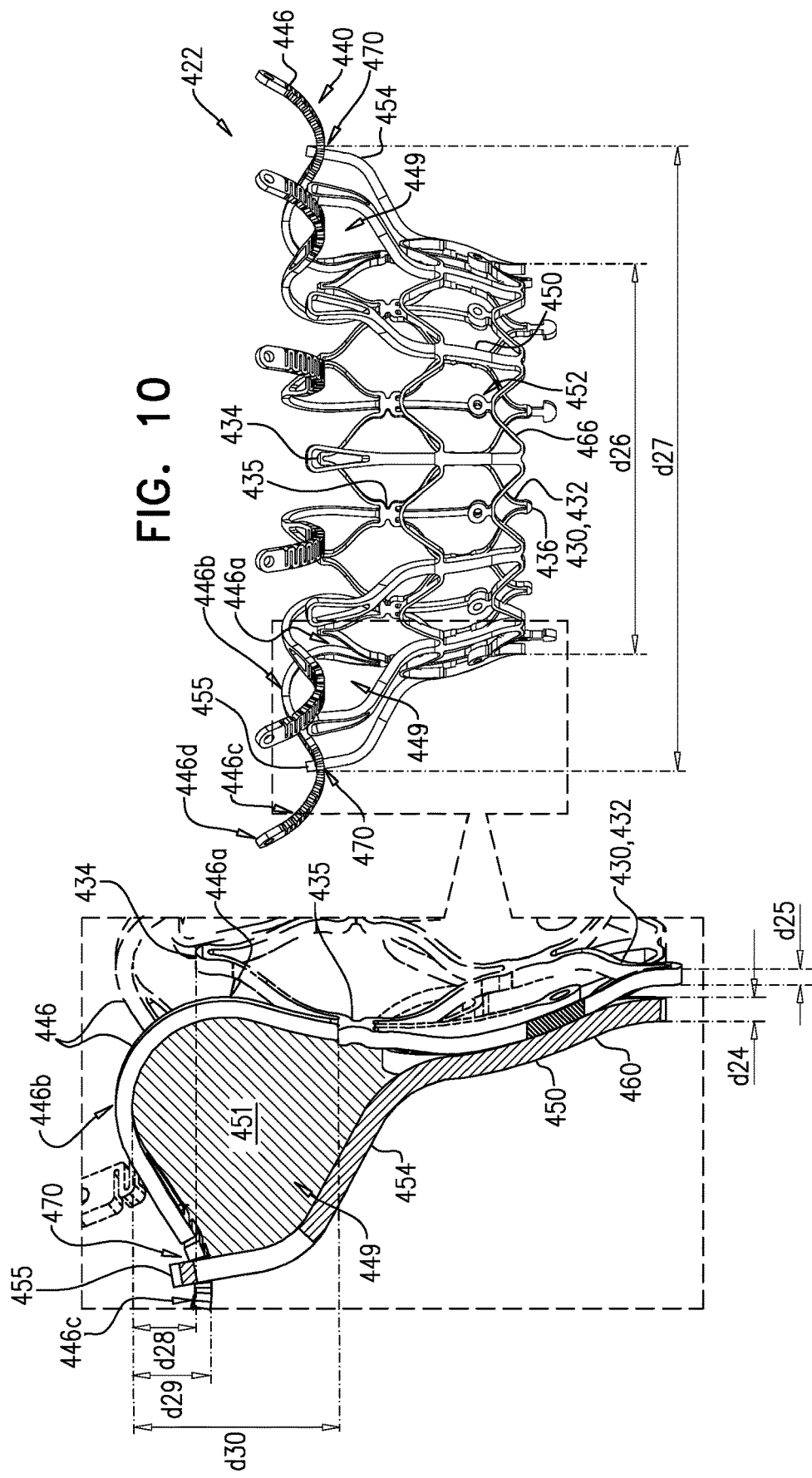
FIG. 10 is a schematic illustration of a frame assembly of an implant, in accordance with some applications of the invention.

Reference is now made to FIG. 10, which is a schematic illustration of a frame assembly 422 of an implant, in accordance with some applications of the invention. Except where noted otherwise, frame assembly 422 is typically identical to frame assembly 122, mutatis mutandis. Elements of frame assembly 422 share the name of corresponding elements of frame assembly 122. Additionally, except where noted otherwise, the implant to which frame assembly 422 belongs is similar to implant the other implants described herein (e.g., implant 20), mutatis mutandis. FIG. 10 shows frame assembly 422 in an expanded state (e.g., in the absence of external deforming forces, such as those provided by a delivery tool during implantation, or by heart tissue after implantation).

Frame assembly 422 comprises (i) a valve frame (e.g., an inner frame) 430 that comprises a tubular portion 432 and an upstream support portion 440 that typically comprises a plurality of radial arms 446, and (ii) an outer frame (e.g., a leg frame) 460 that circumscribes the valve frame, and comprises a plurality of legs 450 that each comprise a tissue-engaging flange 454. Typically, outer frame 460 comprises a ring 466 to which legs 450 are coupled. Ring 466 is defined by a pattern of alternating peaks and troughs, the peaks being fixed to frame 430 at respective coupling points 452, e.g., as described hereinabove for frame assemblies 22 and 122, mutatis mutandis. Tubular portion 432 has a diameter d26 (corresponding to diameter d2 of implant 20), and a transverse cross-sectional area that is a function of diameter d26.

Similarly to other frame assemblies described herein, in the expanded state of frame assembly 422, legs 450 are circumferentially staggered with arms 446 of upstream support portion 440. This allows the legs (e.g., flanges 454 thereof) to move in an upstream direction between the arms during deployment of the implant (although the presence of heart tissue typically reduces the amount by which flanges 454 move between arms 446). FIG. 10 shows frame assembly 422 in its expanded state, in which upstream support portion 440 (e.g., arms 446) and flanges 454 extend radially outward from tubular portion 432, and intersect at an intersection 470. Opposite intersections 470 define an intersect diameter d27. Typically, flanges 454 extend radially outward from the tubular portion and toward the upstream support portion 440 (i.e., outward and in an upstream direction). A toroidal space 449 is defined between flanges 454, upstream support portion 440, and tubular portion 432, the toroidal space circumscribing the tubular portion.

As described hereinabove with respect to other implants, the implant to which frame assembly 422 belongs is secured at the native valve by sandwiching heart tissue (e.g., leaflets 12 and/or the valve annulus) between upstream support portion 440 and flanges 54 (e.g., within space 449). Typically, leaflets 12 are trapped in space 449. Space 449 is dimensioned to be sufficiently large to accommodate leaflets 12, because it has been observed by the inventors that if space 449 is too small, the implant tends to become secured to tissue that is suboptimally close to the middle of the native valve orifice (e.g., closer to the free edges of the leaflets), and to sit in a position that is suboptimally downstream (i.e., into ventricle 8). Additionally, space 449 is dimensioned to be sufficiently small to accommodate leaflets 12 snugly, because it has been observed by the inventors that if space 449 is sufficiently small that the leaflets fill the space well (typically folding or bunching up within the space), sandwiching forces are applied to leaflet tissue throughout space 449. In contrast, if space 449 is too large, sandwiching forces may be applied to the leaflets only at or close to intersections 470, reducing the effectiveness of anchoring, and/or increasing a likelihood of damaging the tissue at or close to the intersections.

It is hypothesized by the inventors that an optimal size of space 449 (i.e., a size that is sufficiently large to accommodate leaflets 12, but sufficiently small to do so snugly) is achieved when the space has a cross-sectional area 451 that is 5-10 percent (e.g., 5-8 percent, such as 6-7 percent or 6.5-7.5 percent) of the transverse cross-sectional area of tubular portion 432. It is further hypothesized that this relative size is optimal across implants that have tubular portions of different diameters. For example:

For an implant in which diameter d26 is 25 mm, an optimally-sized cross-sectional area 451 may be 25-40 (e.g., about 35) mm^2.

For an implant in which diameter d26 is 27 mm, an optimally-sized cross-sectional area 451 may be 30-45 (e.g., about 40) mm^2.

For an implant in which diameter d26 is 29 mm, an optimally-sized cross-sectional area 451 may be 35-50 (e.g., about 45) mm^2.

This optimal relative size range of area 451 is hypothesized by the inventors to apply to implants that have tubular portions that are narrower or wider than the above examples (e.g., 23 mm or 31 mm diameter).

For some applications, implants of different diameters d26 are provided, and each of the implants has a cross-sectional area 451 that is 5-10 percent (e.g., 5-8 percent, such as 6-7 percent or 6.5-7.5 percent) of the transverse cross-sectional area of the tubular portion 432 of the implant. For example, the tubular portion 432 of one of the implants may have a have transverse cross-sectional area that is at least 15 percent (e.g., at least 30 percent) greater than another one of the implants.

Tubular portion 432 has an upstream end 434 and a downstream end 436. Similarly to frame assembly 122, arms 446 are attached to and extend from sites 435 that are downstream of upstream end 434, e.g., at the connection between two adjacent cells of the upstream row of cells of tubular portion 432 (alternatively described as being at the upstream extremity of cells of the downstream row of cells).

Progressively lateral portions of each arm 446 define, respectively: (i) an ascending portion 446a that extends in an upstream direction past upstream end 434 of tubular portion 432 (e.g., by a distance d28), (ii) an arch portion 446b that curves in a downstream direction to form an arch (portion 446b may alternatively be described as being convex in an upstream direction), and (iii) a lateral portion 446c that curves in an upstream direction. For some applications, in the absence of tissue, arch portion 446b curves in the downstream direction as far as (and typically past) tips 455 of flanges 454 (i.e., at the arch portion, each arm 446 extends below (i.e., further downstream than) adjacent tips 455). For some applications, and as shown, intersections 470 are generally close to where arms 446 begin to curve upstream.

A height d29 is the height, along the central longitudinal axis of the implant, between (i) the crest of arch portion 446b, and (ii) intersection 470. For some applications, height d29 is 0.5-3.5 mm (e.g., 1.8-2.6 mm).

A height d30 is the height, along the central longitudinal axis of the implant, between (i) the crest of arch portion 446b, and (ii) site 435. For some applications, height d30 is 4-7.5 mm (e.g., 5.2-6.5 mm).

It is to be noted, therefore, that for some applications, arms 446 extend (i) radially outward and above (a) upstream end 434 and (b) the tips of flanges 454, and then (ii) further radially outward and below (a) upstream end 434 and/or (b) the tips of flanges 454 (i.e., toward the flanges). The above configuration of arm 46 increases the size of toroidal space 449 (compared to a similar arm in which d28 and/or d29 are smaller), e.g., providing an optimal cross-sectional area 451, as described hereinabove. (In contrast, for example, in frame assemblies 122 and 222, the arms do not have arch portions that extend above (i) the upstream end of the respective tubular portion, or (ii) the tips of the respective flanges. Although the lateral portions of these arms do extend upwardly, the lateral portions are radially outward of the flanges, and therefore do not increase the cross-sectional area of the toroidal space defined by these frame assemblies.)

For some applications, an end 446d (i.e., the lateral extremity) of arm 446 is disposed further in an upstream direction than arch portion 446b.

For some applications, the outer stent frame (e.g., leg frame) 460 has a radial thickness d24 (i.e., a thickness measured along an axis that extends radially outward from the central longitudinal axis of the implant) that is greater than a radial thickness d25 of inner stent frame (e.g., valve frame) 430. That is, the outer stent frame is radially thicker than the inner stent frame. This is typically achieved by cutting (e.g., laser cutting) the inner stent frame from a nitinol tube that has a first wall thickness (e.g., equal to d25), and cutting the outer stent frame from another nitinol tube that has a second, greater wall thickness (e.g., equal to d24). However, other methods of manufacture, including 3D printing, may be used.

For some applications, thickness d24 is at least 10 percent (e.g., at least 20 percent, such as at least 30 percent) and/or no more than 80 percent (e.g., no more than 50 percent) greater than thickness d25. For some applications, thickness d24 is 0.6-0.8 mm (e.g., 0.7-0.75 mm, e.g., 0.71-0.73 mm, such as 0.72 mm), and thickness d25 is 0.45-0.65 mm (e.g., 0.5-0.55 mm, e.g., 0.52-0.54 mm, such as 0.53 mm).

Having the outer stent frame (e.g., leg frame) be radially thicker than inner stent frame (e.g., valve frame) may be applied to the other frame assemblies described herein, mutatis mutandis.

There is therefore provided, in accordance with some applications of the invention, apparatus comprising:

(1) a frame assembly, transluminally advanceable to the heart, and comprising:

(i) an inner stent frame that defines a tubular portion; and (ii) an outer stent frame that defines a ring that is coupled to the inner stent frame, and circumscribes the tubular portion; and (2) a plurality of prosthetic valve leaflets, coupled to the frame assembly and disposed in the tubular portion, wherein the inner stent frame is cut from a first tube of nitinol that has a first-tube wall thickness, the outer stent frame is cut from a second tube of nitinol that has a second-tube wall thickness that is greater than the first-tube wall thickness.

Providing a frame assembly in which the outer frame has greater radial thicknesses is hypothesized by the inventors to advantageously provide (i) radially-expansive strength (and resistance to radially-inward deformation) to the portion of the frame assembly in which the prosthetic leaflets are disposed, and (ii) rigidity (and resistance to fatigue) to legs 450.

For some applications, when frames 430 and 460 are separate and independent (e.g., during manufacturing, before the frames are fixed to each other), and the frames are in respective relaxed expanded states (e.g., in the absence of external deforming forces, such as if placed on a table) tubular portion 432 defines an inner-stent-frame relaxed expanded diameter (which is measured as an outer diameter of the tubular portion) that is greater than an outer-stent-frame relaxed expanded diameter defined by ring 466 (which is measured as an inner diameter of the ring). For some applications, the inner-stent-frame relaxed expanded diameter is 0.5-1.5 (e.g., 0.5-1, such as 0.8) mm greater than the outer-stent-frame relaxed expanded diameter.

Therefore, in the expanded state of frame assembly 422 (shown in FIG. 10), frame 460 (e.g., ring 466) constrains tubular portion 432 to an inner-stent-frame constrained expanded diameter that is smaller than the inner-stent-frame relaxed expanded diameter. Therefore, even in the relaxed expanded state of frame assembly 422 (i.e., the state shown in FIG. 10), residual stress is typically present in frame 430 (e.g., tubular portion 432 thereof) and/or frame 460 (e.g., ring 466 thereof). Additionally, when the frame assembly is in its compressed state, and throughout its expansion into its expanded state, circumferential contact (and reciprocating expansive and compressive forces) is maintained between frame 460 and tubular portion 432.

It is hypothesized by the inventors that this optional residually-stressed configuration advantageously increases the strength of the frame assembly (e.g., the tubular portion), and in particular its resistance to deformation, e.g., in response to forces applied directly to the frame assembly by tissue of the native valve, and/or applied indirectly to the frame assembly during systole when ventricular blood is forced against the prosthetic leaflets, which pull on the frame assembly.

It is to be noted that frames 430 and 460 are fixed to each other independently of any additional coupling that might be provided by the residually-stressed configuration. For example, and as described hereinabove, the frames are fixed to each other at coupling points 452, e.g., by welding, soldering, crimping, stitching (e.g., suturing), gluing, or any other suitable technique. As described hereinbelow with reference to FIGS. 11A-C, for some applications the frames are also fixed to each other at commissures of the implant. That is, the residually-stressed configuration is provided for strength and rigidity of the frame assembly (and for ensuring maintenance of circumferential contact between the frames), rather than for coupling of the frames to each other.

Figure 11A:
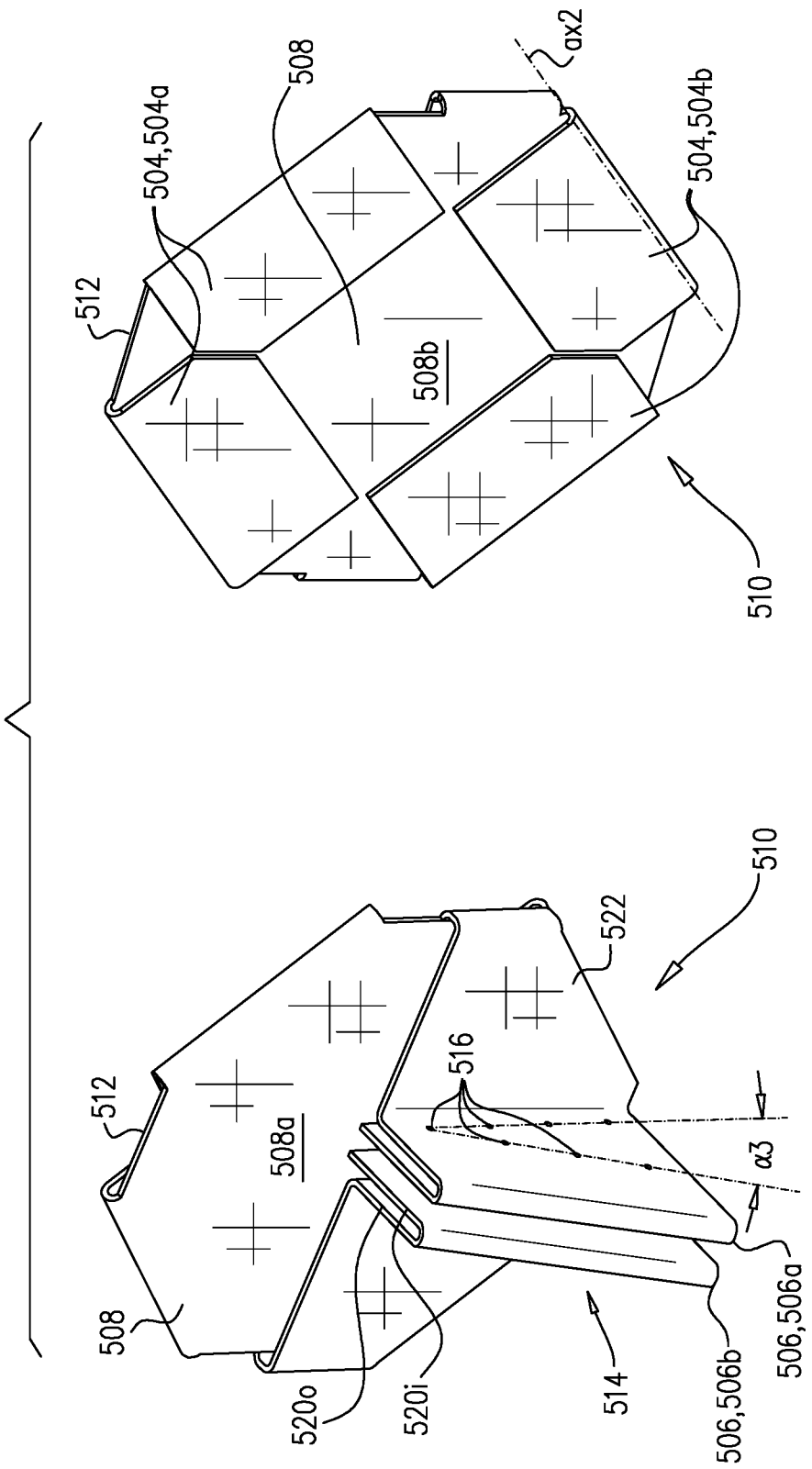
FIGS. 11A-C are schematic illustrations of a connector and a commissure of a prosthetic valve, in accordance with some applications of the invention.
Figure 11B:
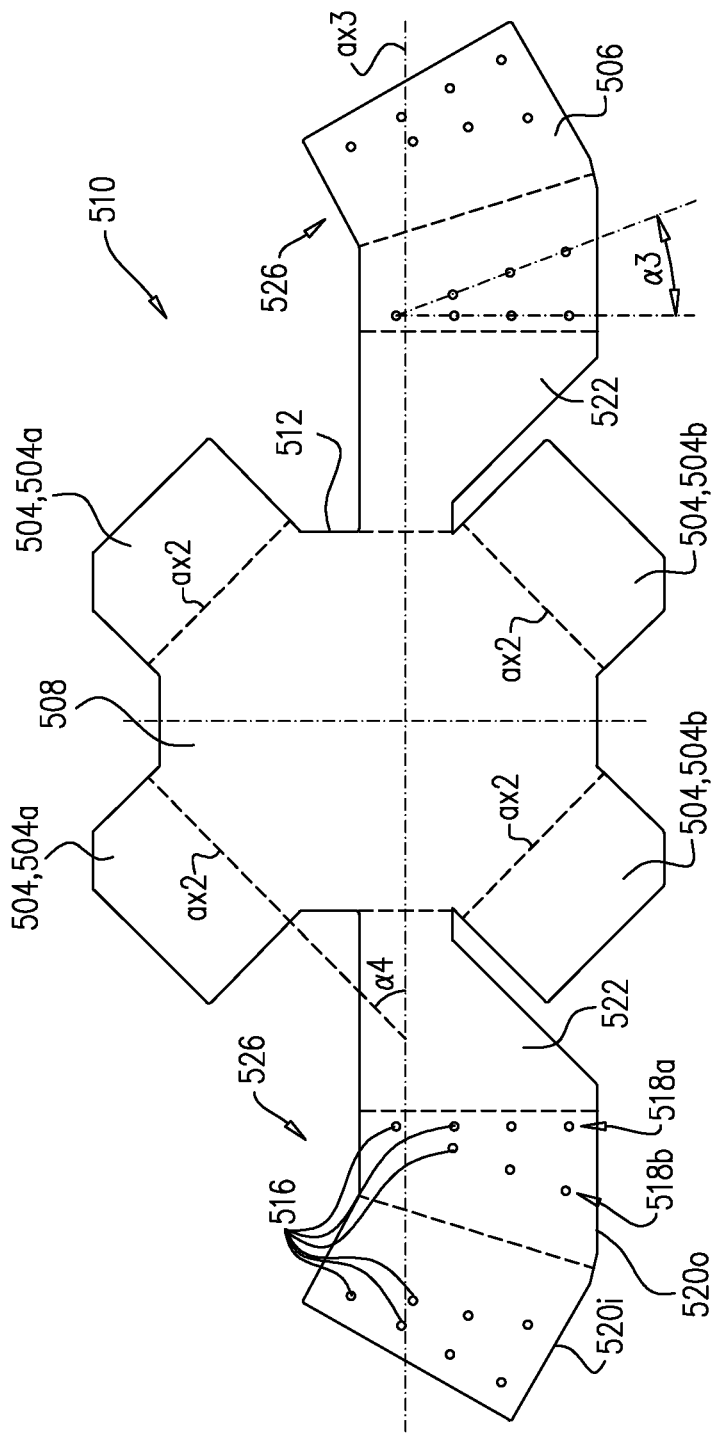
Figure 11C:
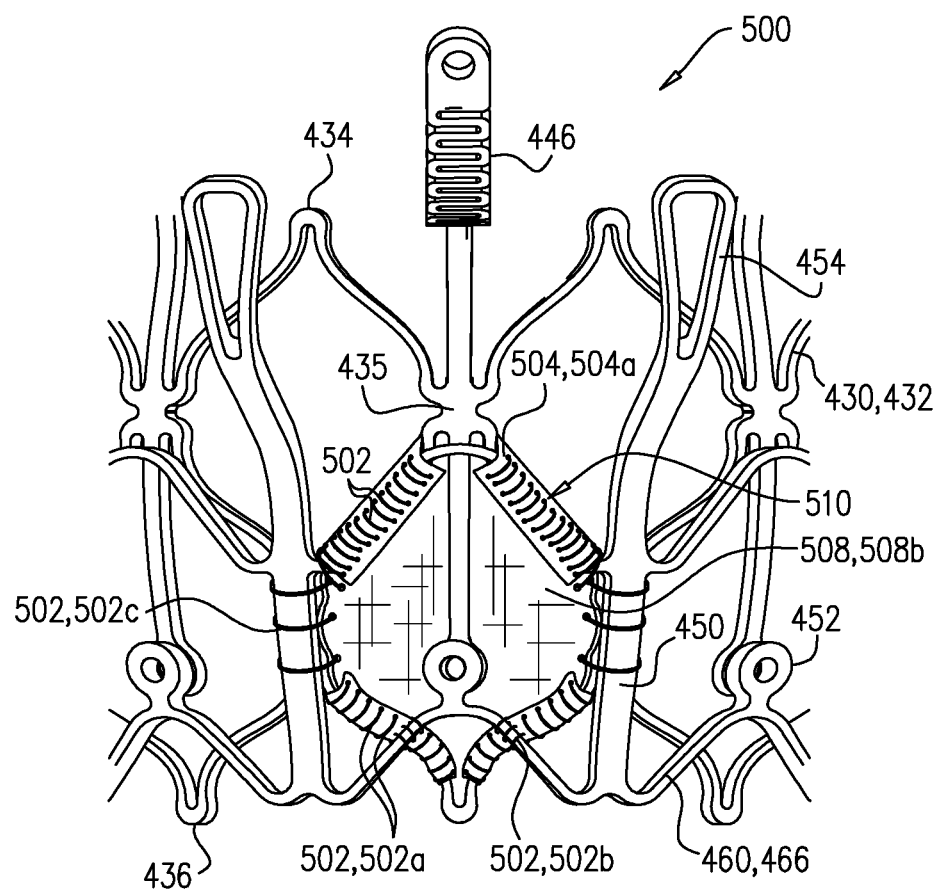

Reference is made to FIGS. 11A-C, which are schematic illustrations of a connector 510 and a commissure 500 of a prosthetic valve, in accordance with some applications of the invention. Connector 510 typically comprises a flexible sheet 512 that is folded to define elements of the connector. Further typically, sheet 512 is a single, unitary sheet (e.g., cut from a single piece of stock material, such as a fabric). FIG. 11A shows two perspective views of connector 510 (e.g., sheet 512 thereof) in its folded state, and FIG. 11B shows its unfolded state. FIG. 11C shows connector 510 fixed to frame assembly 422 at commissure 500. Commissure 500 is described with respect to the implant to which frame assembly 422 belongs, although it may be used in combination with the other prosthetic valves described herein, and/or with other prosthetic valves, mutatis mutandis.

The implant to which frame assembly 422 belongs defines a plurality of commissures 500 at which two of the prosthetic leaflets of the implant (e.g., leaflets 58 or similar) meet, and are fixed to the frame assembly. At each commissure, the implant comprises a plurality of stitches (e.g., sutures) 502, via which commissural portions of the two prosthetic leaflets are secured to the frame assembly. For some applications, the stitches secure the prosthetic leaflets to the inner stent frame (frame 430, e.g., tubular portion 432 thereof) and to the outer stent frame (frame 460). That is, the leaflets are not coupled to the outer stent frame merely by being fixed to the inner stent frame, which in turn is coupled to the outer stent frame. Rather, the leaflets are fixed to both frames by stitches 502. Because (as described hereinabove) (i) frame 460 is radially thicker than frame 430, and (ii) the relative diameters of the frames results in residual stress and maintained circumferential contact between frames 430 and 460, the fixation of the leaflets to both frames advantageously provides the implant with enhanced resistance to pulling of commissures 500 radially inward by the prosthetic leaflets when ventricular pressure increases during ventricular systole.

For some applications, and as shown, stitches 502 fix the leaflets to both frames by fixing a connector 510 (typically comprising primarily or solely a fabric) to the two frames. Connector 510 is shaped to define a plurality of flaps 504, and a leaflet-receptacle 514 comprising one or more (e.g., two) leaflet-engaging tabs 506, such as a first leaflet-engaging tab 506a and a second leaflet-engaging tab 506b. For some applications, connector 510 is shaped to define a panel (e.g., a plate) 508, tabs 506 protrude from one side of the panel, and each flap 504 folds over a respective portion of the other side of the panel. The commissural portions of the leaflets are stitched to leaflet-engaging tabs 506 (e.g., to respective leaflet-engaging tabs). Flaps 504 are stitched to frames 430 and 460—i.e., are fixed to the frames by stitches 502. Typically, flaps 504 are folded over or wrapped around elements of frames 430 and 460, and are fixed in this disposition by stitches 502, thereby providing increased strength to the fixation of the leaflets to the frames (and of the frames to each other).

Typically, connector 510 comprises four flaps 504. For some applications, and as shown, flaps 504 are arranged in a circuit such that each flap has two adjacent flaps around the circuit, and the fold axis ax2 of each flap is oriented at 60-120 degrees (e.g., 70-110 degrees, e.g., 80-100 degrees) from the fold axis of each of its adjacent flaps. For applications in which the frame to which connector 510 is to be connected has a cellular structure with roughly diamond-shape cells, such an arrangement facilitates attachment of the connector to the frame.

For some applications, and as shown, and as shown, connector 510 has four flaps arranged roughly in a diamond shape, with two upstream flaps 504a tapering away from each other in a downstream direction, and two downstream flaps 504b tapering toward each other in a downstream direction. Each upstream flap 504a is typically folded over or wrapped around an element of frame 430 and an element of frame 460. As can be seen in FIG. 11C, at commissure 500, elements of frame 430 align with elements of frame 460, and flaps 504a are arranged to align with these elements of both frames. Flaps 504 are folded over or wrapped around these elements of both frames, and are fixed to these elements by stitches 502. In the position of downstream flaps 504b, elements of frame 430 do not align with elements of frame 460, and may even be perpendicular to them. Downstream flaps 504b are arranged to align with elements of frame 430, and are folded over or wrapped around elements, but typically not over or around elements of frame 460. The elements of frame 430, and flaps 504b, are stitched to elements of frame 460; these stitches are indicated by the reference numeral 502b, while the stitches that secure flaps over or around frame elements are indicated by the reference numeral 502a. For some applications, panel 508 is also stitched to elements of frame 430 and/or frame 460; these stitches are indicated by the reference numeral 502c.

It is to be noted that frames 430 and 460 are thereby fixed to each other at commissures 500 (i.e., in addition to at coupling points 452).

Alternatively, connector 510 and/or the stitches may secure the leaflets only to inner frame 430, such that the leaflets are coupled to outer frame 460 only via inner frame 430.

There is therefore provided, in accordance with some applications of the invention, a connector (e.g., connector 510) comprising a flexible sheet (e.g., sheet 512) that is folded to define: (i) a panel (e.g., panel 508) that has a first side (e.g., side 508a), and a second side (e.g., side 508b) that is opposite the first side; (ii) a leaflet receptacle (e.g., receptacle 514), disposed on the first side of the panel, and protruding in the first direction away from the panel; and (iii) a plurality of flaps (e.g., flaps 504), each flap folded about a respective fold axis (e.g., axis ax2) such that at least part of each flap is disposed on the second side of the panel.

Receptacle 514 is configured to sandwich one or more prosthetic leaflets between leaflet-engaging tabs 506a and 506b. Typically, stitching holes 516 are defined in leaflet-engaging tabs 506 to guide the introduction of stitches which will secure the leaflets sandwiched between the tabs. For some applications, holes 516 are arranged into rows. For example, and as shown, each leaflet-engaging tab 506 may define a first row 518a of stitching holes and a second row 518b of stitching holes, the rows of one tab being aligned with the rows of the other tab. For some such applications, rows 518a and 518b diverge from each other at an angle alpha_3, typically such that that progressively downstream parts of the rows are progressively further from each other. For example, angle alpha_3 may be 10-45 degrees (e.g., 10-30 degrees, e.g., 15-25 degrees, such as about 20 degrees).

For some applications, sheet 512 is folded such that each leaflet-engaging tab 506 comprises an outer layer 520o, and an inner layer 520i that is positioned to be sandwiched between the outer layer and the one or more leaflets.

In the unfolded state of connector 510 (FIG. 11B), sheet 512 defines a plane (i.e., the plane of the page). In the unfolded state, sheet 512 defines, in the plane, (i) panel 508 at a medial region of sheet 512, (ii) flaps 504, disposed peripherally to the panel, and (iii) first and second tab portions 526, also disposed peripherally from the panel. Each tab portion 526 includes outer layer 520o and inner layer 520i, and in the folded state, defines a respective leaflet-engaging tab 506.

Typically, sheet 512 further defines bridging elements 522, via each of which a respective tab portion 526 is connected to panel 508. Flaps 504 are connected to panel 508 independently of the bridging elements.

In the unfolded state, tab portions 526 flank panel 508 by being disposed, in the plane, on opposing lateral sides of the panel. In the unfolded state, panel 508, tab portions 526, and bridging elements 522 are arranged in a row that defines a lateral axis ax3 in the plane, axis ax3 passing through the panel, tab portions, and bridging elements. Axis ax3 typically passes between upstream flaps 504a and downstream flaps 504b. Typically, the fold axis ax2 of each flap 504 is disposed at an angle alpha_4 that is 30-60 degrees from lateral axis ax3.

In the folded state, bridging elements 522 extend from respective edges of panel 508 and toward each other across first side 508a of the panel, and each of the leaflet-engaging tabs 506 protrudes from its respective bridging element away from the first side of the panel in the direction that the first side of the panel faces.

Reference is made to FIGS. 12A-B and 13A-G, which are schematic illustrations of another connector 610 for connecting prosthetic leaflets (e.g., leaflets 58) to a frame of a prosthetic valve implant, in accordance with some applications of the invention. Connector 610 may be used with any of the implants described herein, or with a different prosthetic valve, mutatis mutandis.

Figure 12A:
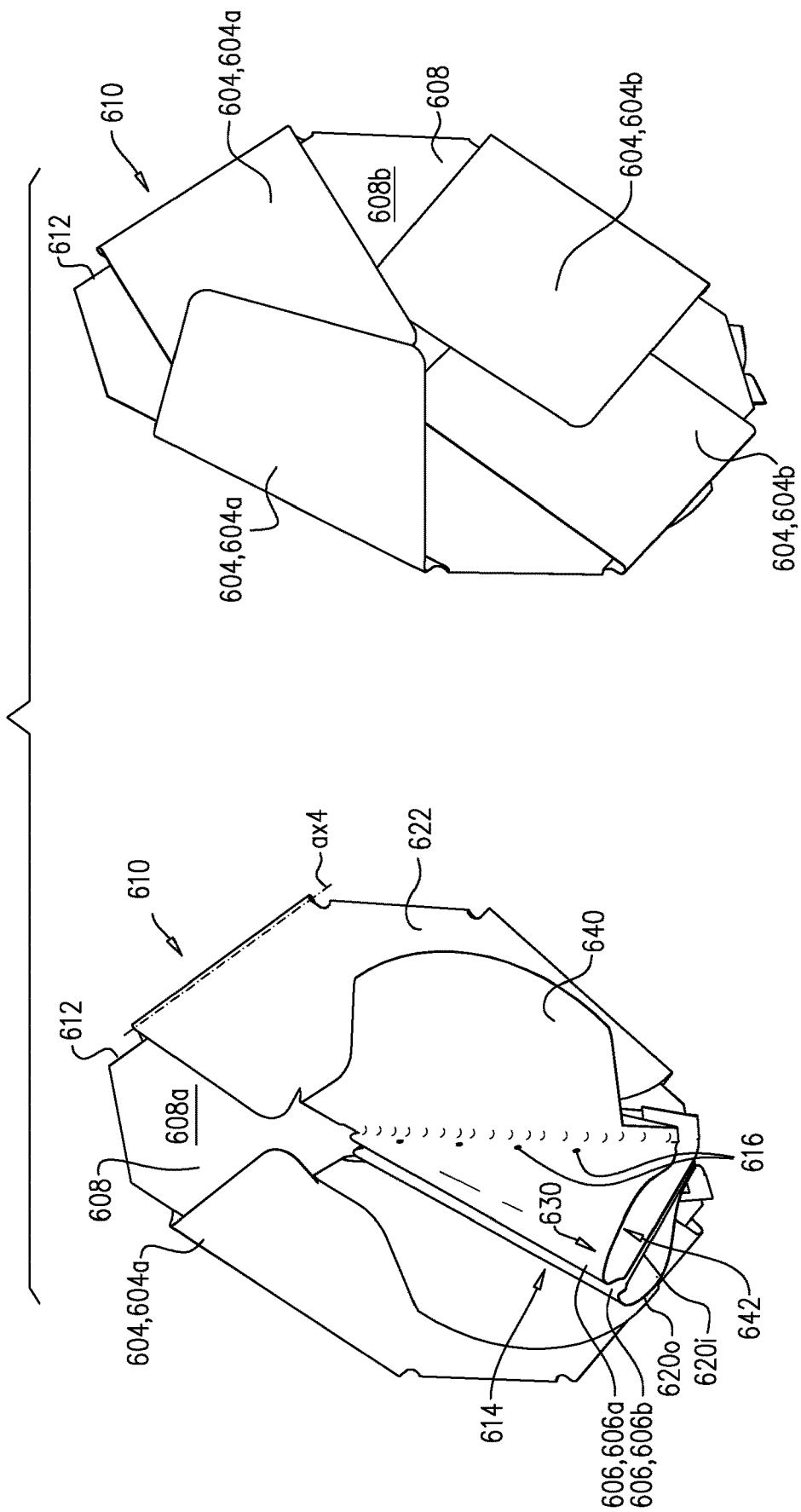
Figure 12B:
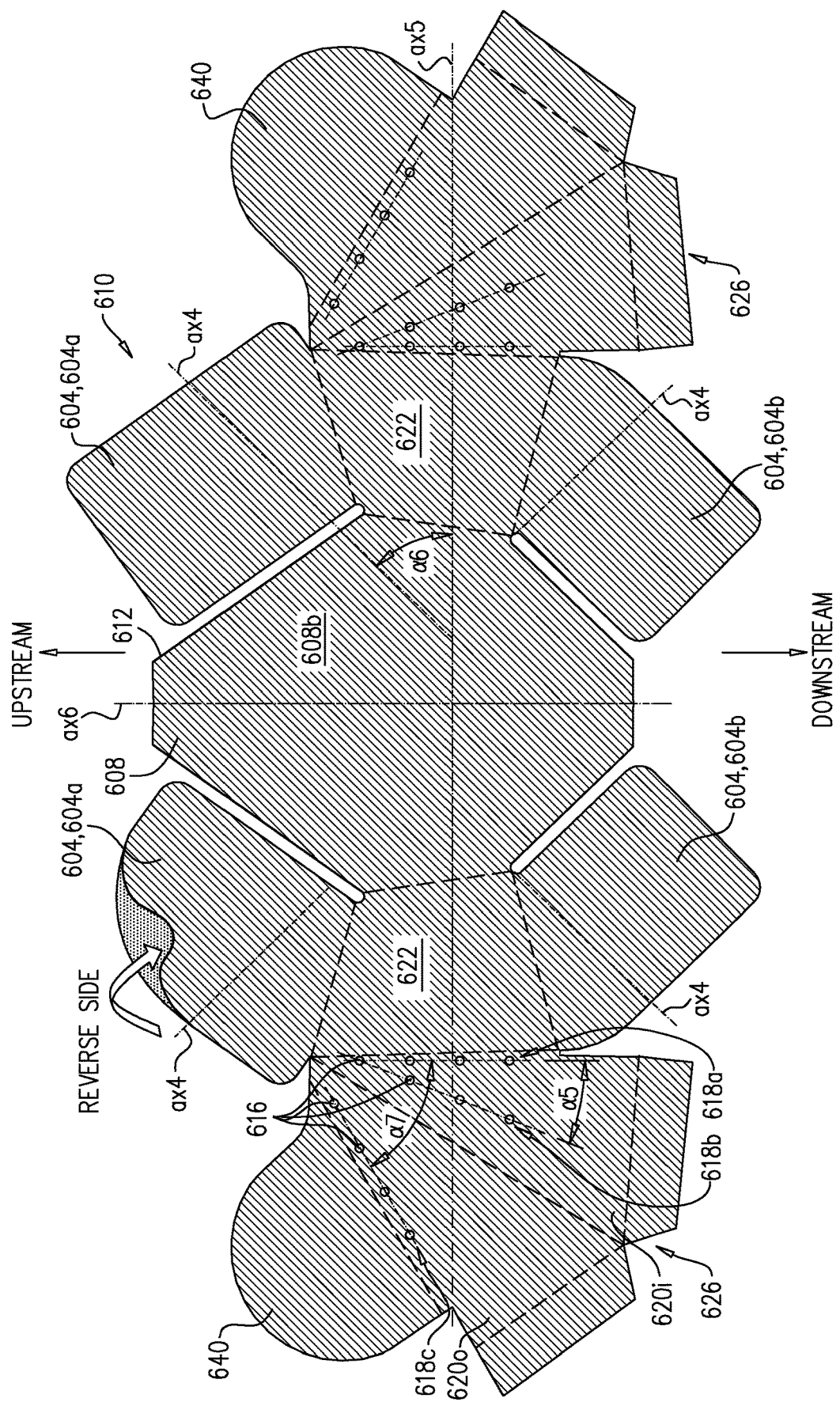

Connector 610 typically comprises a flexible sheet 612 that is folded to define elements of the connector. Further typically, sheet 612 is a single, unitary sheet (e.g., cut from a single piece of stock material, such as a fabric). FIG. 12A shows two perspective views of connector 610 (e.g., sheet 612 thereof) in its folded state, and FIG. 12B shows its unfolded state. To facilitate illustration of the folding of sheet 612, in FIGS. 12B and 13A-G opposing sides of the sheet are differently shaded, e.g., as demonstrated by a corner of sheet 612 being curled over in FIG. 12B to show its reverse side.

Connector 610 (e.g., in its folded state) is shaped to define a plurality of flaps 604, and a leaflet-receptacle 614 comprising one or more (e.g., two) leaflet-engaging tabs 606, such as a first leaflet-engaging tab 606a and a second leaflet-engaging tab 606b. Connector 610 is typically shaped to define a panel (e.g., a plate) 608. In the folded state, tabs 606 protrude from a first side 608a of the panel, and each flap 604 folds over a second side 608b of the panel (e.g., a respective portion thereof). The commissural portions of leaflets 58 are stitched to leaflet-engaging tabs 606. Flaps 604 are folded over or wrapped around elements of the frame of the prosthetic valve implant, e.g., as shown in FIG. 13G. Typically, flaps 604 are fixed in this disposition by stitches (not shown).

Typically, connector 610 comprises four flaps 604, typically two upstream flaps 604a and two downstream flaps 604b. For some applications, and as shown, flaps 604 are arranged in a circuit such that each flap has two adjacent flaps around the circuit, and the fold axis ax4 of each flap is oriented at 60-120 degrees (e.g., 70-110 degrees, e.g., 80-100 degrees) from the fold axis of each of its adjacent flaps. For applications in which the frame to which connector 610 is to be connected has a cellular structure with roughly diamond-shape cells, such an arrangement facilitates attachment of the connector to the frame, e.g., as shown in FIG. 13G.

There is therefore provided, in accordance with some applications of the invention, a connector (e.g., connector 610) comprising a flexible sheet (e.g., sheet 612) that is folded to define: (i) a panel (e.g., panel 608) that has a first side (e.g., side 608a), and a second side (e.g., side 608b) that is opposite the first side; (ii) a leaflet receptacle (e.g., receptacle 614), disposed on the first side of the panel, and protruding in a first direction away from the panel; and (iii) a plurality of flaps (e.g., flaps 604), each flap folded about a respective fold axis (e.g., axis ax4) such that at least part of each flap is disposed on the second side of the panel.

Receptacle 614 is configured to sandwich one or more prosthetic leaflets between leaflet-engaging tabs 606a and 606b. Typically, stitching holes 616 are defined in leaflet-engaging tabs 606 to guide the introduction of stitches which will secure the leaflets sandwiched between the tabs. For some applications, holes 616 are arranged into rows. For example, and as shown, each leaflet-engaging tab 606 may define a first row 618a of stitching holes and a second row 618b of stitching holes, the rows of one tab being aligned with the corresponding rows of the other tab. For some such applications, rows 618a and 618b diverge from each other at an angle alpha_5, typically such that that progressively downstream parts of the rows are progressively further from each other. For example, angle alpha_5 may be 10-45 degrees (e.g., 10-30 degrees, e.g., 15-25 degrees, such as about 20 degrees). Downstream is defined by the direction in which the prosthetic leaflets facilitate one-way fluid flow, which itself is in part dependent on the orientation of the attachment of the leaflets to connectors 610.

Typically, sheet 612 is folded such that each leaflet-engaging tab 606 comprises an outer layer 620o, and an inner layer 620i that is positioned to be sandwiched between the outer layer and the one or more leaflets. For some applications, and as further described hereinbelow, rows 618a and 618b are defined by inner layer 620i, and a third row 618c of stitching holes is defined by outer layer 620, and the folding of sheet 612 is such that row 618c aligns with row 618a. For such applications, only row 618c is visible in the folded state. In the unfolded state, an angle alpha_7 between rows 618a and 618c (i.e., at which rows 618a and 618c diverge from each other) is typically 40-120 degrees (e.g., 40-90 degrees, e.g., 40-70 degrees, e.g., 40-60 degrees, such as 50-60 degrees).

In the unfolded state of connector 610 (FIG. 12B), sheet 612 defines a plane (i.e., the plane of the page). In the unfolded state, sheet 612 defines, in the plane, (i) panel 608 (i.e., a panel portion of the sheet) at a medial region of sheet 612, (ii) flaps 604, disposed peripherally to the panel, and (iii) first and second tab portions 626, also disposed peripherally from the panel. Each tab portion 626 includes outer layer 620*o* and inner layer 620*i*, and in the folded state, defines a respective leaflet-engaging tab 606.

Sheet 612 further defines bridging elements 622, via each of which a respective tab portion 626 is connected to panel 608. Flaps 604 are also connected to panel 608 via the bridging elements.

Typically, in the folded state, part of each flap 604 is disposed on first side 608*a* of panel 608, and part of each flap is disposed on second side 608*b*. For example, bridging elements 622 are typically disposed on first side 608*a*, and each flap 604 extends from one of the bridging elements and around panel 608 such that part of the flap is disposed on side 608*a*, and part is disposed on side 608*b*.

In the unfolded state, tab portions 626 flank panel 608 (i.e., the panel portion of the sheet) by being disposed, in the plane, on opposing lateral sides of the panel. In the unfolded state, panel 608, tab portions 626, and bridging elements 622 are arranged in a row that defines a lateral axis ax5 in the plane, axis ax5 passing through the panel, tab portions, and bridging elements. Axis ax5 typically passes between upstream flaps 604*a* and downstream flaps 604*b*. Typically, the fold axis ax4 of each flap 604 is disposed at an angle alpha_6 that is 30-70 degrees from lateral axis ax5.

Sheet 612 typically further defines a lapel 640 that, in the unfolded state, is lateral to each tab portion 626. Lapels 640 are described further hereinbelow.

In the folded state, bridging elements 622 extend from respective edges of panel 608 and toward each other across first side 608*a* of the panel, and each of the leaflet-engaging tabs 606 protrudes from its respective bridging element away from the first side of the panel in the direction that the first side of the panel faces.

Figure 13A:
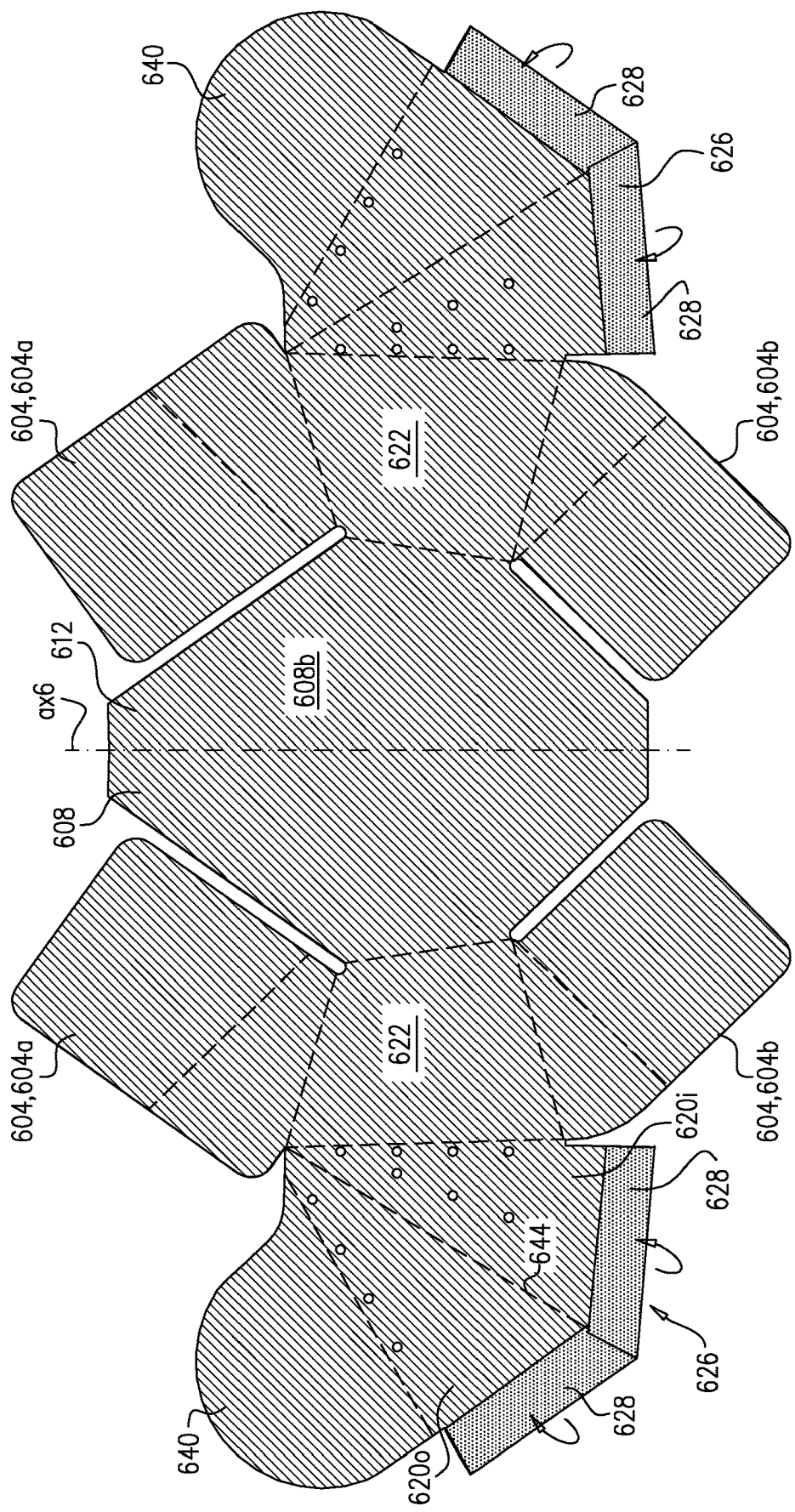
Figure 13B:
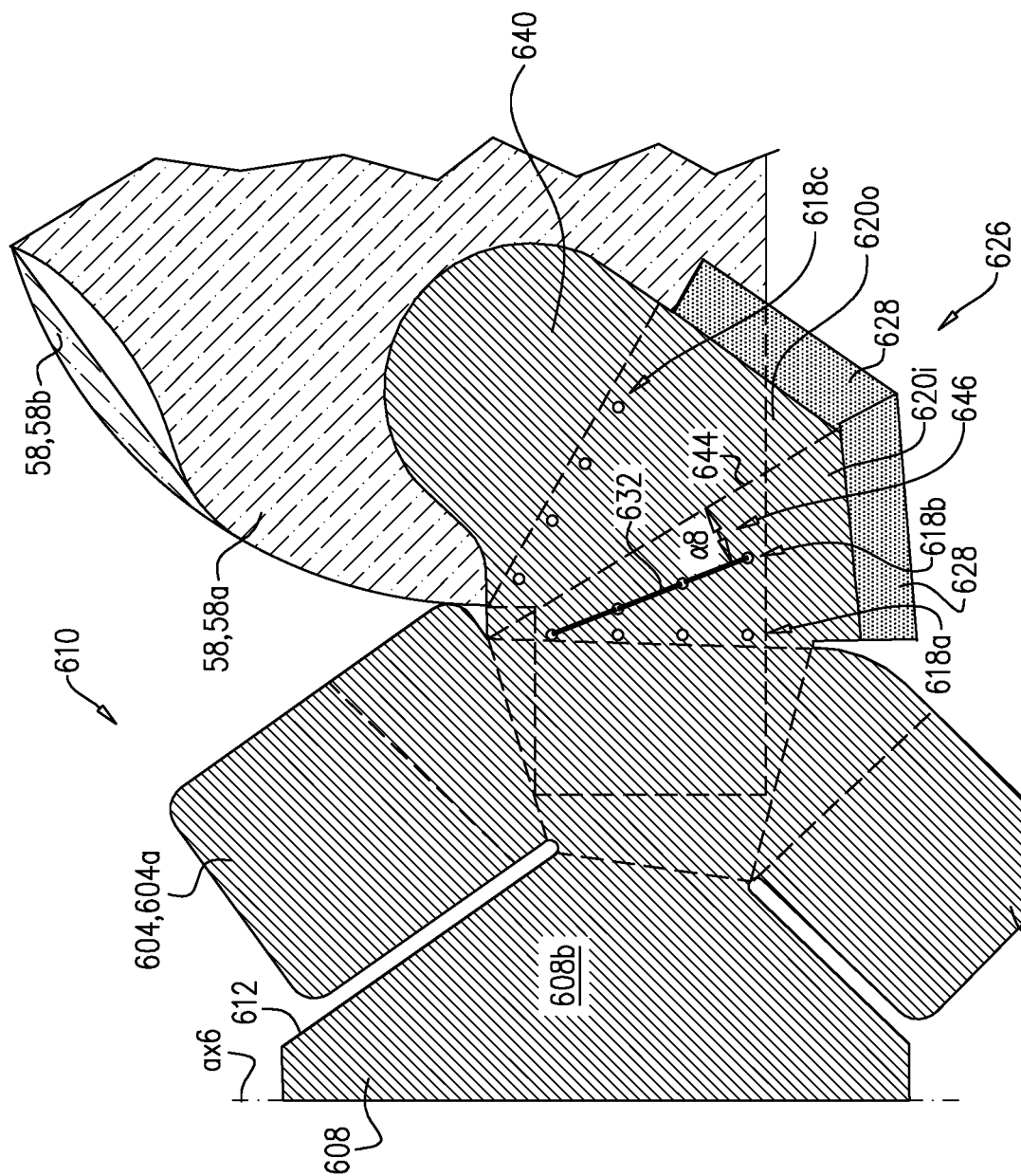
Figure 13E:
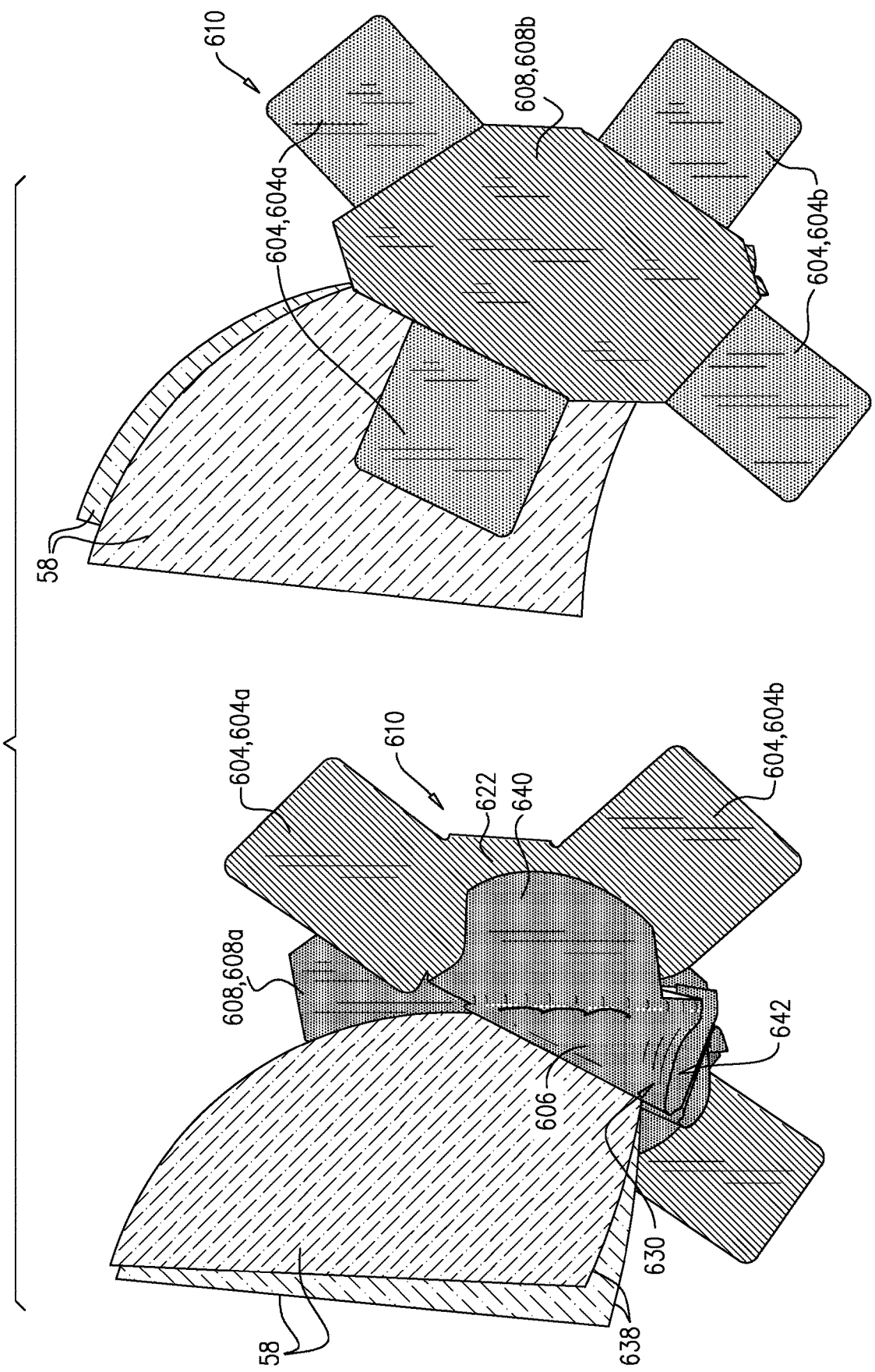
Figure 13F:
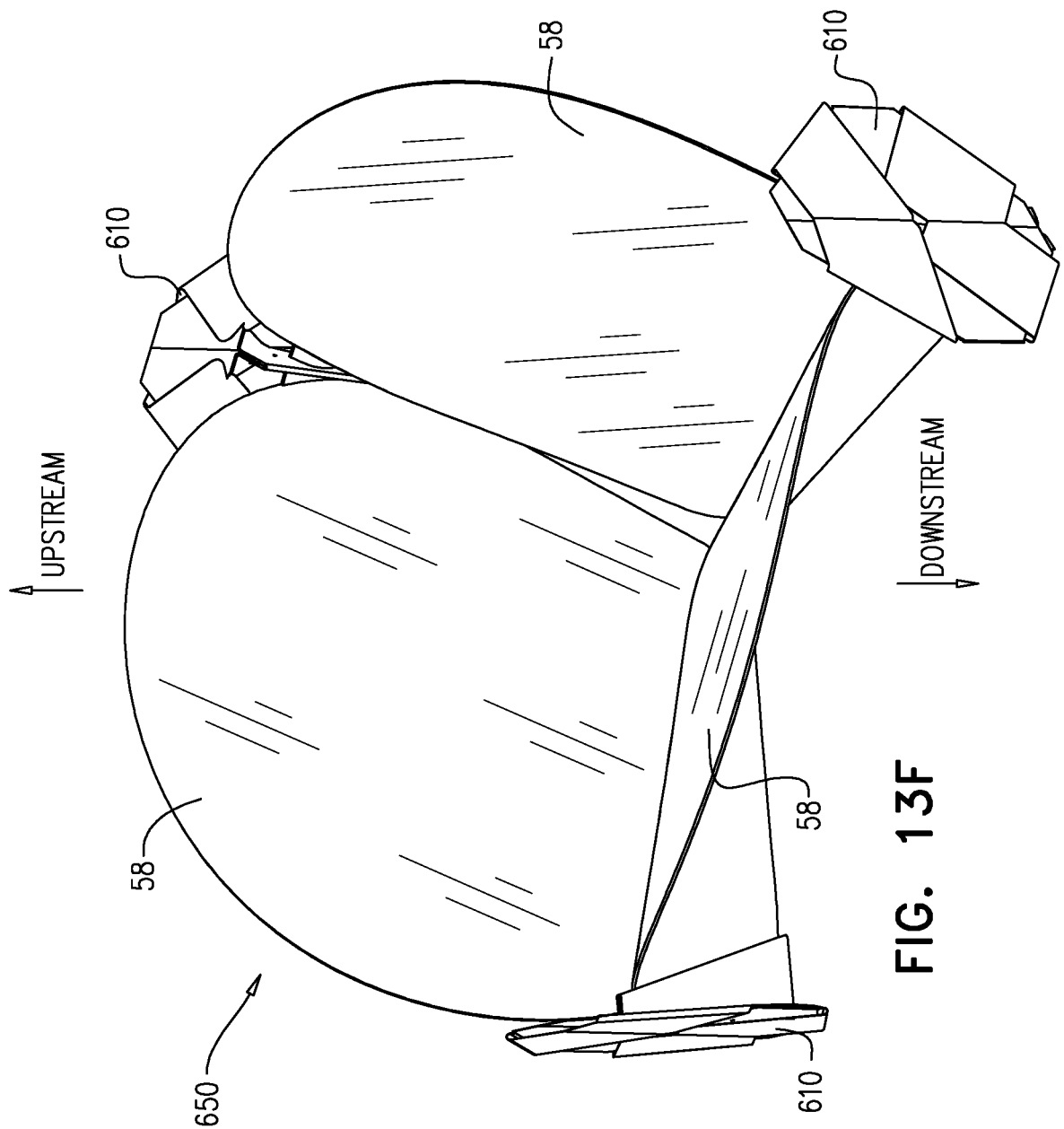
Figure 13G:
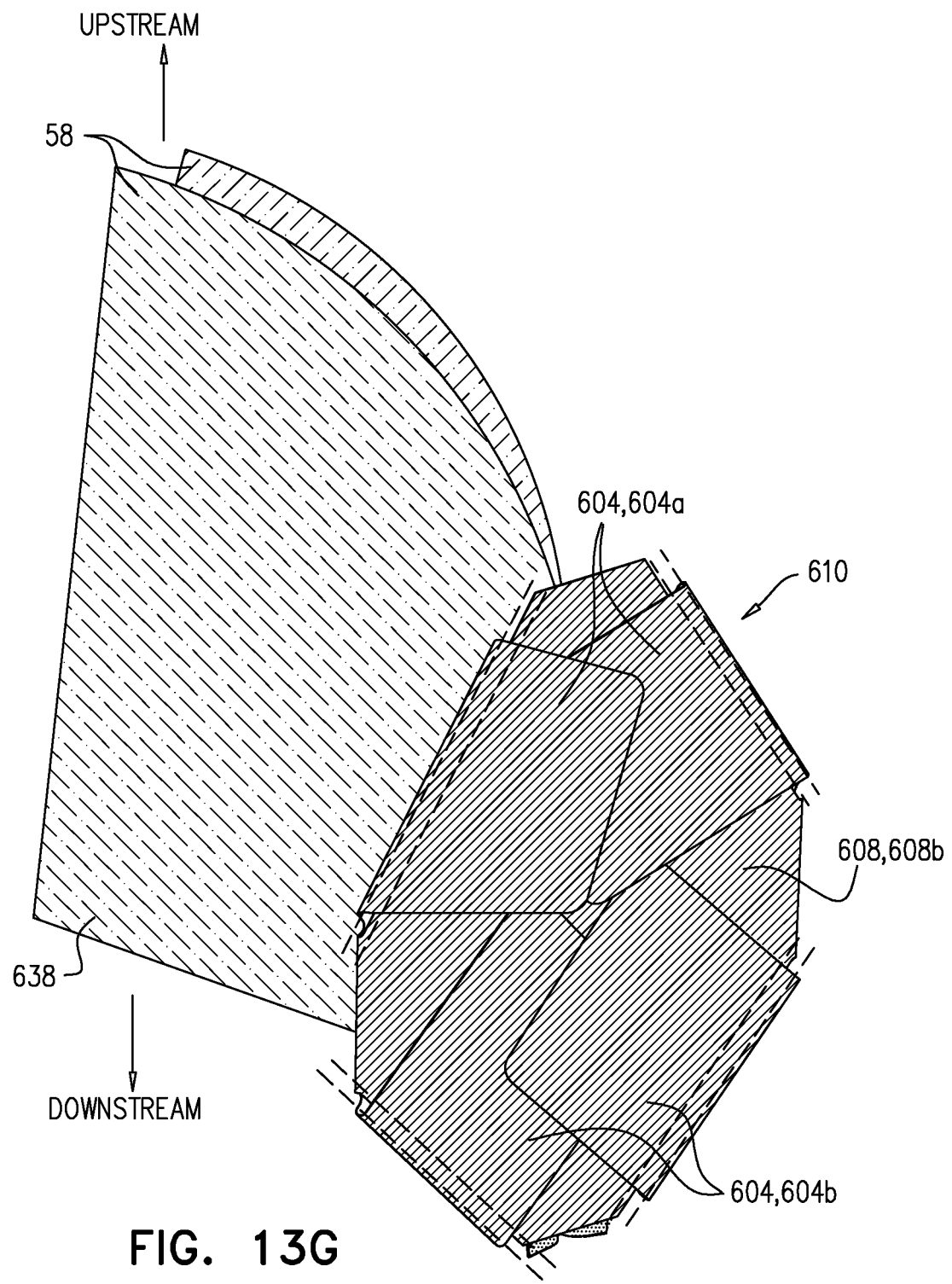

FIGS. 13A-G show steps in the folding of sheet 612 from the unfolded state to the folded state, in order to define connector 610, in accordance with some applications of the inventions. Folds are made in downstream regions of tab portions 626, e.g., the downstream edge of each layer 610*o* and/or each layer 610*i* is folded over to form respective folds 628 (FIG. 13A). This will provide each leaflet-engaging tab with a cushion 630, described hereinbelow. Folds 628 may be secured by stitching.

Sheet 612 is folded in half along its longitudinal axis ax6 (or is simply bent around the longitudinal axis without creating a distinct fold), bringing tab portions 626 together (FIG. 13B). Commissural portions of two leaflets 58 (e.g., a first leaflet 58*a* and a second leaflet 58*b*) are introduced, such that they are sandwiched together between portions 626. As shown, the positioning of the leaflets is typically such that they are disposed between the holes 616 of one portion 626, and those of the other portion 626. Holes 616 of row 618*b* of both portions 626 are stitched together by a first stitching 632. Stitching 632 therefore passes through leaflets 58*a* and 58*b*, thereby securing them to connector 610.

Subsequently, tab portions 626 are folded, along a fold line 644, back against themselves, thereby defining inner layer 620*i* and outer layer 620*o* (FIG. 13C), and aligning rows 618*c* with rows 618*a* (e.g., such that the resulting angle between fold line 644 and row 618*a* is substantially equal to (e.g., within 5% of) the resulting angle between the fold line and row 168*c*).

It is to be noted that first stitching 632, and holes 616 of rows 618*a* and 618*b*, are covered (e.g., hidden) by outer layer 620*o*. Rows 618*c* and 618*a* of one tab portion 626, leaflets 58*a* and 58*b*, and rows 618*a* and 618*c* of the other tab portion are then stitched together by a second stitching 634. This reinforces the connection of the leaflets to connector 610. Thus, tab portions 626 are formed into leaflet-engaging tabs 606.

There is therefore provided, in accordance with some applications of the invention, a method for use with a flexible sheet (e.g., sheet 612) that, in an unfolded state of the sheet, defines a panel (e.g., panel 608) at a medial region of the sheet, a first tab portion disposed peripherally to the panel, and a second tab portion disposed peripherally to the panel opposite the first tab portion, the method comprising:
  sandwiching, between the first tab portion and the second tab portion, (i) a first commissural portion of a first prosthetic leaflet, and (ii) a second commissural portion of a second prosthetic leaflet;
  attaching the first tab portion and the second tab portion to the flexible sheet by stitching a first stitching (e.g., stitching 632) through the first tab-portion, the first commissural portion, the second commissural portion, and the second tab-portion;
  subsequently, covering the first stitching by:
    folding the first tab portion back against itself to form the first tab portion into a first tab having first-tab outer layer and a first-tab inner layer, such that the first-tab inner layer is sandwiched between the first-tab outer layer and the first commissural portion, and
    folding the second tab portion back against itself to form the second tab portion into a second tab having a second-tab outer layer and a second-tab inner layer, such that the second-tab inner layer is sandwiched between the second-tab outer layer and the second commissural portion; and
  subsequently, stitching a second stitching (e.g., stitching 634) through the first-tab outer layer, the first-tab inner layer, the first commissural portion, the second commissural portion, the second-tab inner layer, and the second-tab outer layer.

Typically, and as shown, fold line 644 is closer to first stitching 632 than to second stitching 634. Typically, and as shown, an angle alpha_8 between fold line 644 and first stitching 632 (FIG. 13B) is smaller than an angle alpha_9 between the fold line and second stitching 634 (FIG. 13C). Angle alpha_8 is also the angle between fold line 644 and row 618*b*. Angle alpha_9 is also the angle between fold line 644 and row 618*c* (and also typically between the fold line and row 618*a*). Therefore, typically, the folding of tab portion 626 back against itself comprises folding the tab portion such that an angle between the fold line and row 618*b* is smaller than both (i) the angle between the fold line and row 618*a*, and (ii) the angle between the fold line and row 618*c*.

There is therefore provided, in accordance with some applications of the invention, apparatus, comprising:
  a unitary flexible sheet (e.g., sheet 612), folded to define:
    a panel (e.g., panel 608), having a first side facing in a first direction, and a second side that is opposite the first side;
    a first tab (e.g., leaflet-engaging tab 606*a*), disposed on the first side of the panel, having a first-tab outer layer and a first-tab inner layer, and protruding in the first direction away from the panel; and
    a second tab (e.g., leaflet-engaging tab 606*a*), disposed on the first side of the panel, having a second-tab outer layer and a second-tab inner layer, and protruding in the first direction away from the panel;
  a first prosthetic leaflet having a first-leaflet commissural portion disposed between the first-tab inner layer and the second-tab inner layer;

a second prosthetic leaflet having a second-leaflet commissural portion disposed between the first-tab inner layer and the second-tab inner layer;

a first stitching (e.g., stitching 632), stitched through the first-tab inner layer, the first-leaflet commissural portion, the second-leaflet commissural portion, and the second-tab inner layer; and a second stitching (e.g., stitching 634), stitched through the first-tab outer layer, the first-tab inner layer, the first-leaflet commissural portion, the second-leaflet commissural portion, the second-tab inner layer, and the second-tab outer layer, wherein the first-tab outer layer and the second-tab outer layer cover the first stitching.

It is to be noted that, in the unfolded state of sheet 612, the region of the sheet that eventually defines outer layer 620o is disposed further laterally than the region of the sheet that eventually defines inner layer 620i. This is in contrast to connector 510, in which the region of the sheet that eventually defines inner layer 520i is disposed further laterally than the region of the sheet that eventually defines outer layer 520o.

Subsequent to the step shown in FIG. 13C, the folding in half of sheet 612 shown in step 13B is reversed, mutatis mutandis, flattening panel 608 thereby bringing it closer to the leaflets, and moving bridging elements 622 away from each other and folding them against the panel (FIG. 13D). Typically, regions of each leaflet 58 (e.g., unstitched parts of the commissural portion of each leaflet) that are disposed beyond row 618c become disposed (e.g., sandwiched) between bridging elements 622 and another region of sheet 612, such as panel 608. Typically, the unstitched part of the commissural portion of one leaflet is moved away from the unstitched part of the commissural portion of the other leaflet.

Typically, the step shown in FIG. 13C brings lapels 640 into contact with bridging elements 622. The step shown in FIG. 13D typically causes each bridging element 622 to move with the bridging element 622 with which it is in contact, and folding with respect to outer layer 620i of leaflet-engaging tabs 606. For some applications, stitches are passed through lapel 640, bridging element 622, leaflet 58, and panel 608. This stitching may be an independent step, or may be achieved when securing flaps 604 to the frame of the prosthetic valve, e.g., as described hereinbelow.

FIG. 13E shows perspective views of the state shown in FIG. 13D. Each leaflet 58 has a downstream edge 638. It is to be noted that leaflet-engaging tabs 606 typically extend in a downstream direction beyond downstream edges 638. It is to be further noted that cushions 630 are typically positioned such that at least part of each cushion is disposed further downstream than downstream edges 638. Tabs 606 and/or cushions 630 are thereby configured to inhibit movement of the commissural portion of each leaflet 58 (and especially of downstream edges 638) toward the frame of the prosthetic valve. It is hypothesized by the inventors that this reduces a likelihood of leaflets 58 becoming damaged over time due to contact with the frame.

There is therefore provided, in accordance with some applications of the invention, apparatus, comprising:

(1) a unitary flexible sheet, folded to define (i) a panel, defining a plane, and having a first side facing in a first direction away from the plane, and a second side that is opposite the first side; (ii) a first tab, disposed on the first side of the panel, and protruding in the first direction away from the panel; and (iii) a second tab, disposed on the first side of the panel, and protruding in the first direction away from the panel;

(2) a first prosthetic leaflet having a first-leaflet commissural portion disposed between the first tab and the second tab;

(3) a second prosthetic leaflet having a second-leaflet commissural portion disposed between the first tab and the second tab;

wherein: (i) at the first tab, the sheet is folded to define a first cushion at a downstream edge of the first tab, the first cushion being configured and positioned to inhibit deflection of a downstream portion of the first prosthetic leaflet away from the second prosthetic leaflet and toward the plane, and (ii) at the second tab, the sheet is folded to define a second cushion at a downstream edge of the second tab, the second cushion being configured and positioned to inhibit deflection of a downstream portion of the second prosthetic leaflet away from the first prosthetic leaflet and toward the plane.

As described hereinabove, each cushion 630 is typically formed by folding at least one fold 628. Therefore, for some applications, sheet 612 defines a first-tab fold (in the first tab) and a second-tab fold (in the second tab), the first cushion comprises the first-tab fold, folded between the first-tab inner layer and the first-tab outer layer, and the second cushion comprises the second-tab fold, folded between the second-tab inner layer and the second-tab outer layer.

For some applications, each cushion is formed by folding a fold in each of the layers of each leaflet-engaging tab. That is, for some applications:

the first-tab fold described in the previous paragraph is a first-tab outer fold, continuous with the first-tab outer layer, the second-tab fold described in the previous paragraph is a second-tab outer fold, continuous with the second-tab outer layer, the sheet further defines:
a first-tab inner fold, continuous with the first-tab inner layer, and
a second-tab inner fold, continuous with the second-tab inner layer, the first cushion comprises:
the first-tab outer fold, folded between the first-tab outer layer and the first-tab inner fold, and
the first-tab inner fold, folded between the first-tab inner layer and the first-tab outer fold, and
the second cushion comprises:
the second-tab outer fold, folded between the second-tab outer layer and the second-tab inner fold, and
the second-tab inner fold, folded between the second-tab inner layer and the second-tab outer fold.

For some applications, each leaflet-engaging tab 606 defines a downstream opening 642 between inner layer 620i and outer layer 620o.

Typically, three connectors 610 are used to connect three leaflets 58 at three commissures, to form a valvular assembly 650 that comprises tri-leaflet check-valve (FIG. 13F). In the valvular assembly, connectors 610 are arranged circumferentially, and leaflets 58 extend radially inward from the connectors. Each connector 610 is secured to the frame of the prosthetic valve (FIG. 13G). For example, valvular assembly 650 may be disposed within lumen 38, and connectors 610 may be secured to frame 30 at tubular portion 32, and/or to frame 60 (e.g., at ring 66). Flaps 604 are folded over components of the frame of the prosthetic valve (which are shown in phantom), and secured by stitching. For some applications, some of this stitching may pass through several elements, such as flaps 604, panel 608, leaflets 58, bridging elements 622, and/or lapels 640. Typically, but not necessarily, valvular assembly 650 is assembled before connectors 610 are secured to the frame of the prosthetic valve.

Valvular assembly 650 is configured such that, when secured to the frame of the prosthetic valve, the valvular assembly facilitates upstream-to-downstream fluid flow through the lumen of the prosthetic valve by the three prosthetic leaflets opening (i.e., the downstream edges of the leaflets move away from each other), and to inhibit downstream-to-upstream fluid flow through the lumen by the three prosthetic leaflets closing (i.e., the downstream edges of the leaflets move toward each other). Typically, for each connector 610, when leaflets 58 open, tabs 606 (or at least a part of each) move away from each other, and when the leaflets close, the tabs (or at least a part of each) move toward each other.

Although FIGS. 13A-G show a particular sequence, and although some of the steps are necessarily performed before others, it is to be understood that some of the steps may be performed in a different order to that shown. For example, folds 628 may be folded at a later stage to that shown.

Reference is again made to FIGS. 12A-13G. It is to be noted that each tab 606 defines a loose region 646, further away from panel 608 than both stitching 634 and stitching 632. Loose region 646 is relatively loose with respect to leaflets 58. When the valvular assembly is coupled to a tubular frame as described hereinabove, loose region 646 is disposed radially inward from first stitching 632 and second stitching 634.

Reference is now made to FIGS. 14A-B, which are schematic illustrations of another connector 710 for connecting prosthetic leaflets (e.g., leaflets 58) to a frame of a prosthetic valve implant, in accordance with some applications of the invention. Connector 710 may be used with any of the implants described herein, or with a different prosthetic valve, mutatis mutandis. Typically, connector 710 is identical to connector 610, except that it further comprises a separate flexible sheet 712, used in combination with sheet 612. Typically, sheet 712 is placed between the commissural portions of the leaflets 58 being connected, such that when the commissural portions of the leaflets are sandwiched between tab portions 626, sheet 712 is sandwiched between the commissural portions of the leaflets. FIG. 14A is analogous to FIG. 13B, but showing the addition of separate flexible sheet 712. FIG. 14B is analogous to the left-side image of FIG. 13E, but showing the addition of separate flexible sheet 712.

The positioning of sheet 712 is typically such that it is disposed between holes 616 of row 618b of one tab portion 626, and the holes of row 618a of the other tab portion. The positioning of sheet 712 is also typically such that it is disposed between holes 616 of row 618a of one tab portion 626, and the holes of row 618a of the other tab portion. Therefore, for applications in which sheet 712 is used, first stitching 632 is typically stitched through sheet 712, and second stitching 634 is also typically stitched through sheet 712. For some applications, and as shown, sheet 712 protrudes in a downstream direction beyond tabs 606 (e.g., beyond cushions 630).

The use of sheet 712 results in the commissural portion of each leaflet being sandwiched between two layers of fabric, rather than between a layer of fabric and the other leaflet. It is hypothesized by the inventors that this strengthens the connection between the leaflets and the connector, and reduces a likelihood of tearing of the leaflets where they are stitched to the connector.

Reference is again made to FIGS. 1A-14B. For some applications, a biocompatible adhesive (e.g., comprising a polymer adhesive and/or a collagen adhesive) may be used to reinforce stitching of the implant. For some such applications, the adhesive is applied at (e.g., onto) stitching that secures the leaflets to fabric, such as stitching between the leaflets and the covering that lines the tubular portion of the implant (e.g., the adhesive being applied along the arched stitch line that follows the arch of each leaflet), and/or stitching between the leaflets and the commissural connectors (e.g., the adhesive being applied along one or more rows of holes of the connector's tab portions, and/or to the stitching that passes through the holes). For some such applications, the adhesive is applied at (e.g., onto) stitching that secures fabric to fabric, such as stitching between different parts of covering 23, and/or stitching that secures the flaps of a connector. It is hypothesized by the inventors that such use of an adhesive reduces a likelihood of the stitching cutting through the prosthetic leaflet or the fabric.

Reference is again made to FIGS. 1A-14B. Among the advantages provided by assembling a prosthetic valve from two (e.g., concentric) frames is the ability to divide the frame elements required between the two frames, in a manner that would not be possible in a single frame, or in a manner that, if a single frame were used, would increase the size (e.g., the diameter or the length) of the implant in its compressed state. Additionally, for some applications, the use of two frames allows different sizes of the implant to be compressed ("crimped") to the same or similar diameter, and for some such applications, to be delivered using the same delivery tool (e.g., delivery tool 89). For example, for implants comprising frame assembly 422, an implant of a larger size may have a lumen diameter that is at least 15 percent greater than the lumen diameter of an implant of a smaller size (in their respective expanded states), but in their compressed states, the diameter of the implant of the larger size may be no more than 2 percent greater than the diameter of the implant of the smaller size.

For some applications, a delivery tool is provided for use with different sizes of the implant, e.g., with the implants provided separately. For some such applications, a kit is provided containing a delivery tool and implants of different sizes.

Reference is again made to FIGS. 1A-14B. It is to be noted that unless specifically stated otherwise, the term "radially outward" (e.g., used to describe upstream support portion 40 and flanges 54) means portions of the element are disposed progressively further outward from a central point (such as longitudinal axis ax1 or tubular portion 32), but does not necessarily mean disposed at 90 degrees with respect to longitudinal axis ax1. For example, flanges 54 may extend radially outward at 90 degrees with respect to longitudinal axis ax1, but may alternatively extend radially outward at a shallower angle with respect to the longitudinal axis.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. An apparatus, comprising:
   a tubular frame that defines a lumen and has an inner surface that faces the lumen; and a unitary flexible sheet that, in an unfolded state of the sheet, defines:
  a panel portion at a medial region of the sheet,
  a first tab portion disposed peripherally to the panel, and having (i) a first part, and (ii) a second part that is disposed peripherally to the first part of the first tab portion, and
  a second tab portion disposed peripherally to the panel opposite the first tab portion, and having (i) a first part, and (ii) a second part that is disposed peripherally to the first part of the second tab portion,
the sheet being folded into a folded state in which the sheet defines:
  a panel, defined by the panel portion, having a first side facing in a first direction, and a second side that is opposite the first side;
  a first tab, defined by the first tab portion, the first tab being disposed on the first side of the panel, shaped such that progressively downstream parts of the first tab protrude progressively further away from the panel portion and into the lumen, and having:
    a first-tab inner layer defined by the first part of the first tab portion extending away from the panel in the first direction, and
    a first-tab outer layer defined by the second part of the first tab portion being folded back over the first part of the first tab portion, and extending back toward the panel;
  a second tab, defined by the second tab portion, the second tab being disposed on the first side of the panel, shaped such that progressively downstream parts of the second tab protrude progressively further away from the panel portion and into the lumen, and having:
    a second-tab inner layer defined by the first part of the second tab portion extending away from the panel in the first direction, and
    a second-tab outer layer defined by the second part of the second tab portion being folded back over the first part of the second tab portion, and extending back toward the panel;
  a first prosthetic leaflet having a first-leaflet commissural portion sandwiched between the first-tab inner layer and the second-tab inner layer; and
  a second prosthetic leaflet having a second-leaflet commissural portion sandwiched between the first-tab inner layer and the second-tab inner layer.

2. The apparatus according to claim 1, wherein the first tab defines a downstream opening between the first-tab inner layer and the first-tab outer layer, and the second tab portion defines a downstream opening between the second-tab inner layer and the second-tab outer layer.

3. The apparatus according to claim 1, wherein the sheet, in the folded state, further defines a plurality of flaps, each of the flaps extending from the panel, and configured to secure the second side of the panel against the inner surface by being folded around a respective component of the tubular frame.

4. The apparatus according to claim 3, wherein each flap of the plurality of flaps is stitched to the respective component of the tubular frame.

5. The apparatus according to claim 1, wherein the sheet, in the folded state, further defines a first cushion at a downstream edge of the first tab, and a second cushion at a downstream edge of the second tab.

6. The apparatus according to claim 5, wherein the first cushion and the second cushion are disposed downstream of the first prosthetic leaflet and the second prosthetic leaflet.

7. The apparatus according to claim 5, wherein neither the first cushion nor the second cushion is in contact with the first prosthetic leaflet or the second prosthetic leaflet.

8. The apparatus according to claim 5, wherein:
  the sheet defines a first-tab fold and a second-tab fold,
  the first cushion comprises the first-tab fold, folded between the first-tab inner layer and the first-tab outer layer, and
  the second cushion comprises the second-tab fold, folded between the second-tab inner layer and the second-tab outer layer.

9. The apparatus according to claim 8, wherein:
  the first-tab fold is a first-tab outer fold, continuous with the first-tab outer layer,
  the second-tab fold is a second-tab outer fold, continuous with the second-tab outer layer,
  the sheet further defines:
    a first-tab inner fold, continuous with the first-tab inner layer, and
    a second-tab inner fold, continuous with the second-tab inner layer,
  the first cushion comprises:
    the first-tab outer fold, folded between the first-tab outer layer and the first-tab inner fold, and
    the first-tab inner fold, folded between the first-tab inner layer and the first-tab outer fold, and
  the second cushion comprises:
    the second-tab outer fold, folded between the second-tab outer layer and the second-tab inner fold, and
    the second-tab inner fold, folded between the second-tab inner layer and the second-tab outer fold.

10. The apparatus according to claim 1, further comprising a stitching, stitched through the first-tab inner layer, the first-leaflet commissural portion, the second-leaflet commissural portion, and the second-tab inner layer.

11. The apparatus according to claim 10, further comprising a separate flexible sheet, sandwiched between the first-leaflet commissural portion and the second-leaflet commissural portion, the stitching being stitched through the separate flexible sheet.

12. The apparatus according to claim 10, wherein the first-tab outer layer and the second-tab outer layer cover the stitching.

13. The apparatus according to claim 12, wherein the stitching is a first stitching, and wherein the apparatus further comprises a second stitching, stitched through the first-tab outer layer, the first-tab inner layer, the first-leaflet commissural portion, the second-leaflet commissural portion, the second-tab inner layer, and the second-tab outer layer.

14. The apparatus according to claim 13, wherein the first tab and the second tab each defines a loose region, disposed further away from the panel than the first stitching and the second stitching, the loose region being loose with respect to the first prosthetic leaflet and the second prosthetic leaflet.

15. The apparatus according to claim 13, wherein:
  the first stitching is stitched along a first stitch line,
  the second stitching is stitched along a second stitch line, and
  the first stitch line and the second stitch line diverge from each other at 10-45 degrees.

16. The apparatus according to claim 15, wherein the first stitch line and the second stitch line diverge from each other at 10-30 degrees.

17. The apparatus according to claim 16, wherein the first stitch line and the second stitch line diverge from each other at 15-25 degrees.

18. The apparatus according to claim 17, wherein the first stitch line and the second stitch line diverge from each other at 20 degrees.

19. The apparatus according to claim 15, wherein:
- the first-tab outer layer is defined by the second part of the first tab portion being folded back, along a first-tab fold line, over the first part of the first tab portion, such that an angle between the first-tab fold line and the first stitching is smaller than an angle between the first-tab fold line and the second stitching, and
- the second-tab outer layer is defined by the second part of the second tab portion being folded back, along a second-tab fold line, over the first part of the second tab portion, such that an angle between the second-tab fold line and the first stitching is smaller than an angle between the second-tab fold line and the second stitching.

* * * * *